(12) United States Patent
Wang et al.

(10) Patent No.: US 9,227,963 B2
(45) Date of Patent: Jan. 5, 2016

(54) APOPTOSIS-INDUCING AGENTS FOR THE TREATMENT OF CANCER AND IMMUNE AND AUTOIMMUNE DISEASES

(71) Applicant: AbbVie Inc., North Chicago, IL (US)

(72) Inventors: Le Wang, Vernon Hills, IL (US); George Doherty, Libertyville, IL (US); Xilu Wang, Libertyville, IL (US); Zhi-Fu Tao, Gurnee, IL (US); Milan Bruncko, Green Oaks, IL (US); Aaron R. Kunzer, Arlington Heights, IL (US); Michael D. Wendt, Vernon Hills, IL (US); Xiaohong Song, Grayslake, IL (US); Robin Frey, Libertyville, IL (US); Todd M. Hansen, Grayslake, IL (US); Gerard M. Sullivan, Lake Villa, IL (US); Andrew Judd, Grayslake, IL (US); Andrew J. Souers, Evanston, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 14/543,817

(22) Filed: Nov. 17, 2014

(65) Prior Publication Data
US 2015/0072978 A1    Mar. 12, 2015

Related U.S. Application Data

(63) Continuation of application No. 13/649,900, filed on Oct. 11, 2012, now Pat. No. 8,889,675.

(60) Provisional application No. 61/547,162, filed on Oct. 14, 2011.

(51) Int. Cl.
| | |
|---|---|
| *A61K 31/535* | (2006.01) |
| *C07D 417/14* | (2006.01) |
| *C07D 401/04* | (2006.01) |
| *C07D 471/04* | (2006.01) |
| *C07D 487/04* | (2006.01) |
| *C07D 493/08* | (2006.01) |
| *C07D 513/04* | (2006.01) |

(52) U.S. Cl.
CPC ............ *C07D 417/14* (2013.01); *C07D 401/04* (2013.01); *C07D 471/04* (2013.01); *C07D 487/04* (2013.01); *C07D 493/08* (2013.01); *C07D 513/04* (2013.01)

(58) Field of Classification Search
CPC .. C07D 417/14; C07D 401/04; C07D 471/04; C07D 487/04; C07D 493/08; C07D 513/04
See application file for complete search history.

(56) References Cited

U.S. PATENT DOCUMENTS

| | | | |
|---|---|---|---|
| 4,107,167 | A | 8/1978 | Lorenz et al. |
| 6,699,857 | B1 | 3/2004 | Stoltefuss et al. |
| 7,091,227 | B2 | 8/2006 | Scott et al. |
| 7,713,994 | B2 | 5/2010 | Tsou et al. |
| 8,114,893 | B2 | 2/2012 | Baell et al. |
| 8,232,273 | B2 | 7/2012 | Baell et al. |
| 8,518,970 | B2 | 8/2013 | Baell et al. |
| 8,883,784 | B2 | 11/2014 | Judd et al. |
| 8,940,737 | B2 | 1/2015 | Wang et al. |
| 9,067,928 | B2 | 6/2015 | Baell et al. |
| 2004/0077643 | A1 | 4/2004 | Ogawa et al. |
| 2005/0124614 | A1 | 6/2005 | Gangloff et al. |
| 2007/0054892 | A1 | 3/2007 | Isaacs et al. |
| 2013/0096120 | A1 | 4/2013 | Wang et al. |
| 2013/0096121 | A1 | 4/2013 | Wang et al. |
| 2014/0005190 | A1 | 1/2014 | Baell et al. |
| 2014/0073640 | A1 | 3/2014 | Judd et al. |

FOREIGN PATENT DOCUMENTS

| | | |
|---|---|---|
| CN | 101356159 A | 1/2009 |
| JP | 2003313168 A | 3/2003 |
| WO | 2009/039553 A1 | 4/2009 |
| WO | 2010065865 A2 | 6/2010 |
| WO | 2010/080478 A1 | 7/2010 |
| WO | 2010/080503 A1 | 7/2010 |
| WO | WO 2010080503 A1 * | 7/2010 |
| WO | 2013/055895 A1 | 4/2013 |
| WO | 2013/055897 A1 | 4/2013 |
| WO | 2014/039855 A1 | 3/2014 |

OTHER PUBLICATIONS

Almerico, Anna Maria, et al., "In-silico screening of new potential Bcl-2/Bcl-xl inhibitors as apoptosis modulators," Journal of Molecular Modeling, (2009), pp. 349-355, vol. 15, Issue 4.

Barelier, Sarah et al., "Fragment-based deconstruction of Bcl-xL Inhibitors," Journal of Medicinal Chemistry, (2010), vol. 53, Issue 6, pp. 2577-2588.

Hunter, Allison, M., et al., "The inhibitors of apoptosis (IAPs) as cancer targets," Apoptosis; An International Journal on Programmed Cell Death, (Jun. 19, 2007), vol. 12, Issue 9, pp. 1543-1568.

International Searching Authority, "International Search Report and Written Opinion, PCT/US2012/059720," (Dec. 6, 2012), 12 pp.

Juin, P. et al., Biochimica et Biophysica Acta: "Shooting at Survivors: Bcl-2 Family Members as Drug Taraets for Cancer"; (2004), vol. 1644, pp. 251-260.

* cited by examiner

*Primary Examiner* — Wu-Cheng Winston Chen
*Assistant Examiner* — Jean Cornet
(74) *Attorney, Agent, or Firm* — Jones Day

(57) ABSTRACT

Disclosed are compounds which inhibit the activity of anti-apoptotic Bcl-xL proteins, compositions containing the compounds and methods of treating diseases during which is expressed anti-apoptotic Bcl-xL protein.

2 Claims, No Drawings

APOPTOSIS-INDUCING AGENTS FOR THE TREATMENT OF CANCER AND IMMUNE AND AUTOIMMUNE DISEASES

This application is a continuation of U.S. patent application Ser. No. 13/649,900, filed Oct. 11, 2012, which claims priority to U.S. Provisional Application No. 61/547,162, filed Oct. 14, 2011, which are hereby incorporated by reference in their entireties into this application.

FIELD OF THE INVENTION

This invention pertains to compounds which inhibit the activity of Bcl-xL anti-apoptotic proteins, compositions containing the compounds, and methods of treating diseases during which anti-apoptotic Bcl-xL proteins are expressed.

BACKGROUND OF THE INVENTION

Apoptosis is recognized as an essential biological process for tissue homeostasis of all living species. In mammals in particular, it has been shown to regulate early embryonic development. Later in life, cell death is a default mechanism by which potentially dangerous cells (e.g., cells carrying cancerous defects) are removed. Several apoptotic pathways have been uncovered, and one of the most important involves the Bcl-2 family of proteins, which are key regulators of the mitochondrial (also called "intrinsic") pathway of apoptosis. See, Danial, N. N. and Korsmeyer, S. J. Cell (2004) 116, 205-219. The structural homology domains BH1, BH2, BH3 and BH4 are characteristic of this family of proteins. The Bcl-2 family of proteins can be further classified into three subfamilies depending on how many of the homology domains each protein contains and on its biological activity (i.e., whether it has pro- or anti-apoptotic function).

The first subgroup contains proteins having all 4 homology domains, i.e., BH1, BH2, BH3 and BH4. Their general effect is anti-apoptotic, that is to preserve a cell from starting a cell death process. Proteins such as, for example, Bcl-2, Bcl-w, Bcl-xL, Mcl-1 and Bfl-1/A1 are members of this first subgroup. Proteins belonging to the second subgroup contain the three homology domains BH1, BH2 and BH3, and have a pro-apoptotic effect. The two main representative proteins of this second subgroup are Bax and Bak. Finally, the third subgroup is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is still not entirely known and understanding this mechanism is an active area of research in the science community. In one hypothesis of regulation of cell death by Bcl-2 family proteins, the BH3-only proteins are further categorized as either "activator" (e.g., Bim and Bid) or "sensitizer" (e.g., Bad, Bik, Noxa, Hrk, Bmf, and Puma) proteins depending on their regulatory function.

The key to tissue homeostasis is achieving the delicate balance in the interactions among the three subgroups of protein in cells. Recent studies have tried to elucidate the mechanisms by which pro-apoptotic and anti-apoptotic subgroups of Bcl-2 family proteins interact to allow a cell to undergo programmed cell death. After receiving intra- or extracellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins (e.g., Puma, Bim, Bid) are "activators" in that these proteins directly engage pro-apoptotic proteins Bax and Bak to initiate MOMP, while other BH3-only proteins (e.g., Bad, Bik and Noxa) are "sensitizers" and induce Bax and Bak oligomerization indirectly by binding anti-apoptotic proteins (e.g., Bcl-2, Bcl-xL, Bcl-w, Mcl-1) and displacing and "freeing-up" the "activator" BH3-only proteins, which subsequently bind to and activate pro-apoptotic proteins (e.g., Bax, Bak) to induce cell death. Other researchers suggest that anti-apoptotic proteins engage and seqeuester Bax and Bak directly and all BH3-only proteins regulates this interaction by binding to anti-apoptotic proteins (e.g., Bcl-2, Bcl-xL, Bcl-w, Mcl-1) which results in the release Bax and Bak. See, Adams, J. M. and Cory S. *Oncogene* (2007) 26, 1324-1337; Willis, S. N. et al. *Science* (2007) 315, 856-859. Although the exact interactions through which the anti- and pro-apoptotic Bcl-2 family proteins regulate apoptosis remain under debate, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In one aspect, the implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl-2 and Bcl-xL, are over-expressed in many cancer cell types. See, Zhang J. Y., *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings as well as numerous others have made possible the emergence of new strategies in drug discovery for targeting cancer. If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival).

Researchers also have demonstrated that platelets also contain the necessary apoptotic machinery (e.g., Bax, Bak, Bcl-xL, Bcl-2, cytochrome c, caspase-9, caspase-3 and APAF-1) to execute programmed cell death through the intrinsic apoptotic pathway. Although circulating platelet production is a normal physiological process, a number of diseases are caused or exacerbated by excess of, or undesired activation of, platelets. The above suggests that therapeutic agents capable of inhibiting anti-apoptotic proteins in platelets and reducing the number of platelets in mammals may be useful in treating pro-thrombotic conditions and diseases that are characterized by an excess of, or undesired activation of, platelets.

We have developed a class of small molecule BH3-only protein mimetics, i.e., ABT-737 and ABT-263, that bind strongly to a subset of anti-apoptotic Bcl-2 proteins including Bcl-2, Bcl-w and Bcl-xL, but only weakly to Mcl-1 and A1, and exhibits mechanism-based cytotoxicity. These compounds were tested in animal studies and demonstrated cytotoxic activity in certain xenograft models as single agents, as well as enhanced the effects of a number of chemotherapeutic agents on other xenograft models when used in combination. See, Tse, C. et al. *Cancer Res* (2008) 68, 3421-3428; and van Delft, M. F. et al. *Cancer Cell* (2006) 10, 389-399. These in vivo studies suggest the potential utility of inhibitors of anti-apoptotic Bcl-2 family proteins for the treatment of diseases that involve a dysregulated apoptotic pathway.

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal (i.e., non-cancerous) cells, and the recognized inter-cell type variability of Bcl-2 family protein expression, it is advantageous to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others (e.g., lymphopenia has been observed in Bcl-2 deficient mice). See, Nakayama, K. et al. *PNAS* (1994) 91, 3700-3704.

In view of the above, there is a need in the art for small molecules therapeutics that can selectively inhibit the activity of one type or a subset of anti-apoptotic Bcl-2 proteins, for example, of a Bcl-xL anti-apoptotic protein. The present invention fulfills at least this need.

SUMMARY OF THE INVENTION

One embodiment of this invention, therefore, pertains to compounds or therapeutically acceptable salts thereof, which are useful as inhibitors of anti-apoptotic Bcl-xL proteins, the compounds having Formula (I)

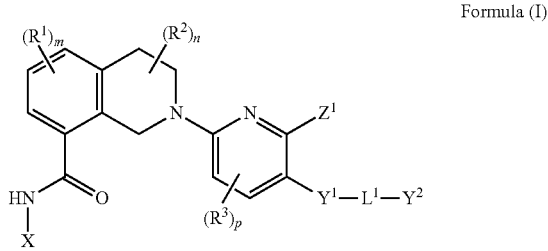

Formula (I)

wherein

X is heteroaryl; wherein the heteroaryl represented by X is optionally substituted with one, two, three, or four $R^4$;

$Y^1$ is phenylene or $C_{5-6}$ heteroarylene; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^1$ is optionally substituted with one, two, three, or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_5$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s NR^{6A}$—$(CR^6R^7)_r$, $(CR^6R^7)_s$—S(O)$_2NR^{6A}$—$(CR^6R^7)_r$, and $(CR^6R^7)_s$—$NR^{6A}S(O)_2$—$(CR^6R^7)_r$;

$Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

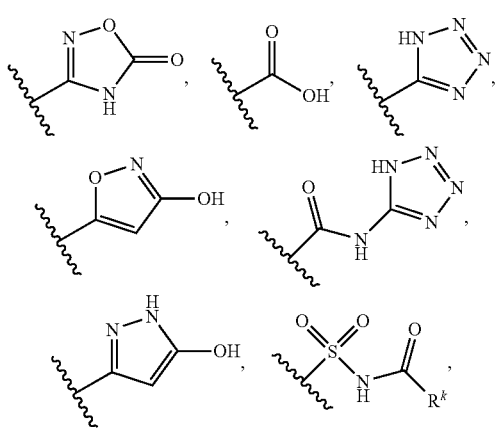

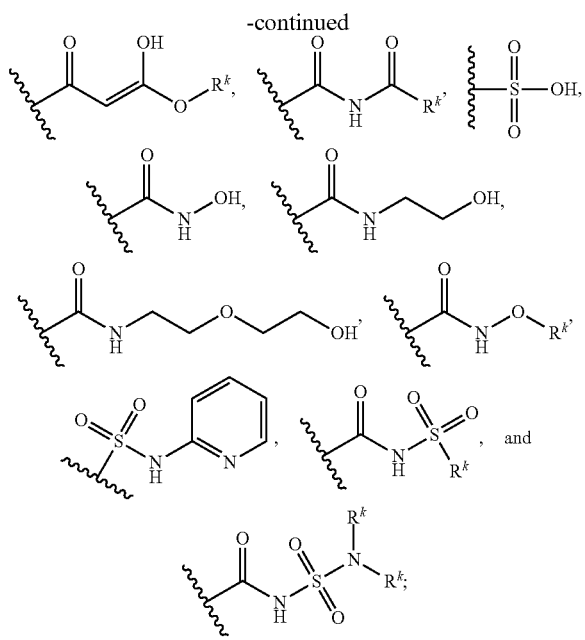

R[1], at each occurrence, is independently selected from the group consisting of halo, $C_{1-6}$ alkyl, $C_{2-6}$ alkenyl, $C_{2-6}$ alkynyl, and $C_{1-6}$ haloalkyl;

R[2], at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two R[2] that are attached to the same carbon atom, together with said carbon atom, optionally form a ring selected from the group consisting of heterocycloalkyl, heterocycloalkenyl, cycloalkyl, and cycloalkenyl;

R[3], at each occurrence, is independently selected from the group consisting of halo, $C_{1-6}$ alkyl, $C_{2-6}$ alkenyl, $C_{2-6}$ alkynyl, and $C_{1-6}$ haloalkyl;

R[4], at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

R[5], at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

R[6A] is independently selected from the group consisting of hydrogen, $C_{1-6}$ alkyl, $C_{2-6}$ alkenyl, $C_{2-6}$ alkynyl, and $C_{1-6}$ haloalkyl;

R[6] and R[7], at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{5}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

R[8], at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the R[8] $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the R[8] aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

R[9] is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and R[10] and R[11], at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or R[10] and R[11], or R[10] and R[9], together with the atom to which each is attached are combined to form a heterocyclyl;

R[k], at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

R[12] and R[13], at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

R[14], at each occurrence, is independently selected from the group consisting of $C_{1-4}$ alkyl, $C_{2-4}$ alkenyl, $C_{2-4}$ alkynyl and $C_{1-4}$ haloalkyl;

R[12] and R[13], or R[12] and R[14], at each occurrence, together with the atom to which each is attached, are optionally combined to form a heterocyclyl;

R[15], at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the R[15] $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $O-(C_{1-4}$ alkyl), $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

R[16], at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the R[16] $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;

s is 0, 1, 2, or 3;

r is 0, 1, 2, or 3;

wherein the sum of s and r is 0, 1, or 2;

m is 0, 1, 2, or 3;

n is 0, 1, 2, 3, 4, 5, or 6; and p is 0, 1, or 2.

In another embodiment of Formula (I), $Y^1$ is pyrrolyl, pyrazolyl, or triazolyl.

In another embodiment of Formula (I), $Y^1$ is pyridinyl or phenyl.

In another embodiment of Formula (I), X is X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo

[4,5-b]pyridinyl, imidazo[1,2-a]pyrazinyl, or imidazo[1,2-b]pyridazinyl, which are optionally substituted with one, two, three or four $R^4$. In another embodiment of Formula (I), $Y^1$ is pyrrolyl, pyrazolyl, or triazolyl, and X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (I), $Y^1$ is pyridinyl or phenyl, and X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$.

In another embodiment of Formula (I), $Y^1$ is pyrrolyl, pyrazolyl, or triazolyl; and $Z^1$ is selected from the group consisting of

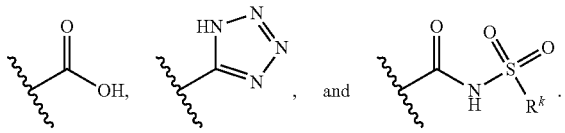

In another embodiment of Formula (I), $Y^1$ is pyridinyl or phenyl; and $Z^1$ is selected from the group consisting of

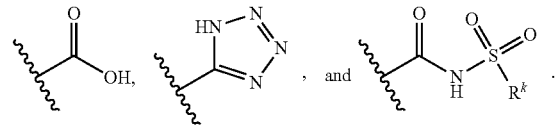

In another embodiment of Formula (I), $Y^1$ is pyridinyl or phenyl; $L^1$ is $(CR^6R^7)_q$; and $Y^2$ is selected from the group consisting of $C_{8-14}$ cycloalkyl, and $C_{8-14}$ heterocycloalkyl; wherein $R^6$ and $R^7$, at each occurrence, are hydrogen; and q is 1 or 2. In another embodiment of Formula (I), $Y^1$ is pyrrolyl, pyrazolyl, or triazolyl; $L^1$ is $(CR^6R^7)_q$; and $Y^2$ is selected from the group consisting of $C_{8-14}$ cycloalkyl, and $C_{8-14}$ heterocycloalkyl; wherein $R^6$ and $R^7$, at each occurrence, are hydrogen; and q is 1 or 2.

In another embodiment of Formula (I), $Y^1$ is pyrrolyl, pyrazolyl, or triazolyl; $L^1$ is selected from the group consisting of $(CR^6R^7)_s$—S(O)$_2$—$(CR^6R^7)_r$, $(CR^6R^7)_s$—C(O)NR$^{6A}$—$(CR^6R^7)_r$, and $(CR^6R^7)_s$—S(O)$_2$NR$^{6A}$—$(CR^6R^7)_r$; $Y^2$ is selected from the group consisting of $C_{8-14}$ cycloalkyl and $C_{8-14}$ heterocycloalkyl; s is 0; r is 0 or 1; $R^{6A}$ is independently selected from the group consisting of hydrogen, and $C_{1-6}$ alkyl; and $R^6$ and $R^7$, at each occurrence, are hydrogen. In another embodiment of Formula (I), $Y^1$ is pyridinyl or phenyl; $L^1$ is selected from the group consisting of $(CR^6R^7)_s$—O—$(CR^6R^7)_r$, $(CR^6R^7)_s$S—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, and $(CR^6R^7)_s$—S(O)$_2$NR$^{6A}$—$(CR^6R^7)_r$; $Y^2$ is selected from the group consisting of $C_{8-14}$ cycloalkyl, and $C_{8-14}$ heterocycloalkyl; s is 0; r is 0 or 1; $R^{6A}$ is independently selected from the group consisting of hydrogen, and $C_{1-6}$ alkyl; and $R^6$ and $R^7$, at each occurrence, are hydrogen.

Still another embodiment pertains to a compound having Formula (I), selected from the group consisting of 6-[8-(1,3-benzothiazol-2-ylcarbamoyl)-3,4-dihydroisoquinolin-2(1H)-yl]-3-{1-[tricyclo[3.3.1.1$^{3,7}$]dec-1-ylmethyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[3,5-dimethyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-hydroxytricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3,5,7-trimethyltricyclo[3.3.1.1$^{3,7}$]dec-1-yl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(tricyclo[3.3.1.1$^{3,7}$]dec-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-bromotricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(propan-2-yloxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-oxatricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(morpholin-4-yl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-5-methyl-1H-pyrazol-4-yl)pyridine-2-carboxylic acid;

N-(1,3-benzothiazol-2-yl)-2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{6-[(cyclopropylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{5-[5-methyl-1-(tricyclo[3.3.1.1$^{3,7}$]dec-1-ylmethyl)-1H-pyrazol-4-yl]-6-(2H-tetrazol-5-yl)pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-{2-methyl-4-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroisoquinolin-2(1H)-yl]-{3-[tricyclo[3.3.1.1$^{3,7}$]dec-1-ylmethoxy]phenyl})pyridine-2-carboxylic acid;

6-[8-(1,3-benzothiazol-2-ylcarbamoyl)-3,4-dihydroisoquinolin-2(1H)-yl]-3-[5-cyano-2-methyl-1-(tricyclo[3.3.1.1$^{3,7}$]dec-1-ylmethyl)-1H-pyrrol-3-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-2'-(tricyclo[3.3.1.1$^{3,7}$]dec-1-ylmethoxy)-3,4'-bipyridine-2-carboxylic acid;

6-[8-(1,3-benzothiazol-2-ylcarbamoyl)-3,4-dihydroisoquinolin-2(1H)-yl]-3-[1-({3-[2-(morpholin-4-yl)ethoxy]tricyclo[3.3.1.1$^{3,7}$]dec-1-yl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylmethoxy)-3,4'-bipyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid;

6-[8-(1,3-benzothiazol-2-ylcarbamoyl)-3,4-dihydroisoquinolin-2(1H)-yl]-3-{5-cyano-1-[tricyclo[3.3.1.1$^{3,7}$]dec-1-ylmethyl]-1H-pyrazol-4-yl}pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[4,5-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(1,1-dioxidothiomorpholin-4-yl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-cyano-2-methyl-1-[2-(tricyclo[3.3.1.1$^{3,7}$]dec-1-yl)ethyl]-1H-pyrrol-3-yl}pyridine-2-carboxylic acid;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(methylsulfonyl)carbamoyl]pyridin-2-yl}-1,2,3,4-tetrahydroisoquinoline-8-carboxamide;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(cyclopropylsulfonyl)carbamoyl]pyridin-2-yl}-1,2,3,4-tetrahydroisoquinoline-8-carboxamide;

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-(1-{[3-methoxy-5,7-dimethyltricyclo[3.3.1.1$^{3,7}$]dec-1-yl]methyl}-5-methyl-1H-pyrazol-4-yl)pyridine-2-carboxylic acid;

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(morpholin-4-ylsulfonyl)carbamoyl]pyridin-2-yl}-1,2,3,4-tetrahydroisoquinoline-8-carboxamide;

N-(1,3-benzothiazol-2-yl)-2-[5-(1-{[3-methoxytricyclo[3.3.1.1$^{3,7}$]dec-1-yl]methyl}-5-methyl-1H-pyrazol-4-yl)-6-{[(trifluoromethyl)sulfonyl]carbamoyl}pyridin-2-yl]-1,2,3,4-tetrahydroisoquinoline-8-carboxamide;

N-(1,3-benzothiazol-2-yl)-2-{6-[(cyclopropylsulfonyl)carbamoyl]-5-(1-{[3-methoxytricyclo[3.3.1.1$^{3,7}$]dec-1-yl]methyl}-5-methyl-1H-pyrazol-4-yl)pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid;

6-[8-(1,3-benzothiazol-2-ylcarbamoyl)-1-methyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)(1,1-$^2$H$_2$)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclooctyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid;

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl})pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid;

6-[8-(1,3-benzothiazol-2-ylcarbamoyl)-3,4-dihydroisoquinolin-2(1H)-yl]-3-(1-{[2-(2-methoxyethyl)tricyclo[3.3.1.1$^{3,7}$]dec-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-1,2,3-triazol-4-yl]pyridine-2-carboxylic acid;

6-[8-(1,3-benzothiazol-2-ylcarbamoyl)-3,4-dihydroisoquinolin-2(1H)-yl]-3-(5-cyano-1-{[3-methoxytricyclo[3.3.1.1$^{3,7}$]dec-1-yl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid;

6-[8-(1,3-benzothiazol-2-ylcarbamoyl)-3,4-dihydroisoquinolin-2(1H)-yl]-2'-[cyclooctyl(methyl)amino]-3'-methyl-3,4'-bipyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(2-methyl-3-{methyl[(tricyclo[3.3.1.1$^{3,7}$]dec-2-yl]carbamoyl}phenyl)pyridine-2-carboxylic acid;

6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-1,2,3-triazol-4-yl]pyridine-2-carboxylic acid;

3-[5-methyl-1-(2-oxatricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfonyl)-3,4'-bipyridine-2-carboxylic acid;

6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1$^{3,7}$]dec-1-ylmethyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-{5-cyano-2-methyl-1-[(3-methyl-2-oxatricyclo[3.3.1.1$^{3,7}$]dec-1-yl)methyl]-1H-pyrrol-3-yl}pyridine-2-carboxylic acid;

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid;

2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-N-([1,3]thiazolo[5,4-b]pyridin-2-yl)-1,2,3,4-tetrahydroisoquinoline-8-carboxamide;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid;

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-methyl-1-{[3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl})-5-methyl-1H-pyrazol-4-yl)pyridine-2-carboxylic acid; and therapeutically acceptable salts, metabolites, prodrugs, salts of metabolites, and salts of prodrugs thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, cyclooxtanyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. Examples of spirocyclic carbocyclyls include spiropentanyl, spiro[3.5]nonanyl, and spiro[2.5]octanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl (tricyclo[3.3.1.1$^{3,7}$]decanyl). In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, cyclohexyl, cycloheptanyl, and cyclooctanyl. A cycloalkyl may alternatively be polycyclic or contain more than one ring. Examples of polycyclic cycloalkyls include bridged, fused, and spirocyclic carbocyclyls. Examples of bridged cycloalkyls include adamantanyl (tricyclo[3.3.1.1$^{3,7}$]decanyl), and bicyclo[3.1.1]heptanyl.

The term "$C_x$-$C_y$ cycloalkyl" means a cycloalkyl ring system containing from x to y carbon atoms. For example "$C_3$-$C_7$ cycloalkyl" means a cycloalkyl ring system containing from 3 to 7 carbon atoms.

The term "cycloalkenyl" (alone or in combination with another term(s)) means a partially saturated cyclic hydrocarbyl substituent containing from 3 to 14 carbon ring atoms. A cycloalkenyl may be a single carbon ring, which typically contains from 3 to 8 carbon ring atoms and more typically from 4 to 6 ring atoms. Examples of single-ring cycloalkenyls include cyclopentenyl, and cyclohexenyl. A cycloalkenyl may alternatively be polycyclic or contain more than one ring. Examples of polycyclic cycloalkenyls include bridged, fused, and spirocyclic carbocyclyls. Examples of bridged cycloalkenyls include bicyclo[2.2.1]hept-2-enyl.

The term "$C_x$-$C_y$ cycloalkenyl" means a cycloalkenyl ring system containing from x to y carbon atoms. For example "$C_4$-$C_7$ cycloalkenyl" means a cycloalkenyl ring system containing from 4 to 7 carbon atoms.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

The term "arylene" means a divalent arene.

The term "phenylene" means a divalent benzene.

In some instances, the number of carbon atoms in a substituent (e.g., alkyl, alkenyl, alkynyl, cycloalkyl, heterocyclyl, heteroaryl, and aryl) is indicated by the prefix "$C_x$-$C_y$-", wherein x is the minimum and y is the maximum number of carbon atoms. Thus, for example, "$C_1$-$C_6$-alkyl" refers to an alkyl containing from 1 to 6 carbon atoms. Illustrating further, "$C_3$-$C_8$-cycloalkyl" means a saturated hydrocarbyl ring containing from 3 to 8 carbon ring atoms.

The term "$C_{x-y}$ branched chain alkyl" means a saturated hydrocarbyl substituent containing from x to y carbons wherein attachment occurs through a dialkyl trivalent- or trialkyl tetravalent-carbon radical. Examples of such substituents include isopentanyl (pentan-3-yl), neopentanyl (2,2-dimethylpropan-2-yl), heptan-4-yl, and 2,6-dimethylheptan-4-yl.

The term, "$C_{3-11}$ branched chain alkyl" means a saturated hydrocarbyl substituent containing from 3 to 11 carbons wherein attachment occurs through a dialkyl trivalent- or trialkyl tetravalent-carbon radical.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "hydroxyalkyl" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means replacement by a sulfur radical, i.e. a thiaether substituent means an ether substituent wherein a divalent sulfur atom is in the place of the ether oxygen atom. Such a substituent may be depicted as —S—. For example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), 1,4-dioxanyl, dioxothiomorpholinyl, oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, diazepinyl, pyridonyl (including pyrid-2(1H)-onyl and pyrid-4(1H)-onyl), furan-2(5H)-onyl, pyrimidonyl (including pyramid-2(1H)-onyl and pyramid-4(3H)-onyl), oxazol-2(3H)-onyl, 1H-imidazol-2(3H)-onyl, pyridazin-3(2H)-onyl, and pyrazin-2(1H)-onyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. Examples of bridged heterocyclyls include 2-oxatricyclo[3.3.1.1$^{3,7}$]decane. In a fused-ring heterocyclyl, two or more rings may be fused together, such that two rings share one common bond. Examples of fused ring heterocyclyls containing two or three rings include imidazopyrazinyl (including imidazo[1,2-a]pyrazinyl), imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as dihydrochromenyl, tetrahydroisoquinolinyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), benzo[d]thiazolyl, and benzisoxazinyl (including 1,2-benzisoxazinyl or 1,4-benzisoxazinyl).

The term "heterocycloalkyl" (alone or in combination with another term(s)) means a saturated heterocyclyl.

The term "$C_x$-$C_y$ heterocycloalkyl" means a heterocycloalkyl ring system containing from x to y ring atoms. For example "$C_3$-$C_7$ heterocycloalkyl" means a heterocycloalkyl ring system containing 3 to 7 ring atoms.

The term "heterocycloalkenyl" (alone or in combination with another term(s)) means a partially saturated heterocyclyl.

The term "$C_x$-$C_y$ heterocycloalkenyl" means a heterocycloalkenyl ring system containing from x to y ring atoms. For example "$C_3$-$C_7$ heterocycloalkenyl" means a heterocycloalkenyl ring system containing from 3 to 7 ring atoms.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryls include 6-membered ring substituents such as pyridyl, pyrazyl, pyrimidinyl, pyridazinyl, and 1,3,5-, 1,2,4- or 1,2,3-triazinyl; 5-membered ring substituents such as triazolyl, pyrrolyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as imidazopyrazinyl (including imidazo[1,2-a]pyrazinyl)imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), benzo[d]thiazolyl, benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl. Heteroaryls may also be heterocycles having aromatic (4N+2 pi electron) resonance contributors such as pyridonyl (including pyrid-2(1H)-onyl and pyrid-4(1H)-onyl), pyrimidonyl (including pyramid-2(1H)-onyl and pyramid-4(3H)-onyl), pyridazin-3(2H)-onyl and pyrazin-2(1H)-onyl.

The term "$C_x$-$C_y$ heteroaryl" means a heteroaryl ring system containing from x to y ring atoms. For example "$C_5$-$C_6$ heteroaryl" means a heteroaryl ring system containing from 5 to 6 ring atoms.

The term "heteroarylene" means a divalent heteroarene.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)

ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are sometimes designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-xL inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to Bcl-xL activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Suitable groups for X, Y$^1$, L$^1$, Y$^2$, Z$^1$, R$^1$, R$^2$, R$^3$, m, n, and p in compounds of Formula (I) are independently selected. The described embodiments of the present invention may be combined. Such combination is contemplated and within the scope of the present invention. For example, it is contemplated that embodiments for any of X, Y$^1$, L$^1$, Y$^2$, Z$^1$, R$^1$, R$^2$, R$^3$, m, n, and p can be combined with embodiments defined for any other of X, Y$^1$, L$^1$, Y$^2$, Z$^1$, R$^1$, R$^2$, R$^3$, m, n, and p.

One embodiment of this invention, therefore, pertains to compounds and therapeutically acceptable salts, metabolites, prodrugs, salts of metabolites, and salts of prodrugs thereof, which are useful as inhibitors of anti-apoptotic Bcl-xL proteins, the compounds having Formula (I)

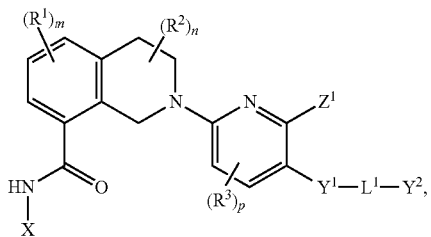

Formula (I)

wherein

X is heteroaryl; wherein the heteroaryl represented by X is optionally substituted with one, two, three, or four R$^4$;

Y$^1$ is phenylene or C$_{5-6}$ heteroarylene; optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^1$ is optionally substituted with one, two, three, or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, CO(O)H, C(O)H, OH, CN, N$_5$, NO$_2$, F, Cl, Br and I;

L$^1$ is selected from the group consisting of (CR$^6$R$^7$)$_q$, (CR$^6$R$^7$)$_s$—O—(CR$^6$R$^7$)$_r$, (CR$^6$R$^7$)$_s$—C(O)—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$NR$^{6A}$—(CR$^6$R$^7$)$_r$, (CR$^6$R$^7$)$_s$—S(O)$_2$NR$^{6A}$—(CR$^6$R$^7$)$_r$, and (CR$^6$R$^7$)$_s$—NR$^{6A}$S(O)$_2$—(CR$^6$R$^7$)$_r$;

Y$^2$ is C$_{8-14}$ cycloalkyl, C$_{8-14}$ cycloalkenyl, C$_{8-14}$ heterocycloalkyl, or C$_{8-14}$ heterocycloalkenyl; optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^2$ is optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I;

Z$^1$ is selected from the group consisting of C(O)OR$^9$, C(O)NR$^{10}$R$^{11}$, C(O)R$^{11}$, NR$^{10}$C(O)R$^{11}$, NR$^{10}$C(O)NR$^{10}$R$^{11}$, OC(O)NR$^{10}$R$^{11}$, NR$^{10}$C(O)OR$^9$, C(=NOR$^{10}$)NR$^{10}$R$^{11}$, NR$^{10}$C(=NCN)NR$^{10}$R$^{11}$, NR$^{10}$S(O)$_2$NR$^{10}$R$^{11}$, S(O)$_2$R$^9$, S(O)$_2$NR$^{10}$R$^{11}$, N(R$^{10}$)S(O)$_2$R$^{11}$, NR$^{10}$C(=NR$^{11}$)NR$^{10}$R$^{11}$, C(=S)NR$^{10}$R$^{11}$, C(=NR$^{10}$)NR$^{10}$R$^{11}$, halogen, NO$_2$, and CN; or Z$^1$ is selected from the group consisting of

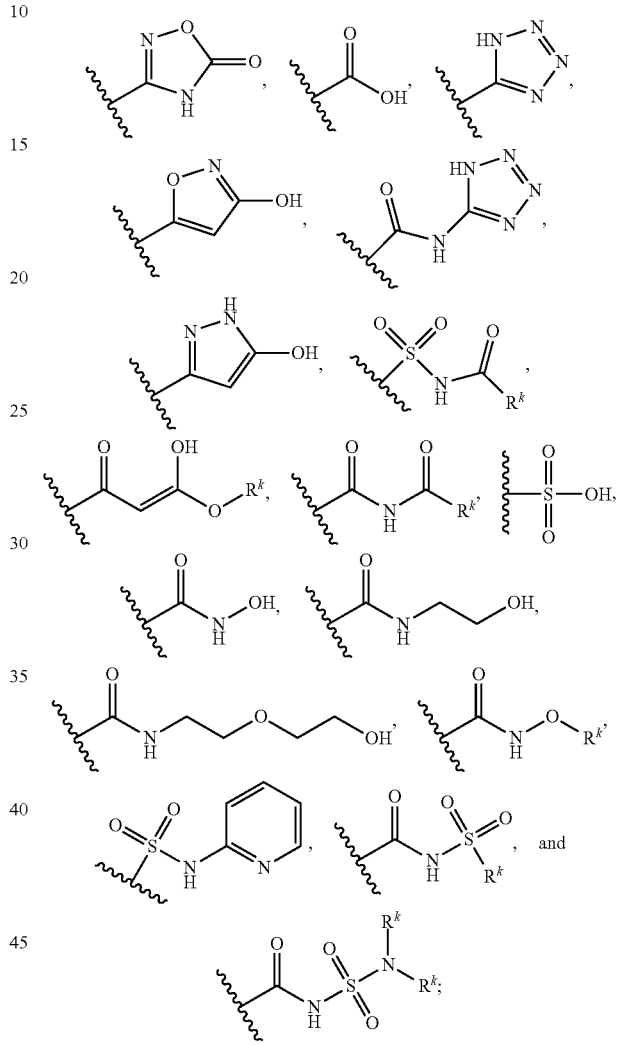

R$^1$, at each occurrence, is independently selected from the group consisting of halo, C$_{1-6}$ alkyl, C$_{2-6}$ alkenyl, C$_{2-6}$ alkynyl, and C$_{1-6}$ haloalkyl;

R$^2$, at each occurrence, is independently selected from the group consisting of deuterium, halo, C$_{1-6}$ alkyl, C$_{2-6}$ alkenyl, C$_{2-6}$ alkynyl, and C$_{1-6}$ haloalkyl;

two R$^2$ that are attached to the same carbon atom, together with said carbon atom, optionally form a ring selected from the group consisting of heterocycloalkyl, heterocycloalkenyl, cycloalkyl, and cycloalkenyl;

R$^3$, at each occurrence, is independently selected from the group consisting of halo, C$_{1-6}$ alkyl, C$_{2-6}$ alkenyl, C$_{2-6}$ alkynyl, and C$_{1-6}$ haloalkyl;

R$^4$, at each occurrence, is independently selected from the group consisting of NR$^{12}$R$^{13}$, OR$^{12}$, CN, NO$_2$, halogen, C(O)OR$^{12}$, C(O)NR$^{12}$R$^{13}$, NR$^{12}$C(O)R$^{13}$, NR$^{12}$S(O)$_2$R$^{14}$, NR$^{12}$S(O)R$^{14}$, S(O)$_2$R$^{14}$, S(O)R$^{14}$ and R$^{14}$;

R⁵, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^5$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, $OH$, $CN$, $N_3$, $NO_2$, $F$, $Cl$, $Br$ and $I$;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, $OH$, $CN$, $N_3$, $NO_2$, $F$, $Cl$, $Br$ and $I$; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, $(O)$, $OH$, $CN$, $NO_2$, $OCF_3$, $OCF_2CF_3$, $F$, $Cl$, $Br$ and $I$;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}$ $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of O—($C_{1-4}$ alkyl), $NH_2$, $C(O)NH_2$, $SO_2NH_2$, $C(O)H$, $C(O)OH$, $(O)$, $OH$, $CN$, $NO_2$, $OCF_3$, $OCF_2CF_3$, $F$, $Cl$, $Br$ and $I$;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}$ $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6; and
p is 0, 1, or 2.

In one embodiment of Formula (I), m is 0, 1, 2, or 3; n is 0, 1, 2, 3, 4, 5, or 6; and p is 0, 1, or 2. In another embodiment of Formula (I), n is 0, 1, or 2. In another embodiment of Formula (I), n is 0, 1, or 2; and each $R^2$ is independently deuterium or $C_{1-6}$ alkyl. In another embodiment of Formula (I), m, n, and p are 0.

In one embodiment of Formula (I), X is heteroaryl, which is optionally substituted with one, two, three or four $R^4$. In another embodiment of Formula (I), X is heteroaryl, which is unsubstituted. In another embodiment of Formula (I), X is heteroaryl, which is substituted with one $R^4$. In another embodiment of Formula (I), X is heteroaryl, which is substituted with two $R^4$. In another embodiment of Formula (I), X is heteroaryl, which is substituted with one $R^4$, and $R^4$ is $OR^{12}$ or halogen. In another embodiment of Formula (I), X is heteroaryl, which is substituted with two $R^4$, and each $R^4$ is independently $OR^{12}$ or halogen. In another embodiment of Formula (I), X is heteroaryl, which is substituted with one $R^4$, and $R^4$ is Cl, F, or methoxy. In another embodiment of Formula (I), X is heteroaryl, which is substituted with two $R^4$, and each $R^4$ is independently F.

In one embodiment of Formula (I), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]

pyrazinyl, or imidazo[1,2-b]pyridazinyl, which are substituted with two $R^4$, and each $R^4$ is independently $OR^{12}$ or halogen. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (I), X is benzo[d]thiazolyl, which is optionally substituted with one, two, three or four $R^4$. In another embodiment of Formula (I), X is benzo[d]thiazolyl, which is unsubstituted. In another embodiment of Formula (I), X is benzo[d]thiazolyl, which is substituted with one $R^4$. In another embodiment of Formula (I), X is benzo[d]thiazolyl, which is substituted with two $R^4$. In another embodiment of Formula (I), X is benzo[d]thiazolyl, which is substituted with one $R^4$, and $R^4$ is $OR^{12}$ or halogen. In another embodiment of Formula (I), X is benzo[d]thiazolyl, which is substituted with two $R^4$, and each $R^4$ is independently $OR^{12}$ or halogen. In another embodiment of Formula (I), X is benzo[d]thiazolyl, which is substituted with one $R^4$, and $R^4$ is Cl, F, or methoxy. In another embodiment of Formula (I), X is benzo[d]thiazolyl, which is substituted with two $R^4$, and each $R^4$ is independently F.

In one embodiment of Formula (I), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

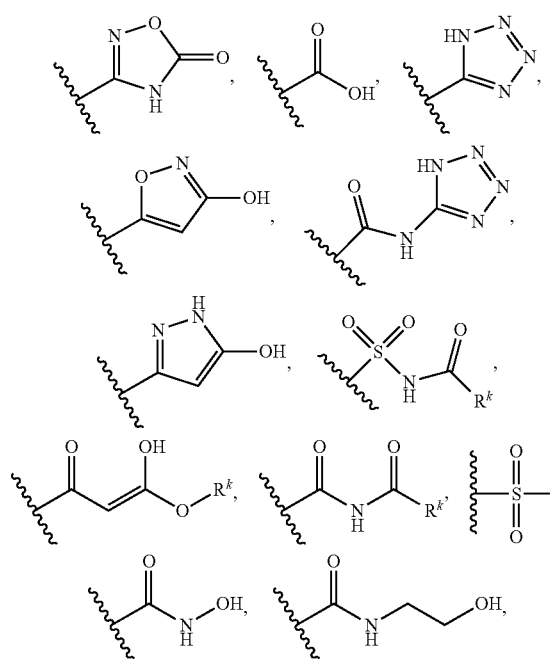

In another embodiment of Formula (I), $Z^1$ is

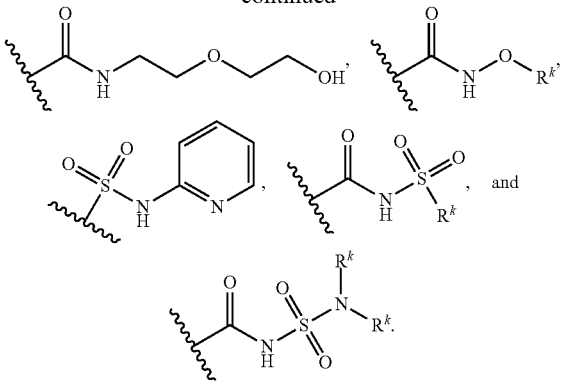

In another embodiment of Formula (I), $Z^1$ is

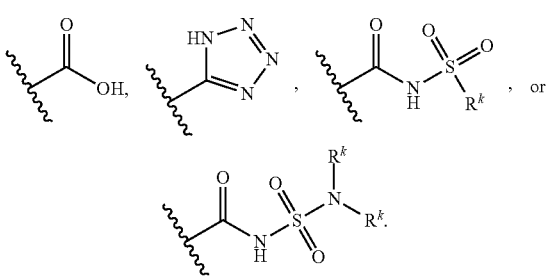

In another embodiment of Formula (I), $Z^1$ is

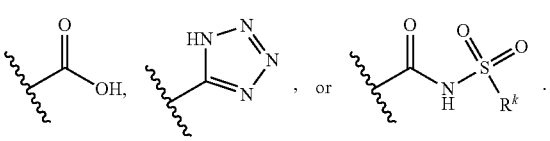

In another embodiment of Formula (I), $Z^1$ is

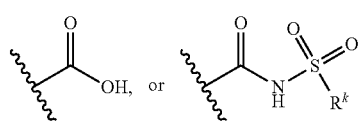

In another embodiment of Formula (I), $Z^1$ is

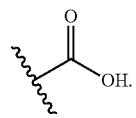

In one embodiment of Formula (I), $Y^1$ is phenylene or $C_{5-6}$ heteroarylene; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^1$ is optionally substituted with one, two, three, or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S$ (O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, CO(O)H, C(O)H, OH, CN, N$_3$, NO$_2$, F, Cl, Br and I. In another embodiment of Formula (I), Y$^1$ is phenylene or C$_{5-6}$ heteroarylene; wherein the phenylene and C$_{5-6}$ heteroarylene represented by Y$^1$ are optionally substituted with one or two substituents independently selected from the group consisting of R$^5$, CN, F, Cl, Br and I. In another embodiment of Formula (I), Y$^1$ is phenylene or C$_{5-6}$ heteroarylene; wherein the phenylene and C$_{5-6}$ heteroarylene represented by Y$^1$ are optionally substituted with one or two substituents independently selected from the group consisting of R$^5$, CN, F, Cl, Br and I; wherein R$^5$ is C$_{1-6}$ alkyl.

In another embodiment of Formula (I), Y$^1$ is pyrrolyl, pyrazolyl, triazolyl, pyridinyl, or phenyl. In another embodiment of Formula (I), Y$^1$ is pyrrolyl, pyrazolyl, or triazolyl. In another embodiment of Formula (I), Y$^1$ is pyridinyl or phenyl. In another embodiment of Formula (I), Y$^1$ is pyrrolyl, pyrazolyl, triazolyl, pyridinyl, or phenyl; wherein the pyrrolyl, pyrazolyl, triazolyl, pyridinyl, and phenyl represented by Y$^1$ are optionally substituted with one or two substituents independently selected from the group consisting of R$^5$, CN, F, Cl, Br and I. In another embodiment of Formula (I), Y$^1$ is pyrrolyl, pyrazolyl, triazolyl, pyridinyl, or phenyl; wherein the pyrrolyl, pyrazolyl, triazolyl, pyridinyl, and phenyl represented by Y$^1$ are optionally substituted with one or two substituents independently selected from the group consisting of R$^5$, CN, F, Cl, Br and I; wherein R$^5$ is C$_{1-6}$ alkyl.

In one embodiment of Formula (I), L$^1$ is selected from the group consisting of (CR$^6$R$^7$)$_q$, (CR$^6$R$^7$)$_q$, (CR$^6$R$^7$)$_s$—O—(CR$^6$R$^7$)$_r$, (CR$^6$R$^7$)$_s$—C(O)—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$NR$^{6A}$—(CR$^6$R$^7$)$_r$, (CR$^6$R$^7$)$_s$—S(O)$_2$NR$^{6A}$—(CR$^6$R$^7$)$_r$, and (CR$^6$R$^7$)$_s$—NR$^{6A}$S(O)$_2$—(CR$^6$R$^7$)$_r$; and Y$^2$ is C$_{8-14}$ cycloalkyl, C$_{8-14}$ cycloalkenyl, C$_{8-14}$ heterocycloalkyl, or C$_{8-14}$ heterocycloalkenyl; optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^2$ is optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I.

In another embodiment of Formula (I), L$^1$ is (CR$^6$R$^7$)$_q$; and Y$^2$ is selected from the group consisting of C$_{8-14}$ cycloalkyl and C$_{8-14}$ heterocycloalkyl; wherein R$^6$ and R$^7$, at each occurrence, are hydrogen; and q is 1 or 2. In another embodiment of Formula (I), L$^1$ is selected from the group consisting of (CR$^6$R$^7$)$_s$—O—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$C(O)NR$^{6A}$(CR$^6$R$^7$)$_r$, (CR$^6$R$^7$)$_s$—NR$^{6A}$—(CR$^6$R$^7$)$_r$, and (CR$^6$R$^7$)$_s$—S(O)$_2$NR$^{6A}$—(CR$^6$R$^7$)$_r$; Y$^2$ is selected from the group consisting of C$_{8-14}$ cycloalkyl, and C$_{8-14}$ heterocycloalkyl; s is 0; r is 0 or 1; R$^{6A}$ is independently selected from the group consisting of hydrogen, and C$_{1-6}$ alkyl; and R$^6$ and R$^7$, at each occurrence, are hydrogen.

In another embodiment of Formula (I),
X is heteroaryl;
Y is phenylene or C$_{5-6}$ heteroarylene; wherein Y$^1$ is optionally substituted with one, or two substituents independently selected from the group consisting of R$^5$, CN, F, Cl, Br and I;
L$^1$ is selected from the group consisting of (CR$^6$R$^7$)$_q$, (CR$^6$R$^7$)$_s$—O—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$—NR$^{6A}$—(CR$^6$R$^7$)$_r$, and (CR$^6$R$^7$)$_s$—S(O)$_2$NR$^{6A}$—(CR$^6$R$^7$)$_r$;
Y$^2$ is C$_{8-14}$ cycloalkyl, or C$_{8-14}$ heterocycloalkyl; wherein Y$^2$ is optionally substituted with one, two, or three substituents independently selected from the group consisting of R$^8$, OR$^8$, SO$_2$R$^8$, CO(O)R$^8$, OH, F, Cl, Br and I;
Z$^1$ is selected from the group consisting of

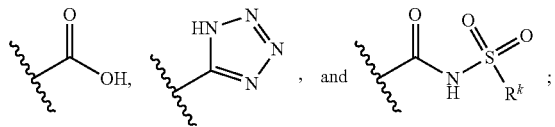

R$^2$, at each occurrence, is independently C$_{1-6}$ alkyl;
R$^5$, at each occurrence, is independently C$_{1-6}$ alkyl;
R$^{6A}$ is independently selected from the group consisting of hydrogen and C$_{1-6}$ alkyl;
R$^6$ and R$^7$, at each occurrence, are each independently hydrogen;
R$^8$, at each occurrence, is independently selected from the group consisting of C$_{1-6}$ alkyl and heterocyclyl; wherein the R$^8$C$_{1-6}$ alkyl is optionally substituted with one substituent independently selected from the group consisting of R$^{16}$, OR$^{16}$, SO$_2$R$^{16}$, and NHR$^{16}$;
R$^k$, at each occurrence, is independently selected from the group consisting of C$_{1-6}$ alkyl, C$_{3-7}$ heterocycloalkyl, C$_{3-7}$ cycloalkyl and C$_{1-6}$ haloalkyl;
R$^{16}$, at each occurrence, is independently selected from the group consisting of C$_{1-4}$ alkyl, aryl, and heterocycloalkyl; wherein the R$^{16}$C$_{1-4}$ alkyl is optionally substituted with one substituent independently selected from the group consisting of OCH$_3$, OCH$_2$CH$_2$OCH$_3$, and OCH$_2$CH$_2$NHCH$_3$;
q is 1 or 2;
s is 0;
r is 0 or 1;
wherein the sum of s and r is 0 or 1;
m is 0;
n is 0, 1, or 2; and
p is 0.

Still another embodiment pertains to a compound having Formula (I) selected from the group consisting of 6-[8-(1,3-benzothiazol-2-ylcarbamoyl)-3,4-dihydroisoquinolin-2(1H)-yl]-3-{1-[tricyclo[3.3.1.1$^{3,7}$]dec-1-ylmethyl]-1H-pyrazol-4-yl})pyridine-2-carboxylic acid;

6-[8-(1,3-benzothiazol-2-ylcarbamoyl)-3,4-dihydroisoquinolin-2(1H)-yl]-3-[3,5-dimethyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-hydroxytricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-methoxytricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-(2-methoxyethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-{1-[(3,5,7-trimethyltricyclo[3.3.1.1$^{3,7}$]dec-1-yl)methyl]-1H-pyrazol-4-yl}pyridine-2-carboxylic acid;

6-[8-(1,3-benzothiazol-2-ylcarbamoyl)-3,4-dihydroiso-quinolin-2(1H)-yl]-3-[1-(tricyclo[3.3.1.1$^{3,7}$]dec-2-ylmethyl)-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[3-bromotricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-(propan-2-yloxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-[1-(2-oxatricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[3-(morpholin-4-yl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-methoxytricyclo[3.3.1.1$^{3,7}$]dec-1-yl]methyl}-5-methyl-1H-pyrazol-4-yl)pyridine-2-carboxylic acid;

N-(1,3-benzothiazol-2-yl)-2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{6-[(cyclopropylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{5-[5-methyl-1-(tricyclo[3.3.1.1$^{3,7}$]dec-1-ylmethyl)-1H-pyrazol-4-yl]-6-(2H-tetrazol-5-yl)pyridin-2-yl}-1,2,3,4-tetrahydroisoquinoline-8-carboxamide;

6-[8-(1,3-benzothiazol-2-ylcarbamoyl)-3,4-dihydroiso-quinolin-2(1H)-yl]-3-{2-methyl-4-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroiso-quinolin-2(1H)-yl]-3-{2-methyl-3-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroiso-quinolin-2(1H)-yl]-3-{3-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroiso-quinolin-2(1H)-yl]-3-[5-cyano-2-methyl-1-(tricyclo[3.3.1.1$^{3,7}$]dec-1-ylmethyl)-1H-pyrrol-3-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroiso-quinolin-2(1H)-yl]-2'-(tricyclo[3.3.1.1$^{3,7}$]dec-1-ylmethoxy)-3,4'-bipyridine-2-carboxylic acid;

6-[8-(1,3-benzothiazol-2-ylcarbamoyl)-3,4-dihydroiso-quinolin-2(1H)-yl]-3-[1-({3-[2-(morpholin-4-yl)ethoxy]tricyclo[3.3.1.1$^{3,7}$]dec-1-yl}methyl)-1H-pyrazol-4-yl]pyridine-2-carboxylic acid;

6-[8-(1,3-benzothiazol-2-ylcarbamoyl)-3,4-dihydroiso-quinolin-2(1H)-yl]-3'-methyl-2'-(tricyclo[3.3.1.1$^{3,7}$]dec-1-ylmethoxy)-3,4'-bipyridine-2-carboxylic acid;

6-[8-(1,3-benzothiazol-2-ylcarbamoyl)-3,4-dihydroiso-quinolin-2(1H)-yl]-3-{2-methyl-3-[tricyclo[3.3.1.1$^{3,7}$]dec-1-yloxy]phenyl}pyridine-2-carboxylic acid;

6-[8-(1,3-benzothiazol-2-ylcarbamoyl)-3,4-dihydroiso-quinolin-2(1H)-yl]-3-{5-cyano-1-[tricyclo[3.3.1.1$^{3,7}$]dec-1-ylmethyl]-1H-pyrazol-4-yl}pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[4,5-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroiso-quinolin-2(1H)-yl]-3-(1-{[3,5-dimethyltricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[3-(1,1-dioxidothiomorpholin-4-yl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroiso-quinolin-2(1H)-yl]-3-{5-cyano-2-methyl-1-[2-(tricyclo[3.3.1.1$^{3,7}$]dec-1-yl)ethyl]-1H-pyrrol-3-yl}pyridine-2-carboxylic acid;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(methylsulfonyl)carbamoyl]pyridin-2-yl}-1,2,3,4-tetrahydroisoquinoline-8-carboxamide;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(cyclopropylsulfonyl)carbamoyl]pyridin-2-yl}-1,2,3,4-tetrahydroisoquinoline-8-carboxamide;

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroiso-quinolin-2(1H)-yl]-3-(1-{[3-methoxy-5,7-dimethyltricyclo[3.3.1.1$^{3,7}$]dec-1-yl]methyl}-5-methyl-1H-pyrazol-4-yl)pyridine-2-carboxylic acid;

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(morpholin-4-ylsulfonyl)carbamoyl]pyridin-2-yl}-1,2,3,4-tetrahydroisoquinoline-8-carboxamide;

N-(1,3-benzothiazol-2-yl)-2-[5-(1-{[3-methoxytricyclo[3.3.1.1$^{3,7}$]dec-1-yl]methyl}-5-methyl-1H-pyrazol-4-yl)-6-{[(trifluoromethyl)sulfonyl]carbamoyl}pyridin-2-yl]-1,2,3,4-tetrahydroisoquinoline-8-carboxamide;

N-(1,3-benzothiazol-2-yl)-2-{6-[(cyclopropylsulfonyl)carbamoyl]-5-(1-{[3-methoxytricyclo[3.3.1.1$^{3,7}$]dec-1-yl]

methyl}-5-methyl-1H-pyrazol-4-yl)pyridin-2-yl}-1,2,3,
4-tetrahydroisoquinoline-8-carboxamide;

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid;

6-[8-(1,3-benzothiazol-2-ylcarbamoyl)-1-methyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)(1,1-$^{2}$H$_{2}$)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[-(2-methoxyethyl)cyclooctyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid;

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid;

6-[8-(1,3-benzothiazol-2-ylcarbamoyl)-3,4-dihydroisoquinolin-2(1H)-yl]-3-(1-{[2-(2-methoxyethyl)tricyclo[3.3.1.1$^{3,7}$]dec-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-1,2,3-triazol-4-yl]pyridine-2-carboxylic acid;

6-[8-(1,3-benzothiazol-2-ylcarbamoyl)-3,4-dihydroisoquinolin-2(1H)-yl]-3-(5-cyano-1-{[3-methoxytricyclo[3.3.1.1$^{3,7}$]dec-1-yl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid;

6-[8-(1,3-benzothiazol-2-ylcarbamoyl)-3,4-dihydroisoquinolin-2(1H)-yl]-2'-[cyclooctyl(methyl)amino]-3'-methyl-3,4'-bipyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(2-methyl-3-{methyl[(tricyclo[3.3.1.1$^{3,7}$]dec-2-yl)carbamoyl}phenyl)pyridine-2-carboxylic acid;

6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-1,2,3-triazol-4-yl]pyridine-2-carboxylic acid;

3-[5-methyl-1-(2-oxatricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfonyl)-3,4'-bipyridine-2-carboxylic acid;

6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1$^{3,7}$]dec-1-ylmethyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-{5-cyano-2-methyl-1-[(3-methyl-2-oxatricyclo[3.3.1.1$^{3,7}$]dec-1-yl)methyl]-1H-pyrrol-3-yl}pyridine-2-carboxylic acid;

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid;

2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-N-([1,3]thiazolo[5,4-b]pyridin-2-yl)-1,2,3,4-tetrahydroisoquinoline-8-carboxamide;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid;

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-methyl-1-{[3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl})-5-methyl-1H-pyrazol-4-yl)pyridine-2-carboxylic acid; and therapeutically acceptable salts, metabolites, prodrugs, salts of metabolites, and salts of prodrugs thereof.

In another aspect, the present invention provides compounds of Formula (II)

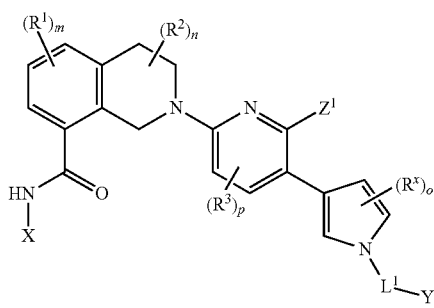

Formula (II)

and therapeutically acceptable salts, metabolites, prodrugs, salts of metabolites, and salts of prodrugs thereof, wherein X, L$^1$, Y$^2$, Z$^1$, R$^1$, R$^2$, R$^3$, m, n, and p are as described herein for Formula (I); R$^x$ is as described herein for substituents on Y$^1$, and o is 0, 1, 2, or 3.

One embodiment of this invention pertains to compounds, and therapeutically acceptable salts thereof, which are useful as inhibitors of anti-apoptotic Bcl-xL proteins, the compounds having Formula (II)

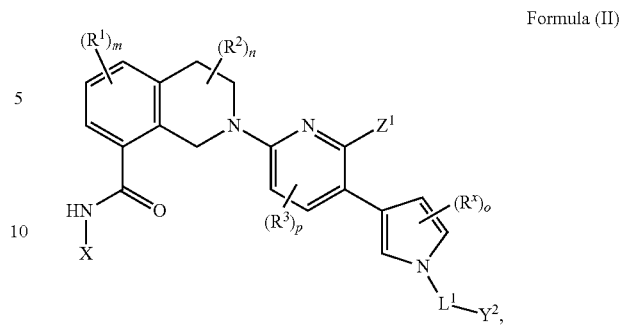

Formula (II)

wherein

X is heteroaryl; wherein the heteroaryl represented by X is optionally substituted with one, two, three, or four R$^4$;

R$^x$, at each occurrence, is independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, CO(O)H, C(O)H, OH, CN, N$_5$, NO$_2$, F, Cl, Br and I;

L$^1$ is selected from the group consisting of (CR$^6$R$^7$)$_q$, (CR$^6$R$^7$)$_s$—O—(CR$^6$R$^7$)$_r$, (CR$^6$R$^7$)$_s$—C(O)—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$—NR$^{6A}$—(CR$^6$R$^7$)$_r$, (CR$^6$R$^7$)$_s$—S(O)$_2$NR$^{6A}$—(CR$^6$R$^7$)$_r$, and (CR$^6$R$^7$)$_s$—NR$^{6A}$S(O)$_2$—(CR$^6$R$^7$)$_r$;

Y$^2$ is C$_{8-14}$ cycloalkyl, C$_{8-14}$ cycloalkenyl, C$_{8-14}$ heterocycloalkyl, or C$_{8-14}$ heterocycloalkenyl; optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^2$ is optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I;

Z$^1$ is selected from the group consisting of C(O)OR$^9$, C(O)NR$^{10}$R$^{11}$, C(O)R$^{11}$, NR$^{10}$C(O)R$^{11}$, NR$^{10}$C(O)NR$^{10}$R$^{11}$, OC(O)NR$^{10}$R$^{11}$, NR$^{10}$C(O)OR$^9$, C(=NOR$^{10}$)NR$^{10}$R$^{11}$, NR$^{10}$C(=NCN)NR$^{10}$R$^{11}$, NR$^{10}$S(O)$_2$NR$^{10}$R$^{11}$, S(O)$_2$R$^9$, S(O)$_2$NR$^{10}$R$^{11}$, N(R$^{10}$)S(O)$_2$R$^{11}$, NR$^{10}$C(=NR$^{11}$)NR$^{10}$R$^{11}$, C(=S)NR$^{10}$R$^{11}$, C(=NR$^{10}$)NR$^{10}$R$^{11}$, halogen, NO$_2$, and CN; or Z$^1$ is selected from the group consisting of

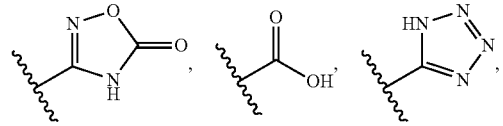

-continued

[chemical structures: isoxazol-3-ol; tetrazol-amide; pyrazol-3-ol; sulfonyl amide; enol ether ketone; acyl sulfonamide; sulfonic acid; N-hydroxy amide; N-(2-hydroxyethyl)amide; N-(2-(2-hydroxyethoxy)ethyl)amide; N-alkoxy amide; pyridyl sulfonamide; acyl sulfonamide; sulfamoyl amide]

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, CN, $NO_2$, halogen, C(O)$OR^{12}$, C(O)$NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^5$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}$ $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of O—($C_{1-4}$ alkyl), $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}$ $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;

s is 0, 1, 2, or 3;

r is 0, 1, 2, or 3;

wherein the sum of s and r is 0, 1, or 2;
m is 0, 1, 2, or 3;
n is 0, 1, 2, 3, 4, 5, or 6;
o is 0, 1, 2, or 3; and
p is 0, 1, or 2.

In one embodiment of Formula (II), m is 0, 1, 2, or 3; n is 0, 1, 2, 3, 4, 5, or 6; and p is 0, 1, or 2. In another embodiment of Formula (II), n is 0, 1, or 2. In another embodiment of Formula (II), n is 0, 1, or 2; and each $R^2$ is independently deuterium or $C_{1-6}$ alkyl. In another embodiment of Formula (II), m, n, and p are 0.

In one embodiment of Formula (II), X is heteroaryl, which is optionally substituted with one, two, three or four $R^4$. In another embodiment of Formula (II), X is heteroaryl, which is unsubstituted. In another embodiment of Formula (II), X is heteroaryl, which is substituted with one $R^4$. In another embodiment of Formula (II), X is heteroaryl, which is substituted with two $R^4$. In another embodiment of Formula (II), X is heteroaryl, which is substituted with one $R^4$, and $R^4$ is $OR^{12}$ or halogen. In another embodiment of Formula (II), X is heteroaryl, which is substituted with two $R^4$, and each $R^4$ is independently $OR^{12}$ or halogen. In another embodiment of Formula (II), X is heteroaryl, which is substituted with one $R^4$, and $R^4$ is Cl, F, or methoxy. In another embodiment of Formula (II), X is heteroaryl, which is substituted with two $R^4$, and each $R^4$ is independently F.

In one embodiment of Formula (II), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (II), X is benzo[d]thiazolyl, which is optionally substituted with one, two, three or four $R^4$. In another embodiment of Formula (II), X is benzo[d]thiazolyl, which is unsubstituted. In another embodiment of Formula (II), X is benzo[dc]thiazolyl, which is substituted with one $R^4$. In another embodiment of Formula (II), X is benzo[d]thiazolyl, which is substituted with two $R^4$. In another embodiment of Formula (II), X is benzo[d]thiazolyl, which is substituted with one $R^4$, and $R^4$ is $OR^{12}$ or halogen. In another embodiment of Formula (II), X is benzo[d]thiazolyl, which is substituted with two $R^4$, and each $R^4$ is independently $OR^{12}$ or halogen. In another embodiment of Formula (II), X is benzo[d]thiazolyl, which is substituted with one $R^4$, and $R^4$ is Cl, F, or methoxy. In another embodiment of Formula (II), X is benzo[d]thiazolyl, which is substituted with two $R^4$, and each $R^4$ is independently F.

In one embodiment of Formula (II), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

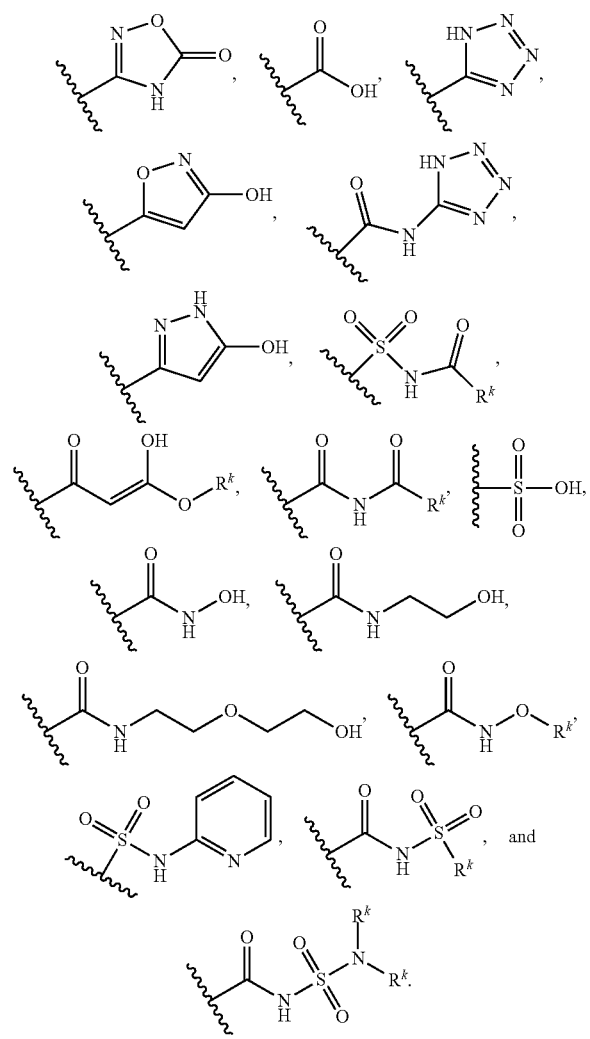

In another embodiment of Formula (II), $Z^1$ is

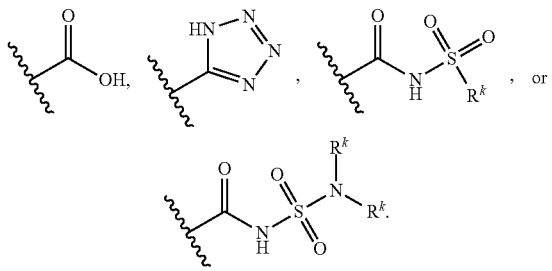

In another embodiment of Formula (II), $Z^1$ is

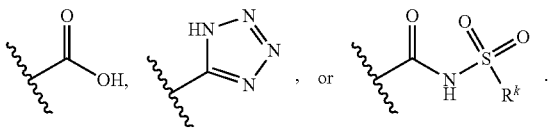

In another embodiment of Formula (II), $Z^1$ is

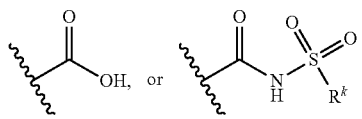

In another embodiment of Formula (II), $Z^1$ is

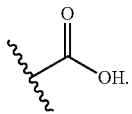 [SMILES: *C(=O)O]

In one embodiment of Formula (II), o is 0. In another embodiment of Formula (II), o is 0, 1, 2, or 3. In another embodiment of Formula (II), o is 1, 2, or 3; and $R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_5$, $NO_2$, $F$, $Cl$, $Br$ and $I$. In another embodiment of Formula (II), o is 1, 2, or 3; and $R^x$, at each occurrence, is independently selected from the group consisting of $R^5$, $CN$, $F$, $Cl$, $Br$ and $I$. In another embodiment of Formula (II), o is 1, 2, or 3; and $R^x$, at each occurrence, is independently selected from the group consisting of $R^5$, $CN$, $F$, $Cl$, $Br$ and $I$; wherein $R^5$ is $C_{1-6}$ alkyl. In another embodiment of Formula (II), o is 1 or 2; $R^x$ is $R^5$ or $CN$; and $R^5$ is $CH_3$. In another embodiment of Formula (II), o is 1; and $R^x$ is $CN$. In another embodiment of Formula (II), o is 1; and $R^x$ is $Cl$. In another embodiment of Formula (II), o is 1; $R^x$ is $R^5$; and $R^5$ is $CH_3$.

In one embodiment of Formula (II), $L^1$ is selected from the group consisting of $(CR^6R^7)_q$, $(CR^6R^7)_s$—$O$—$(CR^6R^7)_r$, $(CR^6R^7)_s$—$C(O)$—$(CR^6R^7)_r$, $(CR^6R^7)_s$—$S$—$(CR^6R^7)_r$, $(CR^6R^7)_s$—$S(O)_2$—$(CR^6R^7)_r$, $(CR^6R^7)_s$—$NR^{64}C(O)$—$(CR^6R^7)_r$, $(CR^6R^7)_s$—$C(O)NR^{64}$—$(CR^6R^7)_r$, $(CR^6R^7)_s$—$NR^{64}$—$(CR^6R^7)_r$, $(CR^6R^7)_s$—$S(O)_2NR^{64}$—$(CR^6R^7)_r$, and $(CR^6R^7)_s$—$NR^{64}S(O)_2$—$(CR^6R^7)_r$; and $Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$.

In another embodiment of Formula (II), $L^1$ is $(CR^6R^7)_q$; and $Y^2$ is selected from the group consisting of $C_{8-14}$ cycloalkyl, and $C_{8-14}$ heterocycloalkyl; wherein $R^6$ and $R^7$, at each occurrence, are hydrogen; and q is 1 or 2. In another embodiment of Formula (II), $L^1$ is selected from the group consisting of $(CR^6R^7)_s$—$S(O)_2$—$(CR^6R^7)_r$, $(CR^6R^7)_s$—$C(O)NR^{64}$—$(CR^6R^7)_r$, and $(CR^6R^7)_s$—$S(O)_2NR^{64}$—$(CR^6R^7)_r$; $Y^2$ is selected from the group consisting of $C_{8-14}$ cycloalkyl, and $C_{8-14}$ heterocycloalkyl; s is 0; r is 0 or 1; $R^{64}$ is independently selected from the group consisting of hydrogen, and $C_{1-6}$ alkyl; and $R^6$ and $R^7$, at each occurrence, are hydrogen.

In another embodiment of Formula (II),

X is heteroaryl;

$R^x$, at each occurrence, is independently selected from the group consisting of $R^5$, $CN$, $F$, $Cl$, $Br$ and $I$;

$L^1$ is selected from the group consisting of $(CR^6R^7)_q$, $(CR^6R^7)_s$—$S(O)_2$—$(CR^6R^7)_r$, $(CR^6R^7)_s$—$C(O)NR^{64}$—$(CR^6R^7)_r$, and $(CR^6R^7)_s$—$S(O)_2NR^{64}$—$(CR^6R^7)_r$;

$Y^2$ is $C_{8-14}$ cycloalkyl, or $C_{8-14}$ heterocycloalkyl; wherein $Y^2$ is optionally substituted with one, two, or three substituents independently selected from the group consisting of $R^8$, $OR^8$, $SO_2R^8$, $CO(O)R^8$, $OH$, $F$, $Cl$, $Br$ and $I$;

$Z^1$ is selected from the group consisting of

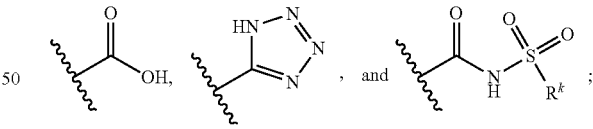

$R^2$, at each occurrence, is independently $C_{1-6}$ alkyl;

$R^5$, at each occurrence, is independently $C_{1-6}$ alkyl;

$R^{64}$ is independently selected from the group consisting of hydrogen and $C_{1-6}$ alkyl;

$R^6$ and $R^7$, at each occurrence, are each independently hydrogen;

$R^8$, at each occurrence, is independently selected from the group consisting of $C_{1-6}$ alkyl and heterocyclyl; wherein the $R^8C_{1-6}$ alkyl is optionally substituted with one substituent independently selected from the group consisting of $R^{16}$, $OR^{16}$, $SO_2R^{16}$, and $NHR^{16}$;

$R^k$, at each occurrence, is independently selected from the group consisting of $C_{1-6}$ alkyl, $C_{3-7}$ heterocycloalkyl, $C_{3-7}$ cycloalkyl and $C_{1-6}$ haloalkyl;

$R^{16}$, at each occurrence, is independently selected from the group consisting of $C_{1-4}$ alkyl, aryl, and heterocycloalkyl; wherein the $R^{16}C_{1-4}$ alkyl is optionally substituted with one substituent independently selected from the group consisting of $OCH_3$, $OCH_2CH_2OCH_3$, and $OCH_2CH_2NHCH_3$;

q is 1 or 2;
s is 0;
r is 0 or 1;
wherein the sum of s and r is 0 or 1;
m is 0;
n is 0, 1, or 2;
o is 0, 1, or 2; and
p is 0.

Still another embodiment pertains to a compound having Formula (II) selected from the group consisting of 6-[8-(1,3-benzothiazol-2-ylcarbamoyl)-3,4-dihydroisoquinolin-2(1H)-yl]-3-[5-cyano-2-methyl-1-(tricyclo[3.3.1.1$^{3,7}$]dec-1-ylmethyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-{5-cyano-2-methyl-1-[2-(tricyclo[3.3.1.1$^{3,7}$]dec-1-yl)ethyl]-1H-pyrrol-3-yl}pyridine-2-carboxylic acid;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(methylsulfonyl)carbamoyl]pyridin-2-yl}-1,2,3,4-tetrahydroisoquinoline-8-carboxamide;

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(cyclopropylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-(5-cyano-1-{[3-methoxytricyclo[3.3.1.1$^{3,7}$]dec-1-yl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1$^{3,7}$]dec-1-ylmethyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-{5-cyano-2-methyl-1-[(3-methyl-2-oxatricyclo[3.3.1.1$^{3,7}$]dec-1-yl)methyl]-1H-pyrrol-3-yl}pyridine-2-carboxylic acid; and therapeutically acceptable salts, metabolites, prodrugs, salts of metabolites, and salts of prodrugs thereof.

In another aspect, the present invention provides compounds of Formula (III)

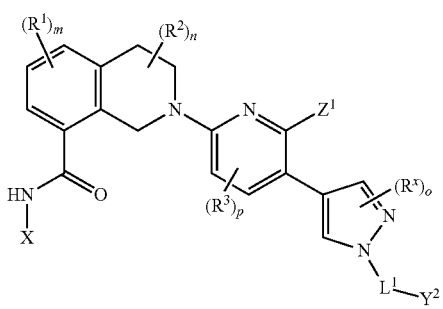

Formula (III)

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); $R^x$ is as described herein for substituents on $Y^1$, and o is 0, 1, or 2.

One embodiment of this invention pertains to compounds, and therapeutically acceptable salts thereof, which are useful as inhibitors of anti-apoptotic Bcl-xL proteins, the compounds having Formula (III)

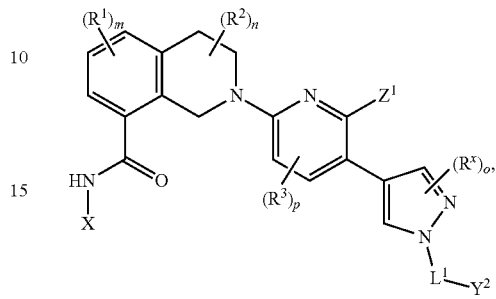

Formula (III)

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s NR^{6A}$—$(CR^6R^7)_r$, $(CR^6R^7)_s$—S(O)$_2NR^{6A}$—$(CR^6R^7)_r$, and $(CR^6R^7)_s$—$NR^{6A}S(O)_2$—$(CR^6R^7)_r$;

$Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

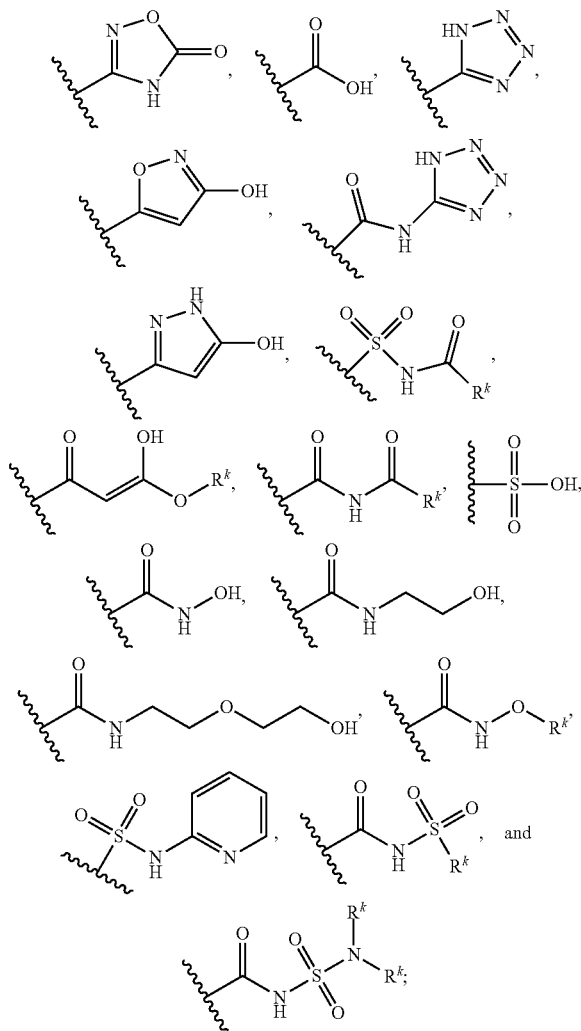

$R^1$ at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, CN, $NO_2$, halogen, C(O)$OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, CO(O)H, C(O)H, OH, CN, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8 C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, CO(O)H, C(O)H, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, C(O)H, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

$R^{12}$ and $R^{13}$, at each occurrence, are independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of O—$(C_{1-4}$ alkyl), $NH_2$, $C(O)NH_2$, $SO_2NH_2$, C(O)H, C(O)OH, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of OCH₃, OCH₂CH₂OCH₃, and OCH₂CH₂NHCH₃;
  q is 1, 2, or 3;
  s is 0, 1, 2, or 3;
  r is 0, 1, 2, or 3;
  wherein the sum of s and r is 0, 1, or 2;
  m is 0, 1, 2, or 3;
  n is 0, 1, 2, 3, 4, 5, or 6;
  o is 0, 1, or 2; and
  p is 0, 1, or 2.

In one embodiment of Formula (III), m is 0, 1, 2, or 3; n is 0, 1, 2, 3, 4, 5, or 6; and p is 0, 1, or 2. In another embodiment of Formula (III), n is 0, 1, or 2. In another embodiment of Formula (III), n is 0, 1, or 2; and each $R^2$ is independently deuterium or $C_{1-6}$ alkyl. In another embodiment of Formula (III), m, n, and p are 0.

In one embodiment of Formula (III), X is heteroaryl, which is optionally substituted with one, two, three or four $R^4$. In another embodiment of Formula (III), X is heteroaryl, which is unsubstituted. In another embodiment of Formula (III), X is heteroaryl, which is substituted with one $R^4$. In another embodiment of Formula (III), X is heteroaryl, which is substituted with two $R^4$. In another embodiment of Formula (III), X is heteroaryl, which is substituted with one $R^4$, and $R^4$ is $OR^{12}$ or halogen. In another embodiment of Formula (III), X is heteroaryl, which is substituted with two $R^4$, and each $R^4$ is independently $OR^{12}$ or halogen. In another embodiment of Formula (III), X is heteroaryl, which is substituted with one $R^4$, and $R^4$ is Cl, F, or methoxy. In another embodiment of Formula (III), X is heteroaryl, which is substituted with two $R^4$, and each $R^4$ is independently F.

In one embodiment of Formula (III), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (III), X is benzo[d]thiazolyl, which is optionally substituted with one, two, three or four $R^4$. In another embodiment of Formula (III), X is benzo[d]thiazolyl, which is unsubstituted. In another embodiment of Formula (III), X is benzo[d]thiazolyl, which is substituted with one $R^4$. In another embodiment of Formula (III), X is benzo[d]thiazolyl, which is substituted with two $R^4$. In another embodiment of Formula (III), X is benzo[d]thiazolyl, which is substituted with one $R^4$, and $R^4$ is $OR^{12}$ or halogen. In another embodiment of Formula (III), X is benzo[d]thiazolyl, which is substituted with two $R^4$, and each $R^4$ is independently $OR^{12}$ or halogen. In another embodiment of Formula (III), X is benzo[d]thiazolyl, which is substituted with one $R^4$, and $R^4$ is Cl, F, or methoxy. In another embodiment of Formula (III), X is benzo[d]thiazolyl, which is substituted with two $R^4$, and each $R^4$ is independently F.

In one embodiment of Formula (III), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

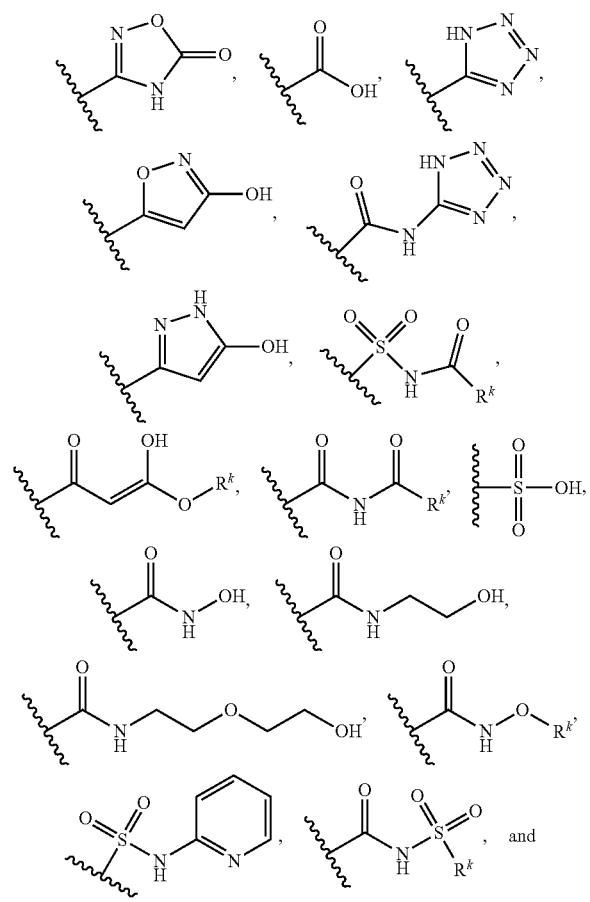

-continued

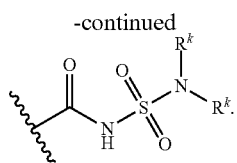

In another embodiment of Formula (III), $Z^1$ is

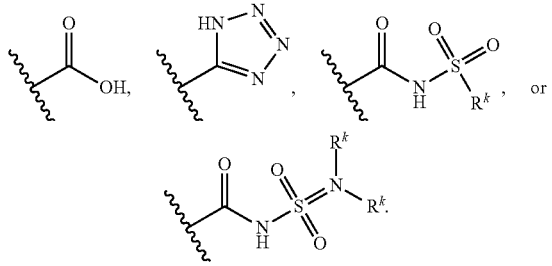

In another embodiment of Formula (III), $Z^1$ is

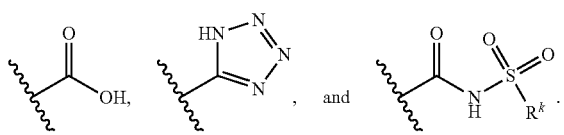

In another embodiment of Formula (III), $Z^1$ is

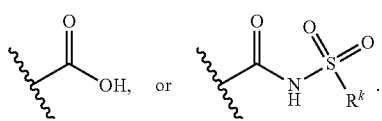

In another embodiment of Formula (III), $Z^1$ is

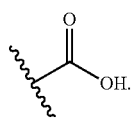 [SMILES: *C(=O)O]

In one embodiment of Formula (III), o is 0. In another embodiment of Formula (III), is 0, 1, or 2. In another embodiment of Formula (III), o is 1 or 2; and $R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, OH, CN, $N_3$, $NO_2$, F, Cl, Br and I. In another embodiment of Formula (III), o is 1 or 2; and $R^x$, at each occurrence, is independently selected from the group consisting of $R^5$, CN, F, Cl, Br and I. In another embodiment of Formula (III), o is 1 or 2; and $R^x$, at each occurrence, is independently selected from the group consisting of $R^5$, CN, F, Cl, Br and I; wherein $R^5$ is $C_{1-6}$ alkyl. In another embodiment of Formula (III), o is 1 or 2; $R^x$ is $R^5$, Cl, or CN; and $R^5$ is $CH_3$. In another embodiment of Formula (III), o is 1; and $R^x$ is CN. In another embodiment of Formula (III), o is 1; and $R^x$ is Cl. In another embodiment of Formula (III), o is 1; $R^x$ is $R^5$; and $R^5$ is $CH_3$.

In one embodiment of Formula (III), $L^1$ is selected from the group consisting of $(CR^6R^7)_q$, $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—$C(O)NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^6R^7)_r$; and $Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, OH, CN, $N_3$, $NO_2$, F, Cl, Br and I.

In another embodiment of Formula (III), $L^1$ is $(CR^6R^7)_q$; and $Y^2$ is selected from the group consisting of $C_{8-14}$ cycloalkyl, and $C_{8-14}$ heterocycloalkyl; wherein $R^6$ and $R^7$, at each occurrence, are hydrogen; and q is 1 or 2. In another embodiment of Formula (III), $L^1$ is selected from the group consisting of $(CR^6R^7)_s$—S(O)$_2$—$(CR^6R^7)_r$, $(CR^6R^7)_s$—C(O)$NR^{6A}$—$(CR^6R^7)_r$, and $(CR^6R^7)_s$—$S(O)_2NR^{6A}$—$(CR^6R^7)_r$; $Y^2$ is selected from the group consisting of $C_{8-14}$ cycloalkyl, and $C_{8-14}$ heterocycloalkyl; s is 0; r is 0 or 1; $R^{6A}$ is independently selected from the group consisting of hydrogen, and $C_{1-6}$ alkyl; and $R^6$ and $R^7$, at each occurrence, are hydrogen.

In another embodiment of Formula (III),
X is heteroaryl;
$R^x$, at each occurrence, is independently selected from the group consisting of $R^5$, CN, F, Cl, Br and I;
$L^1$ is selected from the group consisting of $(CR^6R^7)_q$, $(CR^6R^7)_s$—S(O)$_2$—$(CR^6R^7)_r$, $(CR^6R^7)_s$—C(O)$NR^{6A}$—$(CR^6R^7)_r$, and $(CR^6R^7)_s$—$S(O)_2NR^{6A}$—$(CR^6R^7)_r$;
$Y^2$ is $C_{8-14}$ cycloalkyl, or $C_{8-14}$ heterocycloalkyl; wherein $Y^2$ is optionally substituted with one, two, or three substituents independently selected from the group consisting of $R^8$, $OR^8$, $SO_2R^8$, $CO(O)R^8$, OH, F, Cl, Br and I;
$Z^1$ is selected from the group consisting of

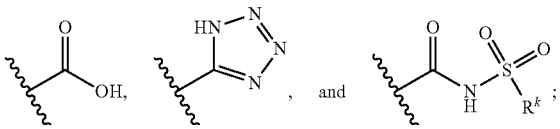

$R^2$, at each occurrence, is independently $C_{1-6}$ alkyl;
$R^5$, at each occurrence, is independently $C_{1-6}$ alkyl;
$R^{6A}$ is independently selected from the group consisting of hydrogen and $C_{1-6}$ alkyl;
$R^6$ and $R^7$, at each occurrence, are each independently hydrogen;
$R^8$, at each occurrence, is independently selected from the group consisting of $C_{1-6}$ alkyl and heterocyclyl; wherein the R⁸C₁₋₆ alkyl is optionally substituted with one substituent independently selected from the group consisting of R¹⁶, OR¹⁶, SO₂R¹⁶, and NHR¹⁶;

R^k, at each occurrence, is independently selected from the group consisting of C₁₋₆ alkyl, C₃₋₇ heterocycloalkyl, C₃₋₇ cycloalkyl and C₁₋₆ haloalkyl;

R¹⁶, at each occurrence, is independently selected from the group consisting of C₁₋₄ alkyl, aryl, and heterocycloalkyl; wherein the R¹⁶C₁₋₄ alkyl is optionally substituted with one substituent independently selected from the group consisting of OCH₃, OCH₂CH₂OCH₃, and OCH₂CH₂NHCH₃;

q is 1 or 2;
s is 0;
r is 0 or 1;
wherein the sum of s and r is 0 or 1;
m is 0;
n is 0, 1, or 2;
o is 0, 1, or 2; and
p is 0.

Still another embodiment pertains to a compound having Formula (III) selected from the group consisting of 6-[8-(1,3-benzothiazol-2-ylcarbamoyl)-3,4-dihydroisoquinolin-2(1H)-yl]-3-{1-[tricyclo[3.3.1.1³,⁷]dec-1-ylmethyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[3,5-dimethyl-1-(tricyclo[3.3.1.1³,⁷]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyltricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-hydroxytricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-methoxytricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3,5,7-trimethyltricyclo[3.3.1.1³,⁷]dec-1-yl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(tricyclo[3.3.1.1³,⁷]dec-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-bromotricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(propan-2-yloxy)tricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-oxatricyclo[3.3.1.1³,⁷]dec-1-ylmethyl)-1H-pyrazol-4-yl]pyridine-2-carboxylic acid;

6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(morpholin-4-yl)tricyclo[3.3.1.1³,⁷]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-methoxytricyclo[3.3.1.1³,⁷]dec-1-yl]methyl}-5-methyl-1H-pyrazol-4-yl)pyridine-2-carboxylic acid;

N-(1,3-benzothiazol-2-yl)-2-{6-[(methylsulfonyl)carbamoyl]-5-[5-methyl-1-(tricyclo[3.3.1.1³,⁷]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{6-[(cyclopropylsulfonyl)carbamoyl]-5-[5-methyl-1-(tricyclo[3.3.1.1³,⁷]dec-1-ylmethyl)-1H-pyrazol-4-yl]pyridin-2-yl}-1,2,3,4-tetrahydroisoquinoline-8-carboxamide;

N-(1,3-benzothiazol-2-yl)-2-{5-[5-methyl-1-(tricyclo[3.3.1.1³,⁷]dec-1-ylmethyl)-1H-pyrazol-4-yl]-6-(2H-tetrazol-5-yl)pyridin-2-yl}-1,2,3,4-tetrahydroisoquinoline-8-carboxamide;

3-[5-methyl-1-(tricyclo[3.3.1.1³,⁷]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-[1-({3-[2-(morpholin-4-yl)ethoxy]tricyclo[3.3.1.1³,⁷]dec-1-yl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{5-cyano-1-[tricyclo[3.3.1.1³,⁷]dec-1-ylmethyl]-1H-pyrazol-4-yl}pyridine-2-carboxylic acid;

3-[5-methyl-1-(tricyclo[3.3.1.1³,⁷]dec-1-ylmethyl)-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylic acid;

3-[5-methyl-1-(tricyclo[3.3.1.1³,⁷]dec-1-ylmethyl)-1H-pyrazol-4-yl]-6-[8-([1,3]thiazolo[4,5-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyltricyclo[3.3.1.1³,⁷]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(1,1-dioxidothiomorpholin-4-yl)tricyclo[3.3.1.1³,⁷]dec-1-yl]methyl}-1H-pyrazol-4-yl)pyridine-2-carboxylic acid;

N-(1,3-benzothiazol-2-yl)-2-{5-(1-{[3-methoxytricyclo[3.3.1.1³,⁷]dec-1-yl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-(1-{[3-methoxy-5,7-dimethyltricyclo[3.3.1.1³,⁷]dec-1-yl]methyl}-5-methyl-1H-pyrazol-4-yl)pyridine-2-carboxylic acid;

N-(1,3-benzothiazol-2-yl)-2-{5-(1-{[3-methoxytricyclo[3.3.1.1³,⁷]dec-1-yl]methyl}-5-methyl-1H-pyrazol-4-yl)-6-[(morpholin-4-ylsulfonyl)carbamoyl]pyridin-2-yl}-1,2,3,4-tetrahydroisoquinoline-8-carboxamide;

N-(1,3-benzothiazol-2-yl)-2-[5-(1-{[3-methoxytricyclo[3.3.1.1$^{3,7}$]dec-1-yl]methyl}-5-methyl-1H-pyrazol-4-yl)-6-{[(trifluoromethyl)sulfonyl]carbamoyl}pyridin-2-yl]-1,2,3,4-tetrahydroisoquinoline-8-carboxamide;

N-(1,3-benzothiazol-2-yl)-2-{6-[(cyclopropylsulfonyl)carbamoyl]-5-(1-{[3-methoxytricyclo[3.3.1.1$^{3,7}$]dec-1-yl]methyl}-5-methyl-1H-pyrazol-4-yl)pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid;

6-[8-(1,3-benzothiazol-2-ylcarbamoyl)-1-methyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)(1,1-$^2$H$_2$)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclooctyl]methyl}-5-methyl-1H-pyrazol-4-yl)pyridine-2-carboxylic acid;

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[2-(2-methoxyethyl)tricyclo[3.3.1.1$^{3,7}$]dec-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid;

3-[5-methyl-1-(2-oxatricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-N-([1,3]thiazolo[5,4-b]pyridin-2-yl)-1,2,3,4-tetrahydroisoquinoline-8-carboxamide;

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid;

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-methyl-1-{[3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl})-5-methyl-1H-pyrazol-4-yl)pyridine-2-carboxylic acid; and therapeutically acceptable salts, metabolites, prodrugs, salts of metabolites, and salts of prodrugs thereof.

In another aspect, the present invention provides compounds of Formula (IV)

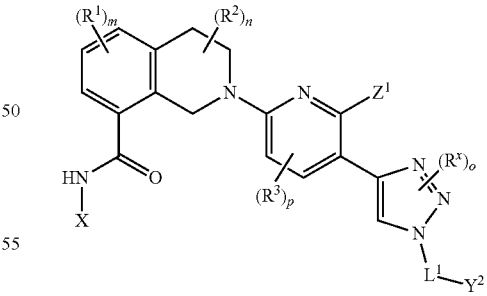

Formula (IV)

and therapeutically acceptable salts, metabolites, prodrugs, salts of metabolites, and salts of prodrugs thereof, wherein X, L$^1$, Y$^2$, Z$^1$, R$^1$, R$^2$, R$^3$, m, n, and p are as described herein for Formula (I); R$^x$ is as described herein for substituents on Y$^1$, and o is 0 or 1.

One embodiment of this invention pertains to compounds, and therapeutically acceptable salts thereof, which are useful as inhibitors of anti-apoptotic Bcl-xL proteins, the compounds having Formula (IV)

Formula (IV)

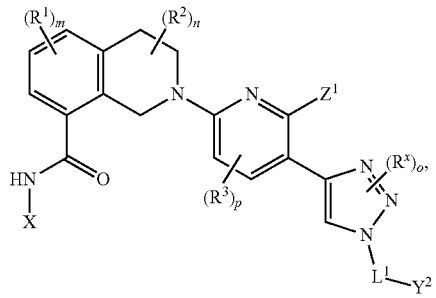

wherein

X is heteroaryl; wherein the heteroaryl represented by X is optionally substituted with one, two, three, or four $R^4$;

$R^x$ is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)_2—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)_2$NR^{6A}$—$(CR^6R^7)_r$, and $(CR^6R^7)_s$—$NR^{6A}S(O)_2$—$(CR^6R^7)_r$;

$Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

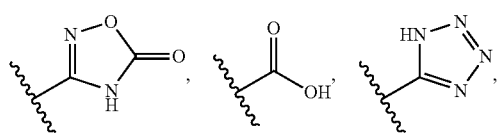

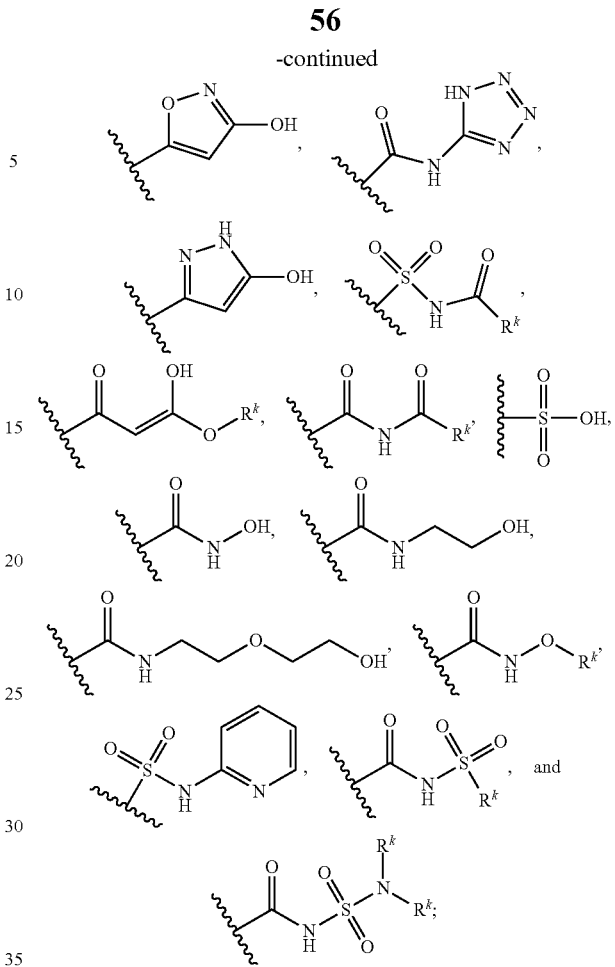

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, $CN$, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N$ $(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, $OH$, $CN$, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8 C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, $OH$, $CN$, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, $(O)$, $OH$, $CN$, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $O-(C_{1-4}$ alkyl), $NH_2$, $C(O)NH_2$, $SO_2NH_2$, $C(O)H$, $C(O)OH$, $(O)$, $OH$, $CN$, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;

s is 0, 1, 2, or 3;

r is 0, 1, 2, or 3;

wherein the sum of s and r is 0, 1, or 2;

m is 0, 1, 2, or 3;

n is 0, 1, 2, 3, 4, 5, or 6;

o is 0 or 1; and p is 0, 1, or 2.

In one embodiment of Formula (IV), m is 0, 1, 2, or 3; n is 0, 1, 2, 3, 4, 5, or 6; and p is 0, 1, or 2. In another embodiment of Formula (IV), n is 0, 1, or 2. In another embodiment of Formula (IV), n is 0, 1, or 2; and each $R^2$ is independently deuterium or $C_{1-6}$ alkyl. In another embodiment of Formula (IV), m, n, and p are 0.

In one embodiment of Formula (IV), X is heteroaryl, which is optionally substituted with one, two, three or four $R^4$. In another embodiment of Formula (IV), X is heteroaryl, which is unsubstituted. In another embodiment of Formula (IV), X is heteroaryl, which is substituted with one $R^4$. In another embodiment of Formula (IV), X is heteroaryl, which is substituted with two $R^4$. In another embodiment of Formula (IV), X is heteroaryl, which is substituted with one $R^4$, and $R^4$ is $OR^{12}$ or halogen. In another embodiment of Formula (IV), X is heteroaryl, which is substituted with two $R^4$, and each $R^4$ is independently $OR^{12}$ or halogen. In another embodiment of Formula (IV), X is heteroaryl, which is substituted with one $R^4$, and $R^4$ is Cl, F, or methoxy. In another embodiment of Formula (IV), X is heteroaryl, which is substituted with two $R^4$, and each $R^4$ is independently F.

In one embodiment of Formula (IV), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (IV), X is benzo[d]thiazolyl, which is optionally substituted with one, two, three or four $R^4$. In another embodiment of Formula (IV), X is benzo[d]thiazolyl, which is unsubstituted. In another embodiment of Formula (IV), X is benzo[d]thiazolyl, which is substituted with one $R^4$. In another embodiment of Formula (IV), X is benzo[d]thiazolyl, which is substituted with two $R^4$. In another embodiment of Formula (IV), X is benzo[d]thiazolyl, which is substituted with one $R^4$, and $R^4$ is $OR^{12}$ or halogen. In another embodiment of Formula (IV), X is benzo[d]thiazolyl, which is substituted with two $R^4$, and each $R^4$ is independently $OR^{12}$ or halogen. In another embodiment of Formula (IV), X is benzo[d]thiazolyl, which is substituted with one $R^4$, and $R^4$ is Cl, F, or methoxy. In another embodiment of Formula (IV), X is benzo[d]thiazolyl, which is substituted with two $R^4$, and each $R^4$ is independently F.

In one embodiment of Formula (IV), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

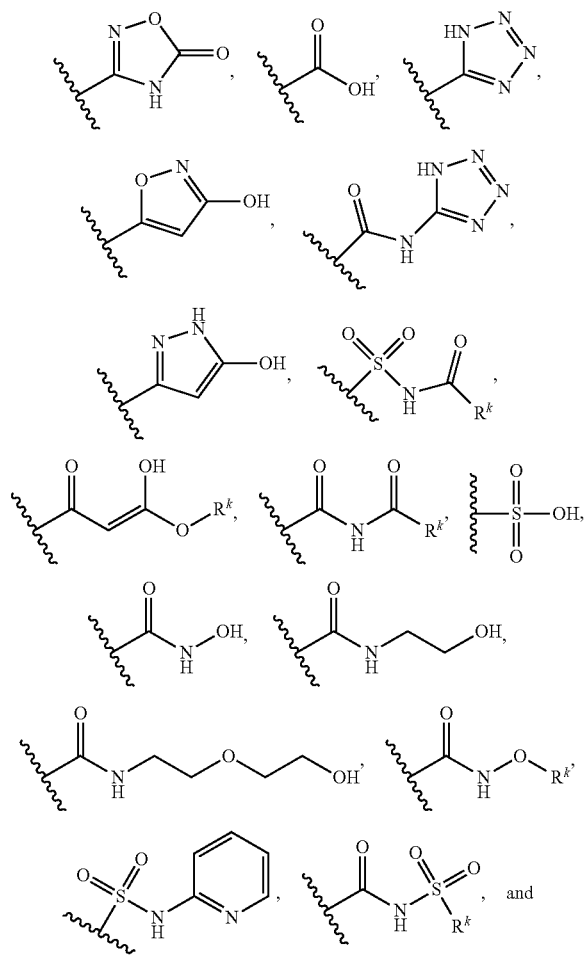

In another embodiment of Formula (IV), $Z^1$ is

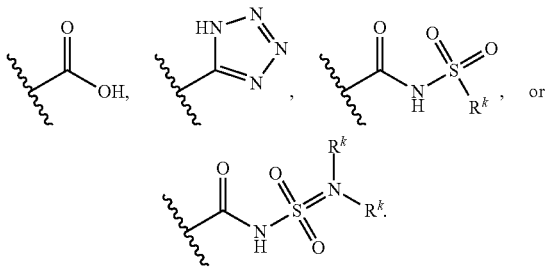

In another embodiment of Formula (IV), $Z^1$ is

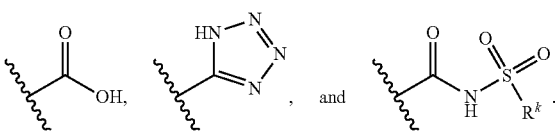

In another embodiment of Formula (IV), $Z^1$ is

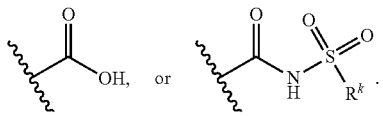

In another embodiment of Formula (IV), $Z^1$ is

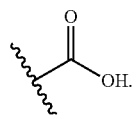

In one embodiment of Formula (IV), o is 0. In another embodiment of Formula (IV), o is 0 or 1. In another embodiment of Formula (IV), o is 1; and $R^x$ is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, OH, CN, $N_5$, $NO_2$, F, Cl, Br and I. In another embodiment of Formula (IV), o is 1; and $R^x$ is independently selected from the group consisting of $R^5$, CN, F, Cl, Br and I. In another embodiment of Formula (IV), o is 1; and $R^x$ is independently selected from the group consisting of $R^5$, CN, F, Cl, Br and I; wherein $R^5$ is $C_{1-6}$ alkyl. In another embodiment of Formula (IV), o is 1; $R^x$ is $R^5$, Cl, or CN; and $R^5$ is $CH_3$. In another embodiment of Formula (IV), o is 1; and $R^x$ is CN. In another embodiment of Formula (IV), o is 1; and $R^x$ is Cl. In another embodiment of Formula (IV), o is 1; $R^x$ is $R^5$; and $R^5$ is $CH_3$.

In one embodiment of Formula (IV), $L^1$ is selected from the group consisting of $(CR^6R^7)_q$, $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—$C(O)NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^6R^7)_r$; and $Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I.

In another embodiment of Formula (IV), $L^1$ is $(CR^6R^7)_q$; and $Y^2$ is selected from the group consisting of $C_{8-14}$ cycloalkyl and $C_{8-14}$ heterocycloalkyl; wherein $R^6$ and $R^7$, at each occurrence, are hydrogen; and q is 1 or 2. In another embodiment of Formula (IV), $L^1$ is selected from the group consisting of $(CR^6R^7)_s$—$S(O)_2$—$(CR^6R^7)_r$, $(CR^6R^7)_s$—$C(O)NR^{6A}$—$(CR^6R^7)_r$, and $(CR^6R^7)_s$—$S(O)_2NR^{6A}$—$(CR^6R^7)_r$; $Y^2$ is selected from the group consisting of $C_{8-14}$ cycloalkyl, and $C_{8-14}$ heterocycloalkyl; s is 0; r is 0 or 1; $R^{6A}$ is independently selected from the group consisting of hydrogen and $C_{1-6}$ alkyl; and $R^6$ and $R^7$, at each occurrence, are hydrogen.

In another embodiment of Formula (IV),

X is heteroaryl;

$R^x$ is independently selected from the group consisting of $R^5$, CN, F, Cl, Br and I;

$L^1$ is selected from the group consisting of $(CR^6R^7)_q$, $(CR^6R^7)_s$—$S(O)_2$—$(CR^6R^7)_r$, $(CR^6R^7)_s$—$C(O)NR^{6A}$—$(CR^6R^7)_r$, and $(CR^6R^7)_s$—$S(O)_2NR^{6A}$—$(CR^6R^7)_r$;

$Y^2$ is $C_{8-14}$ cycloalkyl or $C_{8-14}$ heterocycloalkyl; wherein $Y^2$ is optionally substituted with one, two, or three substituents independently selected from the group consisting of $R^8$, $OR^8$, $SO_2R^8$, $CO(O)R^8$, OH, F, Cl, Br and I;

$Z^1$ is selected from the group consisting of $R^2$, at each occurrence, is independently $C_{1-6}$ alkyl;

$R^5$, at each occurrence, is independently $C_{1-6}$ alkyl;

$R^{6A}$ is independently selected from the group consisting of hydrogen and $C_{1-6}$ alkyl;

$R^6$ and $R^7$, at each occurrence, are each independently hydrogen;

$R^8$, at each occurrence, is independently selected from the group consisting of $C_{1-6}$ alkyl and heterocyclyl; wherein the $R^8C_{1-6}$ alkyl is optionally substituted with one substituent independently selected from the group consisting of $R^{16}$, $OR^{16}$, $SO_2R^{16}$, and $NHR^{16}$;

$R^k$, at each occurrence, is independently selected from the group consisting of $C_{1-6}$ alkyl, $C_{3-7}$ heterocycloalkyl, $C_{3-7}$ cycloalkyl and $C_{1-6}$ haloalkyl;

$R^{16}$, at each occurrence, is independently selected from the group consisting of $C_{1-4}$ alkyl, aryl, and heterocycloalkyl; wherein the $R^{16}C_{1-4}$ alkyl is optionally substituted with one substituent independently selected from the group consisting of $OCH_3$, $OCH_2CH_2OCH_3$, and $OCH_2CH_2NHCH_3$;

q is 1 or 2;

s is 0;

r is 0 or 1;

wherein the sum of s and r is 0 or 1;

m is 0;

n is 0, 1, or 2;

o is 0 or 1; and p is 0.

Still another embodiment pertains to a compound having Formula (IV) selected from the group consisting of 6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-1,2,3-triazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-1,2,3-triazol-4-yl]pyridine-2-carboxylic acid; and therapeutically acceptable salts, metabolites, prodrugs, salts of metabolites, and salts of prodrugs thereof.

In another aspect, the present invention provides compounds of Formula (V)

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); $R^x$ is as described herein for substituents on $Y^1$, and o is 0, 1, 2, 3, or 4.

One embodiment of this invention pertains to compounds, and therapeutically acceptable salts thereof, which are useful as inhibitors of anti-apoptotic Bcl-xL proteins, the compounds having Formula (V)

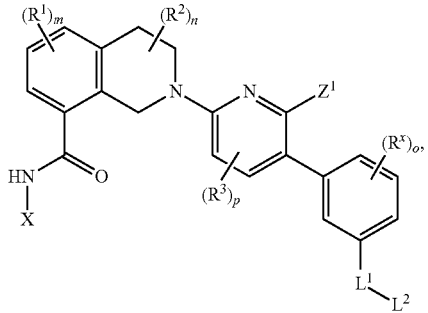

Formula (V)

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)_2—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)_2$NR^{6A}$—$(CR^6R^7)_r$, and $(CR^6R^7)_s$—$NR^{6A}S(O)_2$—$(CR^6R^7)_r$;

$Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

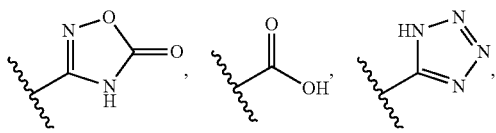

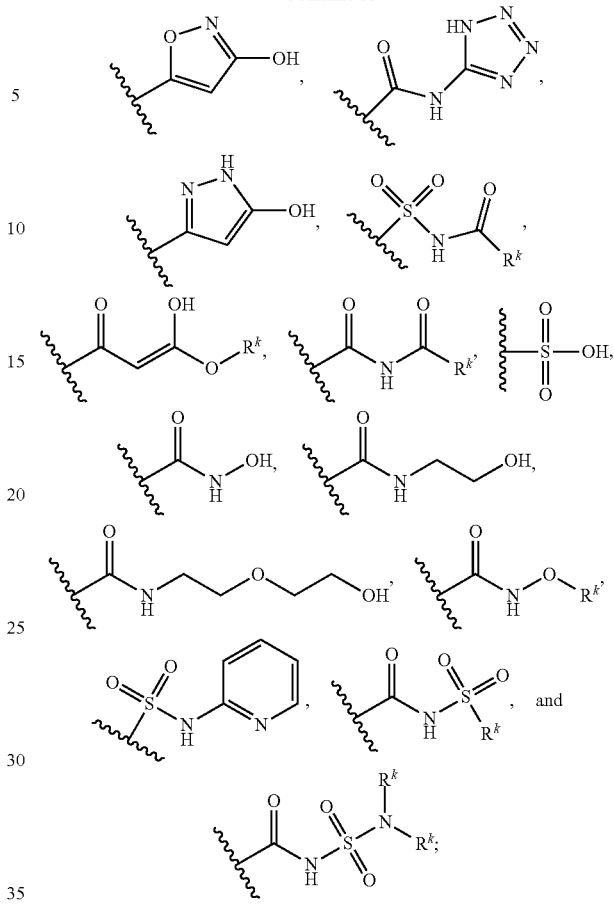

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, $CN$, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^5$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, CO(O)H, C(O)H, OH, CN, N$_3$, NO$_2$, F, Cl, Br and I;

R$^8$, at each occurrence, is independently selected from the group consisting of C$_{1-6}$ alkyl, C$_{2-6}$ alkenyl, C$_{2-6}$ alkynyl, C$_{1-6}$ haloalkyl, aryl, heterocyclyl, cycloalkyl, and cycloalkenyl; wherein the R$^8$C$_{1-6}$ alkyl, C$_{2-6}$ alkenyl, C$_{2-6}$ alkynyl, and C$_{1-6}$ haloalkyl are optionally substituted with one, two, three, four, five, or six substituents independently selected from the group consisting of R$^{16}$, OR$^{16}$, SR$^{16}$, S(O)R$^{16}$, SO$_2$R$^{16}$, C(O)R$^{16}$, CO(O)R$^{16}$, C(O)R$^{16}$, OC(O)OR$^{16}$, NH$_2$, NHR$^{16}$, N(R$^{16}$)$_2$, NHC(O)R$^{16}$, NR$^{16}$C(O)R$^{16}$, NHS(O)$_2$R$^{16}$, NR$^{16}$S(O)$_2$R$^{16}$, NHC(O)OR$^{16}$, NR$^{16}$C(O)OR$^{16}$, NHC(O)NH$_2$, NHC(O)NHR$^{16}$, NHC(O)N(R$^{16}$)$_2$, NR$^{16}$C(O)NHR$^{16}$, NR$^{16}$C(O)N(R$^{16}$)$_2$, C(O)NH$_2$, C(O)NHR$^{16}$, C(O)N(R$^{16}$)$_2$, C(O)NHOH, C(O)NHOR$^{16}$, C(O)NHSO$_2$R$^{16}$, C(O)NR$^{16}$SO$_2$R$^{16}$, SO$_2$NH$_2$, SO$_2$NHR$^{16}$, SO$_2$N(R$^{16}$)$_2$, CO(O)H, C(O)H, OH, CN, N$_3$, NO$_2$, F, Cl, Br and I; wherein the R$^8$ aryl, heterocyclyl, cycloalkyl, and cycloalkenyl are optionally substituted with one, two, or three substituents independently selected from the group consisting of C$_{1-6}$ alkyl, C$_{2-6}$ alkenyl, C$_{2-6}$ alkynyl, C$_{1-6}$ haloalkyl, NH$_2$, C(O)NH$_2$, SO$_2$NH$_2$, C(O)H, (O), OH, CN, NO$_2$, OCF$_3$, OCF$_2$CF$_3$, F, Cl, Br and I;

R$^9$ is selected from the group consisting of C$_{1-6}$ alkyl, C$_{2-6}$ alkenyl, C$_{2-6}$ alkynyl, C$_{1-6}$ haloalkyl, cycloalkyl, phenyl and (CH$_2$)$_{1-4}$ phenyl; and R$^{10}$ and R$^{11}$, at each occurrence, are each independently selected from the group consisting of hydrogen, C$_{1-6}$ alkyl, C$_{2-6}$ alkenyl, C$_{2-6}$ alkynyl, C$_{3-6}$ cycloalkyl, C$_{1-6}$ haloalkyl, phenyl and (CH$_2$)$_{1-4}$-phenyl; or R$^{10}$ and R$^{11}$, or R$^{10}$ and R$^9$, together with the atom to which each is attached are combined to form a heterocyclyl;

R$^k$, at each occurrence, is independently selected from the group consisting of C$_{1-6}$ alkyl, C$_{2-6}$ alkenyl, C$_{2-6}$ alkynyl, C$_{3-7}$ heterocycloalkyl, C$_{3-7}$ cycloalkyl and C$_{1-6}$ haloalkyl;

R$^{12}$ and R$^{13}$, at each occurrence, are each independently selected from the group consisting of hydrogen, C$_{1-4}$ alkyl, C$_{2-4}$ alkenyl, C$_{2-4}$ alkynyl, C$_{1-4}$ haloalkyl and (CH$_2$)$_{1-4}$ phenyl;

R$^{14}$, at each occurrence, is independently selected from the group consisting of C$_{1-4}$ alkyl, C$_{2-4}$ alkenyl, C$_{2-4}$ alkynyl and C$_{1-4}$ haloalkyl;

R$^{12}$ and R$^{13}$, or R$^{12}$ and R$^{14}$, at each occurrence, together with the atom to which each is attached, are optionally combined to form a heterocyclyl;

R$^{15}$, at each occurrence, is independently selected from the group consisting of C$_{1-4}$ alkyl, C$_{2-4}$ alkenyl, C$_{2-4}$ alkynyl, C$_{1-4}$ haloalkyl, C$_{1-4}$ hydroxyalkyl, aryl, heterocyclyl, cycloalkyl, and cycloalkenyl; wherein the R$^{15}$C$_{1-4}$ alkyl, C$_{2-4}$ alkenyl, C$_{2-4}$ alkynyl, C$_{1-4}$ haloalkyl, and C$_{1-4}$ hydroxyalkyl are optionally substituted with one, two, or three substituents independently selected from the group consisting of O—(C$_{1-4}$ alkyl), NH$_2$, C(O)NH$_2$, SO$_2$NH$_2$, C(O)H, C(O)OH, (O), OH, CN, NO$_2$, OCF$_3$, OCF$_2$CF$_3$, F, Cl, Br and I;

R$^{16}$, at each occurrence, is independently selected from the group consisting of C$_{1-4}$ alkyl, C$_{2-4}$ alkenyl, C$_{2-4}$ alkynyl, C$_{1-4}$ haloalkyl, C$_{1-4}$ hydroxyalkyl, aryl, heterocycloalkyl, heterocycloalkenyl, heteroaryl, cycloalkyl, and cycloalkenyl; wherein the R$^{16}$C$_{1-4}$ alkyl, C$_{2-4}$ alkenyl, C$_{2-4}$ alkynyl, C$_{1-4}$ haloalkyl, and C$_{1-4}$ hydroxyalkyl are optionally substituted with one substituent independently selected from the group consisting of OCH$_3$, OCH$_2$CH$_2$OCH$_3$, and OCH$_2$CH$_2$NHCH$_3$;

q is 1, 2, or 3;
s is 0, 1, 2, or 3;
r is 0, 1, 2, or 3;

wherein the sum of s and r is 0, 1, or 2;
m is 0, 1, 2, or 3;
n is 0, 1, 2, 3, 4, 5, or 6;
o is 0, 1, 2, 3, or 4; and
p is 0, 1, or 2.

In one embodiment of Formula (V), m is 0, 1, 2, or 3; n is 0, 1, 2, 3, 4, 5, or 6; and p is 0, 1, or 2. In another embodiment of Formula (V), n is 0, 1, or 2. In another embodiment of Formula (V), n is 0, 1, or 2; and each R$^2$ is independently deuterium or C$_{1-6}$ alkyl. In another embodiment of Formula (V), m, n, and p are 0.

In one embodiment of Formula (V), X is heteroaryl, which is optionally substituted with one, two, three or four R$^4$. In another embodiment of Formula (V), X is heteroaryl, which is unsubstituted. In another embodiment of Formula (V), X is heteroaryl, which is substituted with one R$^4$. In another embodiment of Formula (V), X is heteroaryl, which is substituted with two R$^4$. In another embodiment of Formula (V), X is heteroaryl, which is substituted with one R$^4$, and R$^4$ is OR$^{12}$ or halogen. In another embodiment of Formula (V), X is heteroaryl, which is substituted with two R$^4$, and each R$^4$ is independently OR$^{12}$ or halogen. In another embodiment of Formula (V), X is heteroaryl, which is substituted with one R$^4$, and R$^4$ is Cl, F, or methoxy. In another embodiment of Formula (V), X is heteroaryl, which is substituted with two R$^4$, and each R$^4$ is independently F.

In one embodiment of Formula (V), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four R$^4$. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$, and R$^4$ is OR$^{12}$ or halogen. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$, and each R$^4$ is independently OR$^{12}$ or halogen. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$, and R$^4$ is Cl, F, or methoxy. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$, and each R$^4$ is independently F.

In one embodiment of Formula (V), X is benzo[d]thiazolyl, which is optionally substituted with one, two, three or four $R^4$. In another embodiment of Formula (V), X is benzo[d]thiazolyl, which is unsubstituted. In another embodiment of Formula (V), X is benzo[d]thiazolyl, which is substituted with one $R^4$. In another embodiment of Formula (V), X is benzo[d]thiazolyl, which is substituted with two $R^4$. In another embodiment of Formula (V), X is benzo[d]thiazolyl, which is substituted with one $R^4$, and $R^4$ is $OR^{12}$ or halogen. In another embodiment of Formula (V), X is benzo[d]thiazolyl, which is substituted with two $R^4$, and each $R^4$ is independently $OR^{12}$ or halogen. In another embodiment of Formula (V), X is benzo[d]thiazolyl, which is substituted with one $R^4$, and $R^4$ is Cl, F, or methoxy. In another embodiment of Formula (V), X is benzo[d]thiazolyl, which is substituted with two $R^4$, and each $R^4$ is independently F.

In one embodiment of Formula (V), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

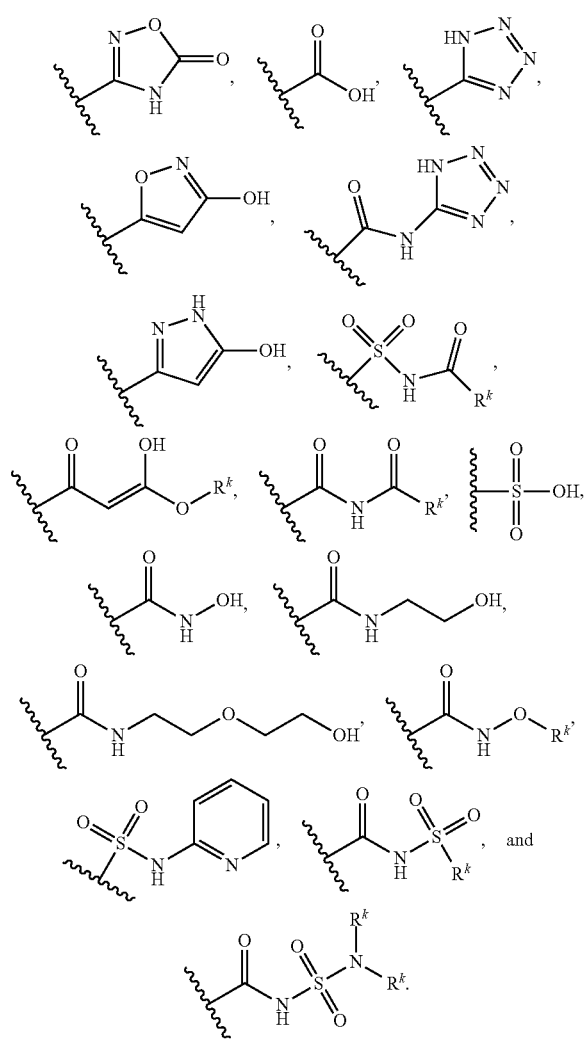

In another embodiment of Formula (V), $Z^1$ is

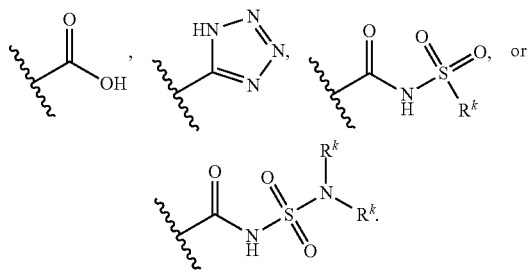

In another embodiment of Formula (V), Z is

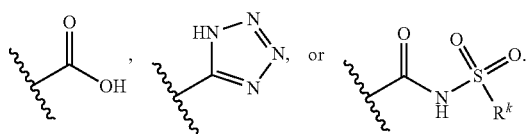

In another embodiment of Formula (V), $Z^1$ is

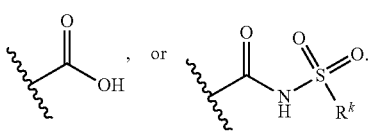

In another embodiment of Formula (V), $Z^1$ is

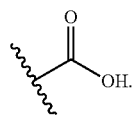

In one embodiment of Formula (V), o is 0. In another embodiment of Formula (V), o is 0, 1, 2, 3, or 4. In another embodiment of Formula (V), o is 1, 2, 3, or 4; and $R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, OH, CN, $N_5$, $NO_2$, F, Cl, Br and I. In another embodiment of Formula (V), o is 1, 2, 3, or 4; and $R^x$, at each occurrence, is independently selected from the group consisting of $R^5$, CN, F, Cl, Br and I. In another embodiment of Formula (V), o is 1, 2, 3, or 4; and $R^x$, at each occurrence, is independently selected from the group consisting of $R^5$, CN, F, Cl, Br and I; wherein $R^5$ is $C_{1-6}$ alkyl. In another embodiment of Formula (V), o is 1 or 2; $R^x$ is $R^5$ or CN; and $R^5$ is $CH_3$. In another embodiment of Formula (V), o is 1; and $R^x$ is CN. In another embodiment of Formula (V), o is 1; and $R^x$ is Cl. In another embodiment of Formula (V), o is 1; $R^x$ is $R^5$; and $R^5$ is $CH_3$.

In one embodiment of Formula (V), $L^1$ is selected from the group consisting of $(CR^6R^7)_q$, $(CR^6R^7)_q$, $(CR^6R^7)_s$—O—

$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, $(CR^6R^7)_s$—S(O)$_2$NR$^{6A}$—$(CR^6R^7)_r$, and $(CR^6R^7)_s$—NR$^{6A}$S(O)$_2$—$(CR^6R^7)_r$; and Y$^2$ is C$_{8-14}$ cycloalkyl, C$_{8-14}$ cycloalkenyl, C$_{8-14}$ heterocycloalkyl, or C$_{8-14}$ heterocycloalkenyl; optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^2$ is optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I.

In another embodiment of Formula (V), L$^1$ is $(CR^6R^7)_q$; and Y$^2$ is selected from the group consisting of C$_{8-14}$ cycloalkyl, and C$_{8-14}$ heterocycloalkyl; wherein R$^6$ and R$^7$, at each occurrence, are hydrogen; and q is 1 or 2. In another embodiment of Formula (V), L$^1$ is selected from the group consisting of $(CR^6R^7)_s$—O—$(CR^6R^7)_r$, $(CR^6R^7)_s$—$(CR^6R^7)_r$, $(CR^6R^7)_s$—S(O)$_2$—$(CR^6R^7)_r$, $(CR^6R^7)_s$—NR$^{6A}$—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, and $(CR^6R^7)_s$—S(O)$_2$NR$^{6A}$—$(CR^6R^7)_r$; Y$^2$ is selected from the group consisting of C$_{8-14}$ cycloalkyl, and C$_{8-14}$ heterocycloalkyl; s is 0; r is 0 or 1; R$^{6A}$ is independently selected from the group consisting of hydrogen, and C$_{1-6}$ alkyl; and R$^6$ and R$^7$, at each occurrence, are hydrogen.

In another embodiment of Formula (V),

X is heteroaryl;

R$^x$, at each occurrence, is independently selected from the group consisting of R$^5$, CN, F, Cl, Br and I;

L$^1$ is selected from the group consisting of $(CR^6R^7)_q$, $(CR^6R^7)_s$—O—$(CR^6R^7)_r$, $(CR^6R^7)_s$—S—$(CR^6R^7)_r$, $(CR^6R^7))_s$—S(O)$_2$—$(CR^6R^7)_r$, $(CR^6R^7)_s$NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, and $(CR^6R^7)_s$—S(O)$_2$NR$^{6A}$—$(CR^6R^7)_r$;

Y$^2$ is C$_{8-14}$ cycloalkyl, or C$_{8-14}$ heterocycloalkyl; wherein Y$^2$ is optionally substituted with one, two, or three substituents independently selected from the group consisting of R$^8$, OR$^8$, SO$_2$R$^8$, CO(O)R$^8$, OH, F, Cl, Br and I;

Z$^1$ is selected from the group consisting of

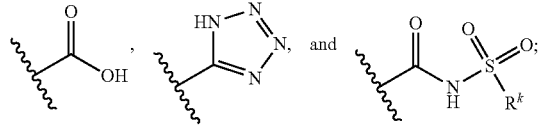

R$^2$, at each occurrence, is independently C$_{1-6}$ alkyl;

R$^5$, at each occurrence, is independently C$_{1-6}$ alkyl;

R$^{6A}$ is independently selected from the group consisting of hydrogen and C$_{1-6}$ alkyl;

R$^6$ and R$^7$, at each occurrence, are each independently hydrogen;

R$^8$, at each occurrence, is independently selected from the group consisting of C$_{1-6}$ alkyl and heterocyclyl; wherein the R$^8$C$_{1-6}$ alkyl is optionally substituted with one substituent independently selected from the group consisting of R$^{16}$, OR$^{16}$, SO$_2$R$^{16}$, and NHR$^{16}$;

R$^k$, at each occurrence, is independently selected from the group consisting of C$_{1-6}$ alkyl, C$_{3-7}$ heterocycloalkyl, C$_{3-7}$ cycloalkyl and C$_{1-6}$ haloalkyl;

R$^{16}$, at each occurrence, is independently selected from the group consisting of C$_{1-4}$ alkyl, aryl, and heterocycloalkyl; wherein the R$^{16}$C$_{1-4}$ alkyl is optionally substituted with one substituent independently selected from the group consisting of OCH$_3$, OCH$_2$CH$_2$OCH$_3$, and OCH$_2$CH$_2$NHCH$_3$;

q is 1 or 2;

s is 0;

r is 0 or 1;

wherein the sum of s and r is 0 or 1;

m is O;

n is 0, 1, or 2;

o is 0 or 1; and p is 0.

Still another embodiment pertains to a compound having Formula (V) selected from the group consisting of 6-[8-(1,3-benzothiazol-2-ylcarbamoyl)-3,4-dihydroisoquinolin-2(1H)-yl]-3-{2-methyl-4-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylmethoxy]phenyl}pyridine-2-carboxylic acid;

6-[8-(1,3-benzothiazol-2-ylcarbamoyl)-3,4-dihydroisoquinolin-2(1H)-yl]-3-{3-[tricyclo[3.3.1.1$^{3,7}$]dec-1-ylmethoxy]phenyl})pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid;

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid;

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid;

6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid;

6-[8-(1,3-benzothiazol-2-ylcarbamoyl)-3,4-dihydroisoquinolin-2(1H)-yl]-3-(2-methyl-3-{methyl[(tricyclo[3.3.1.1$^{3,7}$]dec-2-yl]carbamoyl}phenyl)pyridine-2-carboxylic acid;

6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[tricyclo

[3.3.1.1$^{3,7}$]dec-2-yl]sulfamoyl}phenyl)pyridine-2-carboxylic acid; and therapeutically acceptable salts, metabolites, prodrugs, salts of metabolites, and salts of prodrugs thereof.

In another aspect, the present invention provides compounds of Formula (VI)

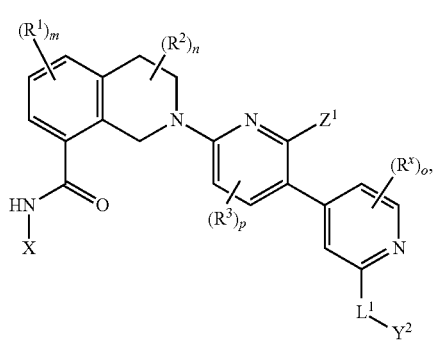

Formula (VI)

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); $R^x$ is as described herein for substituents on $Y^1$, and o is 0, 1, 2, or 3.

One embodiment of this invention pertains to compounds, and therapeutically acceptable salts thereof, which are useful as inhibitors of anti-apoptotic Bcl-xL proteins, the compounds having Formula (VI)

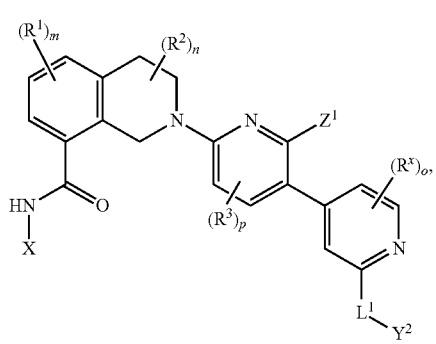

Formula (VI)

wherein
X is heteroaryl; wherein the heteroaryl represented by X is optionally substituted with one, two, three, or four $R^4$;
$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, $F$, $Cl$, $Br$ and $I$;
$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}$C(O)—$(CR^6R^7)_r$, $(CR^6R^7)_s$—C(O)$NR^{6A}$—$(CR^6R^7)_r$, $(CR^6R^7)_s$$NR^{6A}$—$(CR^6R^7)_r$, $(CR^6R^7)_s$—S(O)$_2$$NR^{6A}$$(CR^6R^7)_r$, and $(CR^6R^7)_s$—$NR^{6A}$S(O)$_2$—$(CR^6R^7)_r$;

$Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$;
$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or
$Z^1$ is selected from the group consisting of

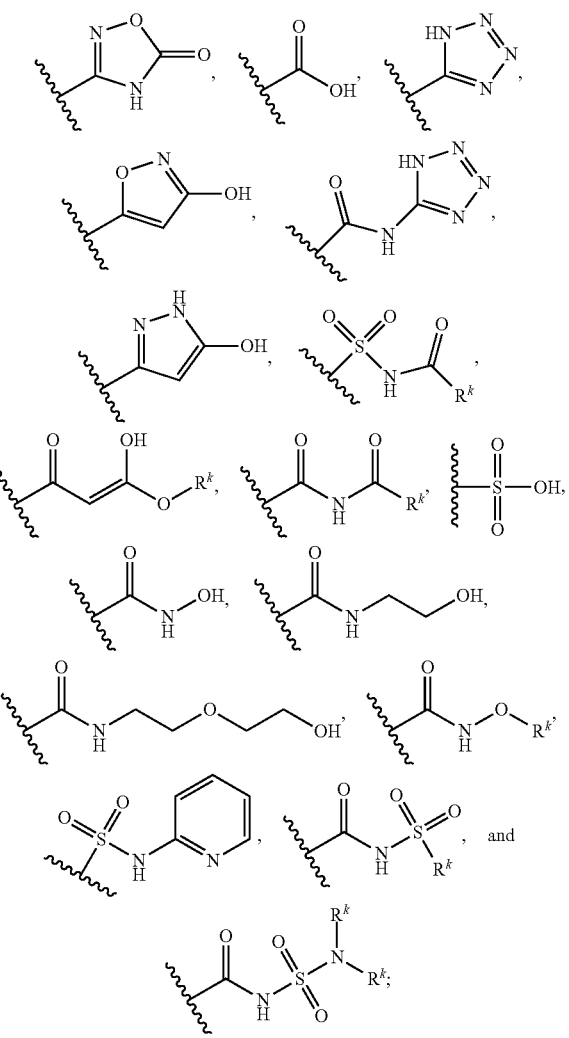

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $C(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of O—($C_{1-4}$ alkyl), $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;

s is 0, 1, 2, or 3;

r is 0, 1, 2, or 3;

wherein the sum of s and r is 0, 1, or 2;

m is 0, 1, 2, or 3;

n is 0, 1, 2, 3, 4, 5, or 6;

o is 0, 1, 2, or 3; and p is 0, 1, or 2.

In one embodiment of Formula (VI), m is 0, 1, 2, or 3; n is 0, 1, 2, 3, 4, 5, or 6; and p is 0, 1, or 2. In another embodiment of Formula (VI), n is 0, 1, or 2. In another embodiment of Formula (VI), n is 0, 1, or 2; and each $R^2$ is independently deuterium or $C_{1-6}$ alkyl. In another embodiment of Formula (VI), m, n, and p are 0.

In one embodiment of Formula (VI), X is heteroaryl, which is optionally substituted with one, two, three or four $R^4$. In another embodiment of Formula (VI), X is heteroaryl, which is unsubstituted. In another embodiment of Formula (VI), X is heteroaryl, which is substituted with one $R^4$. In another embodiment of Formula (VI), X is heteroaryl, which is substituted with two $R^4$. In another embodiment of Formula (VI), X is heteroaryl, which is substituted with one $R^4$, and $R^4$ is $OR^{12}$ or halogen. In another embodiment of Formula (VI), X is heteroaryl, which is substituted with two $R^4$, and each $R^4$ is independently $OR^{12}$ or halogen. In another embodiment of Formula (VI), X is heteroaryl, which is substituted with one $R^4$, and $R^4$ is Cl, F, or methoxy. In another embodiment of Formula (VI), X is heteroaryl, which is substituted with two $R^4$, and each $R^4$ is independently F.

In one embodiment of Formula (VI), X benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (VI), X is benzo[d]thiazolyl, which is optionally substituted with one, two, three or four $R^4$. In another embodiment of Formula (VI), X is benzo[d]thiazolyl, which is unsubstituted. In another embodiment of Formula (VI), X is benzo[d]thiazolyl, which is substituted with one $R^4$. In another embodiment of Formula (VI), X is benzo[d]thiazolyl, which is substituted with two $R^4$. In another embodiment of Formula (VI), X is benzo[d]thiazolyl, which is substituted with one $R^4$, and $R^4$ is $OR^{12}$ or halogen. In another embodiment of Formula (VI), X is benzo[d]thiazolyl, which is substituted with two $R^4$, and each $R^4$ is independently $OR^{12}$ or halogen. In another embodiment of Formula (VI), X is benzo[d]thiazolyl, which is substituted with one $R^4$, and $R^4$ is Cl, F, or methoxy. In another embodiment of Formula (VI), X is benzo[d]thiazolyl, which is substituted with two $R^4$, and each $R^4$ is independently F.

In one embodiment of Formula (VI), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

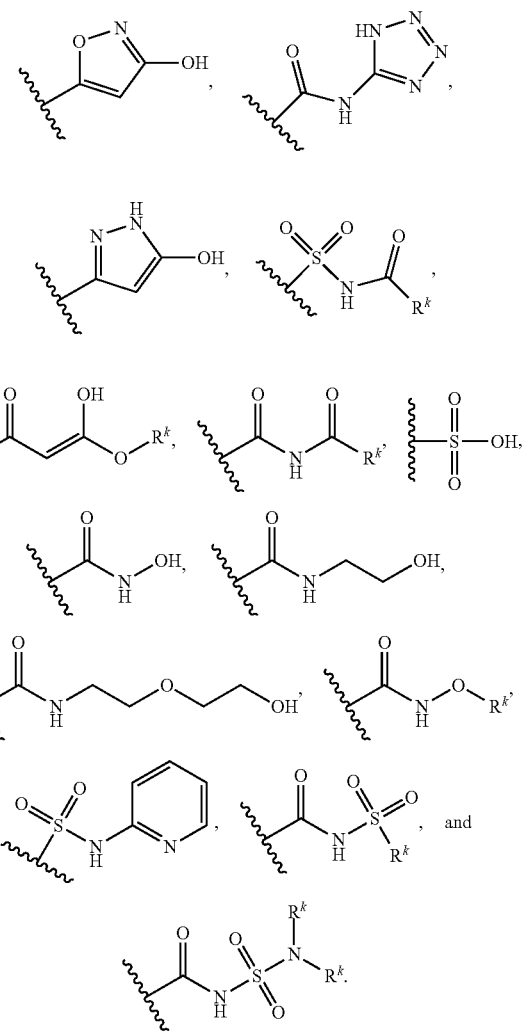

In another embodiment of Formula (VI), $Z^1$ is

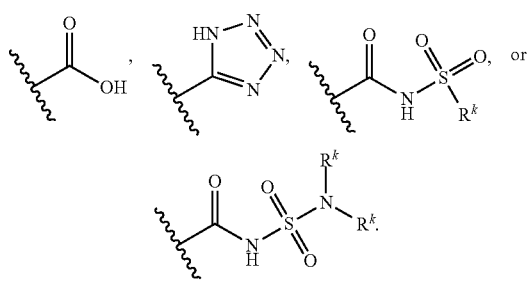

In another embodiment of Formula (VI), $Z^1$ is

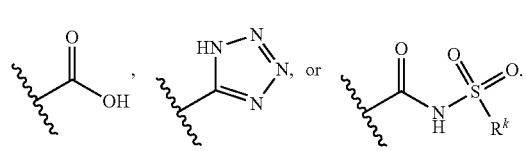

In another embodiment of Formula (VI), Z¹ is

[chemical structures: carboxylic acid and acylsulfonamide groups]

, or

In another embodiment of Formula (VI), Z¹¹ is

[chemical structure: carboxylic acid group]

In one embodiment of Formula (VI), o is 0. In another embodiment of Formula (VI), is 0, 1, 2, or 3. In another embodiment of Formula (VI), o is 1, 2, or 3; and $R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I. In another embodiment of Formula (VI), o is 1, 2, or 3; and $R^x$, at each occurrence, is independently selected from the group consisting of $R^5$, CN, F, Cl, Br and I. In another embodiment of Formula (VI), o is 1, 2, or 3; and $R^x$, at each occurrence, is independently selected from the group consisting of $R^5$, CN, F, Cl, Br and I; wherein $R^5$ is $C_{1-6}$ alkyl. In another embodiment of Formula (VI), o is 1 or 2; $R^x$ is $R^5$ or CN; and $R^5$ is $CH_3$. In another embodiment of Formula (VI), o is 1; and $R^x$ is CN. In another embodiment of Formula (VI), o is 1; and $R^x$ is Cl. In another embodiment of Formula (VI), o is 1; $R^x$ is $R^5$; and $R^5$ is $CH_3$.

In one embodiment of Formula (VI), L¹ is selected from the group consisting of $(CR^6R^7)_q$, $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)_2—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)_2$NR^{6A}$—$(CR^6R^7)_r$, and $(CR^6R^7)_s$—$NR^{6A}S(O)_2$—$(CR^6R^7)_r$; and $Y^2$ is $C_{8-14}$ cycloalkyl, $C_{8-14}$ cycloalkenyl, $C_{8-14}$ heterocycloalkyl, or $C_{8-14}$ heterocycloalkenyl; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I.

In another embodiment of Formula (VI), L¹ is $(CR^6R^7)_q$; and $Y^2$ is selected from the group consisting of $C_{8-14}$ cycloalkyl, and $C_{8-14}$ heterocycloalkyl; wherein $R^6$ and $R^7$, at each occurrence, are hydrogen; and q is 1 or 2. In another embodiment of Formula (VI), L¹ is selected from the group consisting of $(CR^6R^7)_s$—O—$(CR^6R^7)_r$, $(CR^6R^7)_s$—S—$(CR^6R^7)_r$, $(CR^6R^7)_s$—S(O)_2—$(CR^6R^7)_r$, $(CR^6R^7)_s$—$NR^{6A}C(O)$—$(CR^6R^7)_r$, $(CR^6R^7)_s$C(O)$NR^{6A}$—$(CR^6R^7)_r$, $(CR^6R^7)_s$—$NR^{6A}$—$(CR^6R^7)_r$, and $(CR^6R^7)_s$—S(O)_2$NR^{6A}$—$(CR^6R^7)_r$; $Y^2$ is selected from the group consisting of $C_{8-14}$ cycloalkyl, and $C_{8-14}$ heterocycloalkyl; s is 0; r is 0 or 1; $R^{6A}$ is independently selected from the group consisting of hydrogen, and $C_{1-6}$ alkyl; and $R^6$ and $R^7$, at each occurrence, are hydrogen.

In another embodiment of Formula (VI),
X is heteroaryl;
$R^x$, at each occurrence, is independently selected from the group consisting of $R^5$, CN, F, Cl, Br and I;
L¹ is selected from the group consisting of $(CR^6R^7)_q$, $(CR^6R^7)_s$—O—$(CR^6R^7)_r$, $(CR^6R^7)_s$—S—$(CR^6R^7)_r$, $(CR^6R^7)_s$—S(O)_2—$(CR^6R^7)_r$, $(CR^6R^7)_s$$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, and $(CR^6R^7)_s$—S(O)_2$NR^{6A}$—$(CR^6R^7)_r$;
$Y^2$ is $C_{8-14}$ cycloalkyl, or $C_{8-14}$ heterocycloalkyl; wherein $Y^2$ is optionally substituted with one, two, or three substituents independently selected from the group consisting of $R^8$, $OR^8$, $SO_2R^8$, $CO(O)R^8$, OH, F, Cl, Br and I;
Z¹ is selected from the group consisting of

[chemical structures: carboxylic acid, tetrazole, and acylsulfonamide groups]

, and $R^2$, at each occurrence, is independently $C_{1-6}$ alkyl;
$R^5$, at each occurrence, is independently $C_{1-6}$ alkyl;
$R^{6A}$ is independently selected from the group consisting of hydrogen and $C_{1-6}$ alkyl;
$R^6$ and $R^7$, at each occurrence, are each independently hydrogen;
$R^8$, at each occurrence, is independently selected from the group consisting of $C_{1-6}$ alkyl and heterocyclyl; wherein the $R^8C_{1-6}$ alkyl is optionally substituted with one substituent independently selected from the group consisting of $R^{16}$, $OR^{16}$, $SO_2R^{16}$, and $NHR^{16}$;
$R^k$, at each occurrence, is independently selected from the group consisting of $C_{1-6}$ alkyl, $C_{3-7}$ heterocycloalkyl, $C_{3-7}$ cycloalkyl and $C_{1-6}$ haloalkyl;
$R^{16}$, at each occurrence, is independently selected from the group consisting of $C_{1-4}$ alkyl, aryl, and heterocycloalkyl; wherein the $R^{16}C_{1-4}$ alkyl is optionally substituted with one substituent independently selected from the group consisting of $OCH_3$, $OCH_2CH_2OCH_3$, and $OCH_2CH_2NHCH_3$;
q is 1 or 2;
s is 0;
r is 0 or 1;
wherein the sum of s and r is 0 or 1;
m is O;
n is 0, 1, or 2;
o is 0 or 1; and
p is 0.

Still another embodiment pertains to a compound having Formula (VI) selected from the group consisting of
6-[8-(1,3-benzothiazol-2-ylcarbamoyl)-3,4-dihydroisoquinolin-2(1H)-yl]-2'-(tricyclo[3.3.1.1³,⁷]dec-1-ylmethoxy)-3,4'-bipyridine-2-carboxylic acid;
6-[8-(1,3-benzothiazol-2-ylcarbamoyl)-3,4-dihydroisoquinolin-2(1H)-yl]-3'-methyl-2'-(tricyclo[3.3.1.1³,⁷]dec-1-ylmethoxy)-3,4'-bipyridine-2-carboxylic acid;

6-[8-(1,3-benzothiazol-2-ylcarbamoyl)-3,4-dihydroisoquinolin-2(1H)-yl]-2'-[cyclooctyl(methyl)amino]-3'-methyl-3,4'-bipyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfonyl)-3,4'-bipyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid;

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid; and therapeutically acceptable salts, metabolites, prodrugs, salts of metabolites, and salts of prodrugs thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-xL proteins are expressed, said compositions comprising an excipient and a therapeutically effective amount of the compound having Formula (I).

Still another embodiment pertains to methods of treating disease in a patient during which anti-apoptotic Bcl-xL proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-xL proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-xL proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-xL proteins.

Certain precursor compounds which may be metabolized in vitro or in vivo to form compounds having Formula (I) may also have utility for treating diseases associated with expression of anti-apoptotic Bcl-xL proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl)benzenesulfonamide) or ABT-737 (i.e., N-(4-(4-((4'-chloro(1,1'-biphenyl)-2-yl) methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO®(oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS®(idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH 1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-xL proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 mol preloaded Wang resin/vessel on an ABI 433A peptide synthesizer using 250 mol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (1× dichloromethane and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 µm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 µm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe Acetyl-(SEQ ID NO: 1)GQVGRQLAIIGDK(6-FAM)-(SEQ ID NO: 2)INR-NH$_2$ Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak: Acetyl-(SEQ ID NO: 1)GQVGRQLAIIGDK(6-FAM)-(SEQ ID NO:2)INR-NH$_2$ The protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM: TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in DMF and confirmed complete by ninhydrin testing. The peptide was cleaved from the resin and side-chains deprotected by treating with 80:5: 5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)$^+$).

Time Resolved-Fluorescence Resonance Energy Transfer (TR-FRET) Assay

The measurement of competition of compounds of the invention with F-Bak for a Bcl-2 family protein (Bcl-xL) binding site using a Time Resolved Fluorescence Resonance Energy Transfer (TR-FRET) binding assay:
Test compounds were serially diluted in DMSO starting at 50 M (2× starting concentration; 10% DMSO) and 10 µL transferred into a 384-well plate. Then 10 µL of a protein/probe/antibody mix is added to each well at final concentrations listed in Table 1.

TABLE 1

| Protein | Probe | Protein (nM) | Probe (nM) | Antibody | Antibody (nM) |
|---------|-------|--------------|------------|----------|---------------|
| GST-Bcl-xL | F-Bak (GQVGRQLAIIGDK (6-FAM) INR-amide) | 1 | 100 | Tb-anti-GST | 1 |

The samples are then mixed on a shaker for 1 minute then incubated for an additional 2 hours at room temperature. For each assay plate, a probe/antibody and protein/antibody/probe mixture were included as a negative and a positive control, respectively. Fluorescence was measured on the Envision (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (Wang, Z. X. *An exact mathematical expression for describing competitive binding of two different ligands to a protein molecule*. FEBS Lett. 1995 360:111-114). The TR-FRET assay can be performed in the presence of varying concentrations of human serum (HS) or fetal bovine serum (FBS). TR-FRET assay results ($K_i$ in nanomolar) for representative compounds of Formula (I) set forth in Table 2 are provided below in Table 2.

For comparison, the measurement of the competition of compounds of Formula (I) for other Bcl-2 family protein binding sites (e.g., Bcl-2) using the TR-FRET binding assay was accomplished by substituting GST-Bcl-xL in the TR-FRET assay with other GST-labeled protein, e.g., GST-Bcl-2, prepared in-house.

In one embodiment, compounds of Formula (I) selectively inhibit the Bcl-2 family protein, Bcl-xL, over other Bcl-2 family proteins, such as Bcl-2. For comparison, data ($K_i$ in micromolar) from the measurement of the competition by certain compounds of Formula (I) (i.e., Examples 3, 23, 45, 52 and 59 in Table 3) with F-Bak for the Bcl-2 binding site using the TR-FRET binding assay are 0.007, 0.016, 0.010, 0.104, and 0.007 respectively.

FL5.12 Cellular Assay

The efficacy of compounds of Formula (I) can also be determined in cell-based killing assays using a variety of cell lines and mouse tumor models. For example, their activity on cell viability can be assessed on a panel of cultured tumorigenic and non-tumorigenic cell lines, as well as primary mouse or human cell populations. In one exemplary set of conditions, mouse FL5.12 cells transfected with Bcl-xL were cultured under standard conditions in RPMI with 2 mM glutamine, 1% 100 mM sodium pyruvate, 2% 1 M HEPES, 4 µL/L of 3-mercaptoethanol, 1% penicillin-streptomycin, 10% FBS, and 10% WEHI-3B conditioned media (for IL-3). For assaying the compound activity, the cells were exchanged into an IL-3-depleted deprivation media, which was identical to the growth media except for the absence of FBS and WEHI-3B conditional media, for 2 days. Then the cells were exchanged to 3% FBS assay media (RPMI with 2 mM glutamine, 1% 100 mM sodium pyruvate, 2% 1 M HEPES, 4 µL/L of 3-mercaptoethanol, 1% penicillin-streptomycin, 3% FBS). Compounds in series dilutions were added, and the cells were cultured for 24 hours. Compounds in series dilutions were added, and the cells were cultured for 24 hurs. Cell viability was assayed using the CellTiter-Glo assay (Promega Corp., Madison, Wis.) according to the manufacturer instructions. Individual determinations were the result of duplicate values. Cell viability assay results ($EC_{50}$ in nanomolar) for representative Examples are provided below in Table 2.

TABLE 2

In Vitro Data

| EX | TR-FRET binding Bcl-xL Ki (nM) | FL5.12 Bcl-xL, -IL3, $EC_{50}$ (nM) |
|---|---|---|
| 1 | <0.1 | 39 |
| 2 | <0.1 | <1 |
| 3 | <0.1 | <1 |
| 4 | 0.5 | 918 |
| 5 | <0.1 | 2 |
| 6 | <0.1 | 146 |
| 7 | <0.1 | 37 |
| 8 | <0.1 | 147 |
| 9 | 0.2 | 3 |
| 10 | <0.1 | 29 |
| 11 | <0.1 | 11 |
| 12 | <0.1 | 24 |
| 13 | <0.1 | 71 |
| 14 | 0.2 | <1 |
| 15 | <0.1 | 110 |
| 16 | <0.1 | <1 |
| 17 | <0.1 | 1 |
| 18 | <0.1 | 1 |
| 19 | 0.1 | 3 |
| 20 | 4 | >1000 |
| 21 | 0.6 | 343 |
| 22 | 1 | >1000 |
| 23 | <0.1 | <1 |
| 24 | <0.1 | <1 |
| 25 | 0.8 | >1000 |
| 26 | n.d. | 243 |
| 27 | 0.1 | 214 |
| 28 | 0.5 | 22 |
| 29 | <0.1 | 3 |
| 30 | <0.1 | 49 |
| 31 | <0.1 | 5 |
| 32 | <0.1 | 1 |
| 33 | 0.1 | >1000 |
| 34 | 0.4 | 150 |
| 35 | <0.1 | 1 |
| 36 | 0.3 | 0.8 |
| 37 | <0.1 | 3 |
| 38 | <0.1 | 0.1 |
| 39 | 12 | 0.6 |
| 40 | 0.1 | 47 |
| 41 | <0.1 | 0.4 |
| 42 | 0.3 | 0.5 |
| 43 | 0.2 | 9 |
| 44 | <0.1 | 0.3 |
| 43 | 0.2 | 9 |
| 44 | <0.1 | 0.3 |
| 45 | <0.1 | 0.9 |
| 46 | <0.1 | 1 |
| 47 | 0.2 | 54 |
| 48 | 0.2 | 8 |
| 49 | <0.1 | 5 |

TABLE 2-continued

In Vitro Data

| EX | TR-FRET binding Bcl-xL Ki (nM) | FL5.12 Bcl-xL, -IL3, $EC_{50}$ (nM) |
|---|---|---|
| 50 | 9 | >1000 |
| 51 | 0.3 | 164 |
| 52 | 0.2 | 3 |
| 53 | <0.1 | 4 |
| 54 | 2 | >1000 |
| 55 | 0.4 | 47 |
| 56 | <0.1 | 17 |
| 57 | <0.1 | 12 |
| 58 | <0.1 | 0.3 |
| 59 | <0.1 | 0.3 |
| 60 | <0.1 | 55 |
| 61 | <0.1 | 10 |
| 62 | <0.1 | 0.8 |
| 63 | <0.1 | 3 |
| 64 | <0.1 | 26 |
| 65 | <0.1 | 1 |
| 66 | <0.1 | 26 |
| 67 | <0.1 | 9 |
| 68 | <0.1 | 22 |
| 69 | 0.6 | 449 |
| 70 | <0.1 | 72 |
| 71 | <0.1 | 1 |
| 72 | <0.1 | 0.2 |
| 73 | <0.1 | n.d. |
| 74 | <0.1 | 7 |
| 75 | <0.1 | 3 |
| 76 | <0.1 | 71 |
| 77 | <0.1 | 4 |
| 78 | <0.1 | 3 |
| 79 | <0.1 | 0.9 |
| 80 | <0.1 | 1 |
| 81 | <0.1 | n.d |
| 82 | <0.1 | n.d. |
| 83 | <0.1 | n.d. |
| 84 | 0.9 | >1000 |
| 85 | <0.1 | 111 | n.d. = no data available

Molt-4 Cellular Assay

Molt-4 (ATCC, Manassas, Va.) human acute lymphoblastic leukemia cells were plated 50,000 cells per well in 96-well tissue culture plates in a total volume of 100 µL tissue culture medium supplemented with 10% human serum (Invitrogen, Carlsbad, Calif.) and treated with a 3-fold serial dilution of the compounds of interest from 5 µM to 0.020 µL. Each concentration was tested in duplicate at least 3 separate times. The number of viable cells following 48 hours of compound treatment was determined using the CellTiter 96® Aqueous non-radioactive cell proliferation MTS assay according to manufacturer's recommendations (Promega Corp., Madison, Wis.). Molt-4 cell viability results (i.e. $EC_{50}$ in micromolar) for certain compounds of Formula (I), i.e., Examples 1, 3, 10, 18, 23, 28, 45, 52, 59, and 72 in Table 2, are 0.201, 0.006, 0.487, 0.024, 0.016, 0.526, 0.004, 0.029, 0.024, and 0.035 respectively.

Single Dose Pharmacokinetics

The single dose pharmacokinetics of select compounds were evaluated in Sprague-Dawley rats (Charles River) after a 5 mg/kg oral dose (n=3) (10% DMSO in PEG-400) administered by gavage or by 5 mg/kg IV bolus dose (n=3) (10% DMSO in PEG-400). Compound and the internal standard were separated from each other and coextracted contaminants on a 50 mm×3 mm Keystone Betasil CN 5 µm column with an acetonitrile/0.1% trifluoroacetic acid mobile phase (50:50, by volume) at a flow rate of 0.7 mL/min. Analysis was performed on a Sciex API3000 biomolecular mass analyzer with a heated nebulizer interface. Compound and internal standard peak areas were determined using Sciex MacQuan software. The plasma drug concentration of each sample was calculated by least-squares linear regression analysis (nonweighted) of the peak area ratio (parent/internal standard) of the spiked plasma standards versus concentration. The plasma concentration data were submitted to multiexponential curve fitting using WinNonlin.3. The area under the plasma concentration-time curve was calculated using the linear trapezoidal rule for the plasma concentration-time profiles.

In pharmacology, bioavailability (BA) is a subcategory of absorption and is used to describe the fraction of an administered dose of unchanged drug that reaches the systemic circulation, one of the principal pharmacokinetic properties of drugs. By definition, when a medication is administered intravenously, its bioavailability is 100% (Griffin, J. P. The Textbook of Pharmaceutical Medicine (6th Ed.) New Jersey: BMJ Books). However, when a medication is administered via other routes (such as orally), its bioavailability generally decreases (due to incomplete absorption and first-pass metabolism) and may vary from patient to patient. Bioavailability is one of the essential tools in pharmacokinetics, as bioavailability must be considered when calculating dosages for non-intravenous routes of administration. One way to calculate bioavailability of a drug or agent is by dividing the plasma concentration following an oral dose by the concentration following an intravenous dose. The oral bioavailability (as represented by % F) in Sprague-Dawley rats for representative compounds of the invention are provided below in Table 3.

In the drug discovery setting, it is generally accepted that Lipinski's "rule of 5" predicts that poor oral absorption or poor permeation for a drug is likely when two or more of the following metrics are satisfied: i) there are more than 5 hydrogen bond donors, ii) the molecular weight is greater than 500, iii) there are greater than 10 hydrogen bond acceptors (expressed as the sum of nitrogen and oxygen atoms), or iv) the calculated Log P (c Log P) is greater than 5 (Lipinski et al. Adv. Drug Del. Rev. 2001, 3-26). Indeed, the combination of high molecular weight (>500) and high c Log P (>5) is the best predictor of poor absorption or permeation. Compounds of the invention generally exceed the recommended ranges pertaining to molecular weight (>500) and c Log P (>5). It is notable, therefore, that compounds of Formula (I) have acceptable oral bioavailability in rats (as defined by % F>1 0, see Martin J. Med. Chem. 2005, 48, 3164.), as illustrated in Table 3.

TABLE 3

PK Data, Rat p.o. Dose

| EXAMPLE | Molecular weight g/mol | cLogP | F (%), dose |
|---|---|---|---|
| 3 | 658.8 | 9.0 | 13, 5 mpk |
| 7 | 674.8 | 6.4 | 21, 5 mpk |
| 13 | 646.8 | 5.9 | 10, 5 mpk |
| 16 | 688.8 | 6.6 | 20, 5 mpk |
| 17 | 735.9 | 8.3 | 13, 5 mpk |
| 18 | 762.0 | 8.7 | 31, 5 mpk |
| 21 | 684.9 | 10.9 | 37, 5 mpk |
| 23 | 682.3 | 9.5 | 17, 5 mpk |
| 24 | 659.8 | 8.4 | 29, 5 mpk |
| 42 | 679.2 | 9.5 | 15, 1 mpk |
| 43 | 672.9 | 9.8 | 20, 1 mpk |
| 45 | 732.9 | 6.7 | 45, 1 mpk |

TABLE 3-continued

PK Data, Rat p.o. Dose

| EXAMPLE | Molecular weight g/mol | cLogP | F (%), dose |
|---|---|---|---|
| 46 | 692.9 | 8.5 | 58, 1 mpk |
| 49 | 641.8 | 8.3 | 15, 1 mpk |
| 57 | 659.8 | 8.8 | 21, 1 mpk |
| 58 | 712.9 | 7.3 | 14, 1 mpk |
| 59 | 680.8 | 6.4 | 31, 1 mpk |

Data in Table 2 and cited Molt-4 data show the utility of compounds of the invention to functionally inhibit anti-apoptotic Bcl-xL protein in a cellular context. The ability of compounds to kill FL5.12 cells over-expressing Bcl-xL or human tumor cell lines that are dependant upon Bcl-xL such as Molt-4 cells is a direct measure of the compound's ability to inhibit anti-apoptotic Bcl-xL protein function. Compounds of the invention are very effective in killing FL5.12 cells over-expressing Bcl-xL or human tumor cell lines that are dependant upon Bcl-xL such as Molt-4 cells as demonstrated by low $EC_{50}$ values. In addition, as demonstrated in Table 3, compounds of the invention have good oral bioavailability in preclinical rodent studies, and therefore may find utility as orally-dosed therapeutics in a clinical setting.

Overexpression of Bcl-xL proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-xL proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia greata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/ Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthopathy, sporadic, polyglandular deficiency type I, sporadic polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Schemes and Experimentals

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$, and K$_2$SO$_4$; 9-BBN means 9-borabicyclo(3.3.1)nonane; Boc means tert-butoxycarbonyl; (DHQD)$_2$PHAL means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

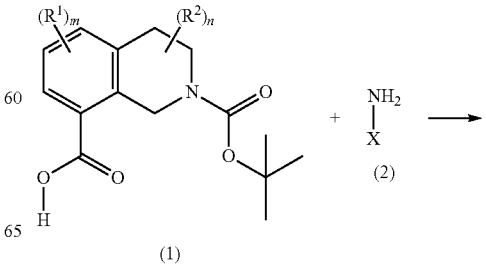

Scheme 1

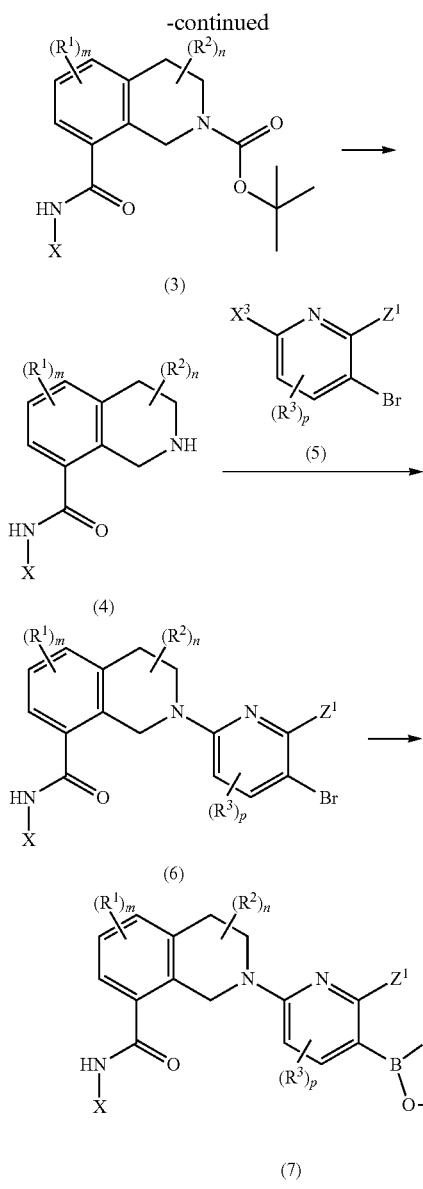

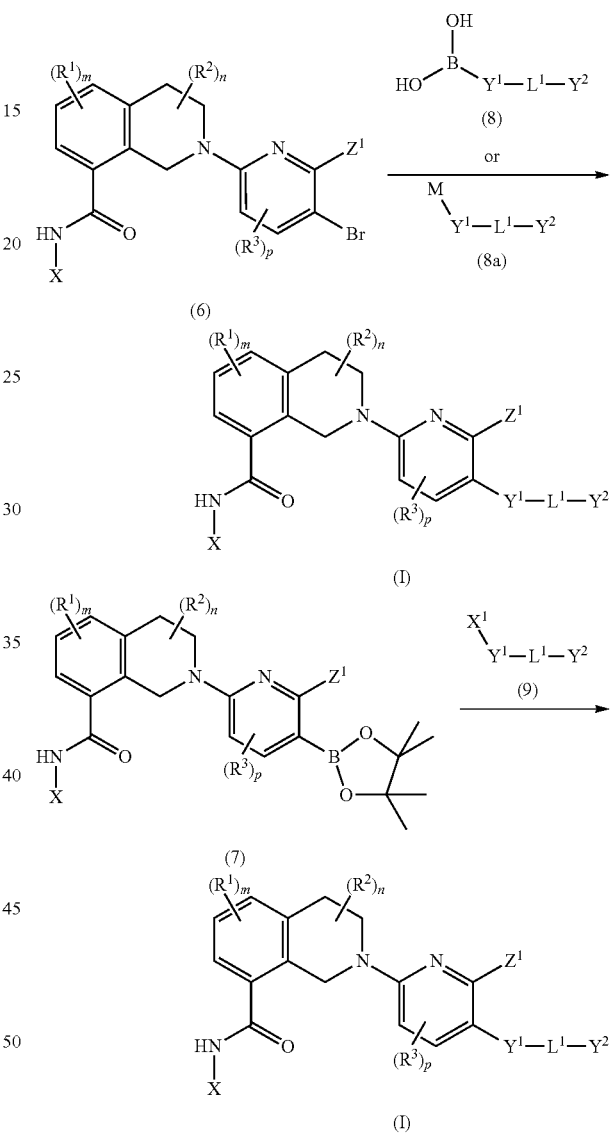

furan, in the presence of a base such as but not limited to triethylamine, and a catalyst such as but not limited to [1,1'-bis(diphenylphosphino)ferrocene]dichloropalladium(II) dichloromethane. The reaction is typically performed at elevated temperature and with the addition of a solvent such as but not limited to acetonitrile. Additionally, the reaction may be performed in a microwave reactor.

As shown in Scheme 1, compounds of formula (1), wherein $R^1$, $R^2$, n, and m are as described herein, can be reacted with compounds of formula (2) wherein X is as described herein, in the presence of a carboxyl activating agent such as but not limited to N-(3-dimethylaminopropyl)-N'-ethylcarbodiimide hydrochloride, and a catalyst such but not limited to 4-dimethylaminopyridine, to provide compounds of formula (3). The reaction is typically performed at room temperature in a solvent such as but not limited to dichloromethane. Compounds of formula (4) can be prepared by reacting compounds of formula (3) with an acid such as but not limited to hydrochloric acid in a solvent such as but not limited to 1,4-dioxane. Compounds of formula (4) can be reacted with compounds of formula (5), wherein $Z^1$, $R^3$ and p are as described herein and $X^3$ is chloro or fluoro, in the presence of a base such as but not limited to cesium carbonate, to provide compounds of formula (6). The reaction is typically performed at an elevated temperature in a solvent such as but not limited to N,N-dimethylacetamide. Compounds of formula (7) can be prepared by reacting compounds of formula (6) with 4,4,5,5-tetramethyl-1,3,2-dioxaborolane in tetrahydrofuran, in the presence of a base such as but not limited to triethylamine, and a catalyst such as but not limited to [1,1'-bis(diphenylphosphino)ferrocene]dichloropalladium(II) dichloromethane. The reaction is typically performed at elevated temperature and with the addition of a solvent such as but not limited to acetonitrile. Additionally, the reaction may be performed in a microwave reactor.

After preparation as described in Scheme 1, compounds of formula (6) can be reacted with a boronic acid (or the boronate equivalent) of formula (8) or an organotin or organozinc halide compound of formula (8a) wherein $Y^1$, $L^1$, and $Y^2$ are as described herein, and M is tributyltin or a zince halide, under Suzuki, Stille, or Negishi coupling conditions known to those skilled in the art and readily available in the literature to provide compounds of formula (I). Alternatively, compounds of formula (7), which can be prepared from compounds of formula (6) as described in Scheme 1, can be reacted with compounds of formula (9) wherein $X^1$ is a triflate or halide, and $Y^1$, $L^1$, and $Y^2$ are as described herein, under Suzuki coupling conditions known to those skilled in the art and readily available in the literature to provide compounds of formula (I).

under Suzuki coupling conditions known to those skilled in the art and readily available in the literature to provide compounds of formula (17), which are representative of com- Scheme 3

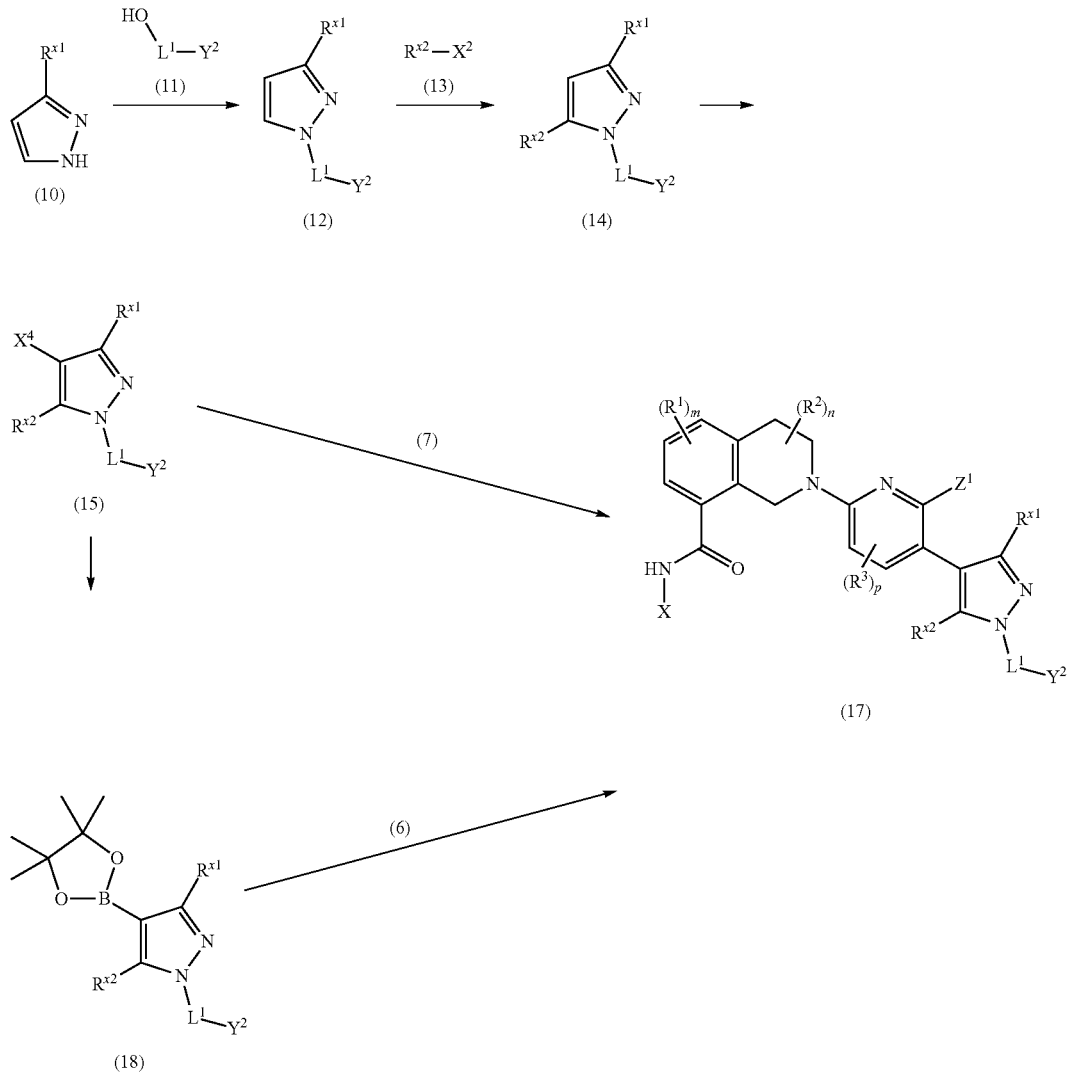

As shown in Scheme 3, pyrazoles of formula (10), wherein $R^{x1}$ is hydrogen or a substituent on $Y^1$ as described herein, can be reacted with alcohols of formula (11), wherein $L^1$ and $Y^2$ are as described herein, and cyanomethylenetributylphosphorane, to provide compounds of formula (12). The reaction is typically performed at ambient temperature in a solvent such as but not limited to toluene. Compounds of formula (14) can be prepared by adding compounds of formula (13) wherein $R^{x2}$ is an appropriate substituent as described herein for substituents on $Y^1$, and $X^2$ is a halide, to a cold solution of compounds of formula (12) treated with n-butyllithium in hexanes. The reaction is typically performed in a solvent such as but not limited to tetrahydrofuran. Compounds of formula (14) can be treated with N-bromosuccinimide or N-iodosuccinimide to provide compounds of formula (15), wherein $X^4$ is bromo or iodo. The reaction is typically performed in a solvent such as N,N-dimethylformamide. Compounds of formula (15) can be reacted with compounds of formula (7)

pounds of formula (I). Alternatively, compounds of formula (15) can be reacted with triisopropyl borate, in the presence of n-butyllithium in hexanes, followed by pinacol to provide compounds of formula (18). The additions are typically performed at low temperature in a solvent such as but not limited to tetrahydrofuran, toluene, or mixtures thereof. Alternatively, compounds of the formula (15) can be treated with 4,4,5,5-tetramethyl-1,3,2-dioxaborolane in the presence of a palladium catalyst system such as but not limited to bis(acetonitrile)palladium dichloride and SPhos in a solvent such as but not limited to 1,4-dioxane to provide compounds of the formula 18. The reaction is typically performed at elevated temperature. Compounds of formula (18) can be reacted with compounds of formula (6) under Suzuki coupling conditions known to those skilled in the art and readily available in the literature to provide compounds of formula (17), which are representative of compounds of formula (I).

Scheme 4

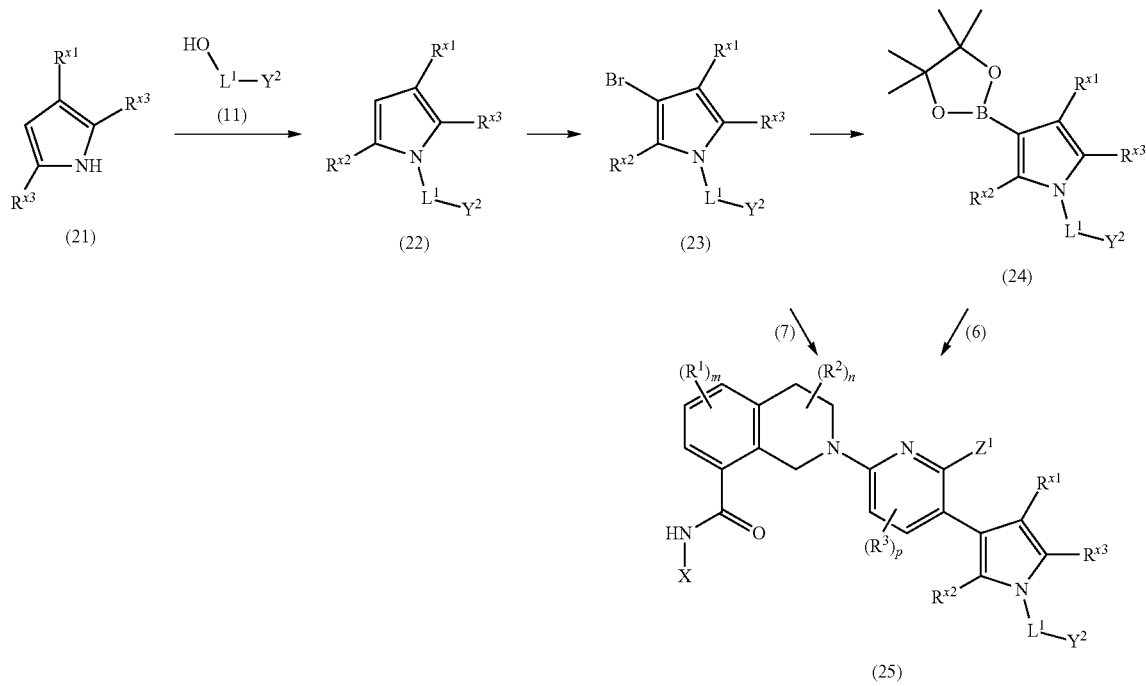

Pyrroles of formula (21) wherein $R^{x1}$, $R^{x2}$, and $R^{x3}$ are hydrogen or are as described herein for substituents on $Y^1$, can be reacted with alcohols of formula (11), wherein $Y^2$ and $L^1$ are as described herein, and cyanomethylenetributylphosphorane, to provide compounds of formula (22). The reaction is typically performed at ambient temperature in a solvent such as but not limited to toluene. Compounds of formula (22) can be treated with N-bromosuccinimide to provide compounds of formula (23). The reaction is typically performed in a solvent such as N,N-dimethylformamide. Compounds of formula (23) can be reacted with triisopropyl borate, in the presence of n-butyllithium in hexanes, followed by pinacol to provide compounds of formula (24). The additions are typically performed at low temperature in a solvent such as but not limited to tetrahydrofuran, toluene, or mixtures thereof. Alternatively, compounds of the formula (23) can be treated with 4,4,5,5-tetramethyl-1,3,2-dioxaborolane in the presence of a palladium catalyst system such as but not limited to bis(acetonitrile)palladium dichloride and SPhos in a solvent such as but not limited to 1,4-dioxane to provide compounds of the formula (24). The reaction is typically performed at an elevated temperature. Compounds of formula (24) can be reacted with compounds of formula (6) under Suzuki coupling conditions known to those skilled in the art and readily available in the literature to provide compounds of formula (25), which are representative of compounds of formula (I). Alternatively, compounds of formula (23) can be reacted with compounds of formula (7) under Suzuki coupling conditions known to those skilled in the art and readily available in the literature to provide compounds of formula (25), which are representative of compounds of formula (I).

Scheme 5

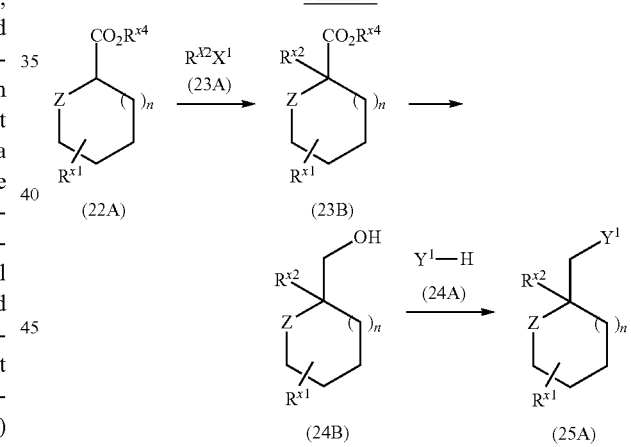

Compounds of formula (22A), wherein Z is O, a substituted or unsubstituted N, or a substituted or unsubstituted C; $R^{x1}$ is hydrogen or is as described herein for substituents on $Y^2$; $R^{x4}$ is alkyl; and n is 0, 1, or 2; can be added to a cooled solution of lithium diisopropylamide, followed by the addition of compounds of formula (23A); wherein $R^{x2}$ is an appropriate substituent as described herein for substituents on $Y^1$, and $X^1$ is a halide; to provide compounds of formula (23B). The reaction is typically performed at low temperature before warming to ambient temperature in a solvent such as but not limited to tetrahydrofuran. Compounds of formula (23B) can be reacted with $LiAlH_4$ to provide compounds of formula (24B). The reaction is typically performed at an elevated temperature in a solvent such as but not limited to diethyl ether. Compounds of formula (25A) can be prepared by reacting compounds of formula (24B) with compounds of formula (24A) wherein $Y^1$ is as described herein; and cyanomethyl-enetributylphosphorane. The reaction is typically performed at ambient temperature in a solvent such as but not limited to toluene. Compounds of formula (25A) can be processed in a manner similar to compounds of formula (12) in Scheme 3 and compounds of formula (22) in Scheme 4 to provide compounds of formula (I).

Scheme 6

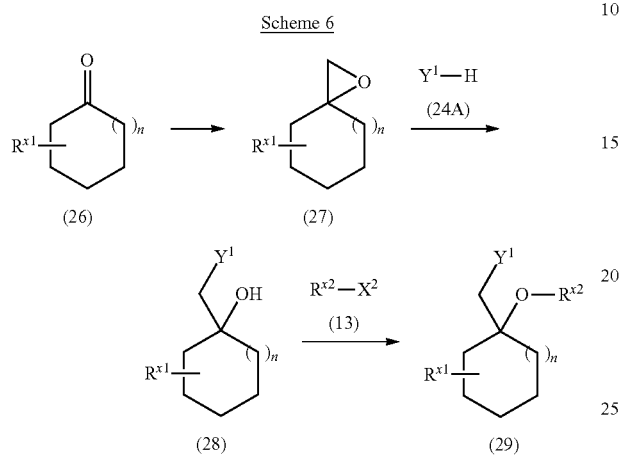

As shown in Scheme 6, compounds of formula (27), wherein $R^{x1}$ is hydrogen or a substituent on $Y^1$ as described herein, can be prepared by reacting compounds of formula (26) with trimethylsulfonium iodide, in the presence of potassium tert-butoxide. The reaction is typically performed at ambient temperature in an anhydrous solvent such as but not limited to dimethylsulfoxide. Compounds of formula (27) can be added to a mixture of compounds of formula (24A) and a base such as but not limited to cesium carbonate, to provide compounds of formula (28). The reaction is typically performed at elevated temperature in a solvent such as but not limited to N,N-dimethylformamide, and may be performed in a microwave reactor. Compounds of formula (28) can be treated with sodium hydride, followed by the addition of compounds of formula (13) to provide compounds of formula (29). The reaction is typically performed at ambient temperature in a solvent such as but not limited to tetrahydrofuran, and may involve the use of hexamethylphosphoramide. Compounds of formula (29) can be processed in a manner similar to compounds of formula (12) in Scheme 3 and compounds of formula (22) in Scheme 4 to provide compounds of formula (I).

Scheme 7

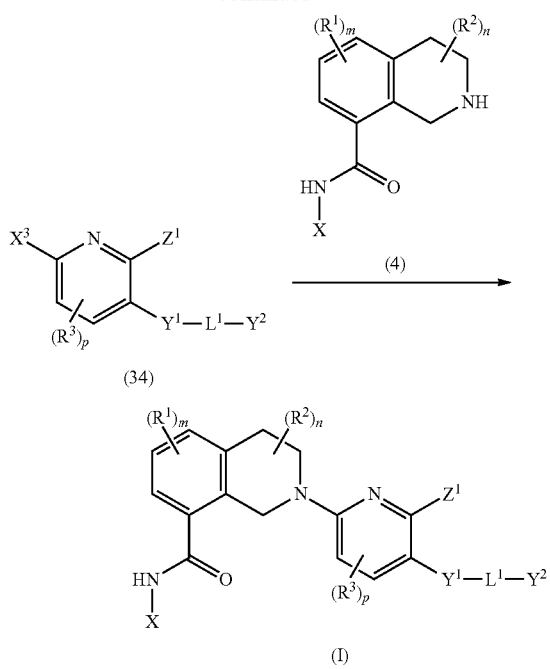

Compounds of formula (33) wherein M is a boronic acid, boronate, or tributlytin attached to $Y^1$ and $Y^1$, $L^1$, and $Y^2$ are as described herein, and $X^3$ is chloro or fluoro; can be reacted with compounds of formula (32) wherein $Z^1$, $R^3$, and p are as described herein, under Suzuki or Stille coupling conditions known to those skilled in the art and readily available in the literature to provide compounds of formula (34). Compounds of formula (34) can be reacted with compounds of formula (4), in the presence of a base such as but not limited to cesium carbonate, to provide compounds of formula (I). The reaction is typically performed at an elevated temperature in a solvent such as but not limited to N,N-dimethylacetamide.

Scheme 8

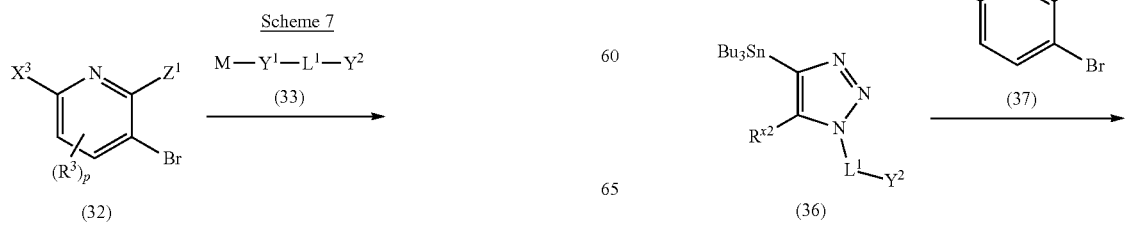

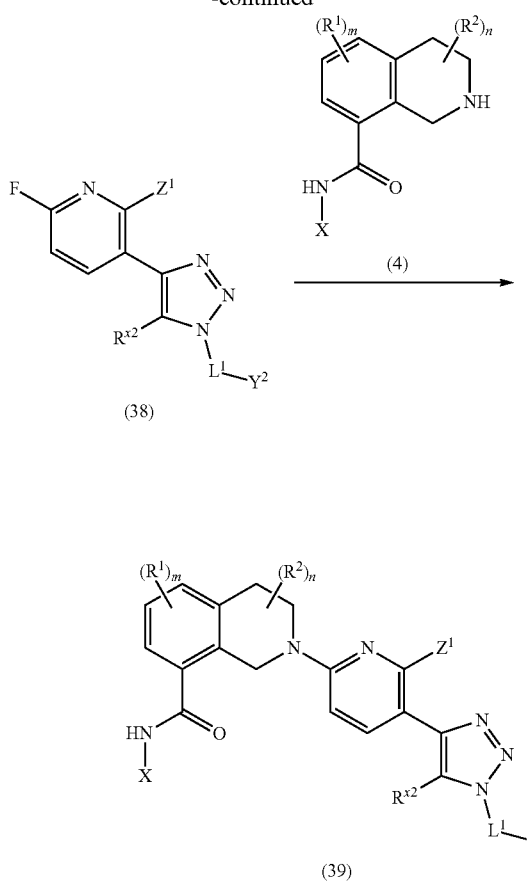

(38)

(39)

Triazoles of formula (36) can be prepared by reacting azides of formula (35), wherein $L^1$ and $Y^2$ are as described herein, with compounds of formula (36A) wherein $R^{x2}$ is alkyl, under conditions known to those skilled in the art and readily available in the literature. Compounds of formula (37), wherein $Z^1$ is as described herein, can be reacted with compounds of formula (36) under Stille coupling conditions known to those skilled in the art and readily available in the literature to provide compounds of formula (38). Compounds of formula (4), wherein $R^1$, $R^2$, X, m and n are as described herein, can be reacted with compounds of formula (38), in the presence of a base such as but not limited to cesium carbonate, to provide compounds of formula (39), which are representative of compounds of formula (I). The reaction is typically performed at an elevated temperature in a solvent such as but not limited to N,N-dimethylacetamide.

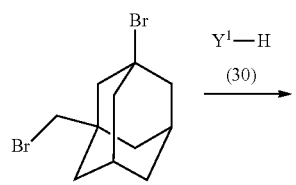

Scheme 9

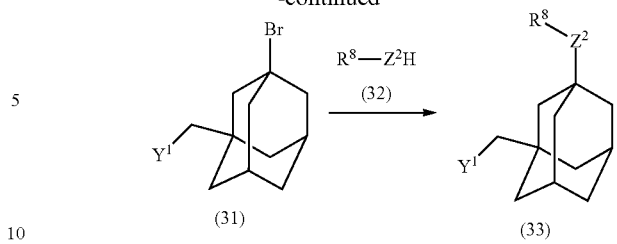

As shown in Scheme 9, 1-bromo-3-(bromomethyl)-adamantane can be reacted with compounds of formula (30), wherein $Y^1$ is as described herein, in the presence of sodium hydride to provide compounds of formula (31). The addition is typically performed in a solvent such as but not limited to N,N-dimethylformamide at low temperature, prior to warming to an elevated temperature. Compounds of formula (31) can be reacted with compounds of formula (32), optionally in the presence of silver sulfate, wherein $R^8$ is as described herein and $Z^2$ is O, NH, or $NR^8$, to provide compounds of formula (33) which are representative of compounds of formula (9). The reaction is typically performed at elevated temperature and may involve an additional solvent. Additionally, the reaction may be performed in a microwave reactor. Compounds of formula (33) can be processed in a manner similar to compounds of formula (12) in Scheme 3 and compounds of formula (22) in Scheme 4 to provide compounds of formula (I).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXAMPLES

Example 1

6-[8-(1,3-benzothiazol-2-ylcarbamoyl)-3,4-dihydroisoquinolin-2(1H)-yl]-3-{1-[tricyclo[3.3.1.1$^{3,7}$]dec-1-ylmethyl]-1H-pyrazol-4-yl}pyridine-2-carboxylic acid Example 1A 4-(4,4,5,5-tetramethyl-1,3,2-dioxaborolan-2-yl)-1-(tricyclo[3.3.1.1$^{3,7}$]dec-1-ylmethyl)-1H-pyrazole A mixture of 1-(bromomethyl)adamantane (0.458 g) and 4-(4,4,5,5-tetramethyl-1,3,2-dioxaborolan-2-yl)-1H-pyrazole (0.377 g) in N,N-dimethylformamide (5 mL) was cooled to 0° C. To this solution was added 60% sodium hydride (0.096 g). The solution was heated at 70° C. overnight. The reaction mixture was partitioned between water and ethyl acetate. The aqueous layer was extracted with additional ethyl acetate twice. The combined organic layers were washed with brine, dried over MgSO$_4$, filtered, and concentrated. The residue was purified by flash column chromatography on silica gel eluting with 25% ethyl acetate in hexanes to provide the title compound.

Example 1B tert-butyl 8-(benzo[d]thiazol-2-ylcarbamoyl)-3,4-dihydroisoquinoline-2(1H)-carboxylate To a solution of 2-(tert-butoxycarbonyl)-1,2,3,4-tetrahydroisoquinoline-8-carboxylic acid (6.8 g) and benzo[d]thiazol-2-amine (5.52 g) in dichloromethane (80 mL) was added 1-ethyl-3-[3-(dimethylamino)propyl]-carbodiimide hydrochloride (9.4 g) and 4-dimethylaminopyridine (6 g). The mixture was stirred at room temperature overnight. The reaction mixture was diluted with dichloromethane (400 mL), washed with 5% aqueous HCl, water, and brine, and dried over $Na_2SO_4$. The mixture was filtered and the filtrate was concentrated under reduced pressure to provide the title compound.

Example 1C

N-(benzo[d]thiazol-2-yl)-1,2,3,4-tetrahydroisoquinoline-8-carboxamide dihydrochloride To a solution of EXAMPLE 1B (8.5 g) in dichloromethane (80 mL) was added 2N HCl in ether (80 mL). The reaction mixture was stirred at room temperature overnight and concentrated under reduced pressure to provide the title compound.

Example 1D tert-butyl 3-bromo-6-chloropicolinate

Tosyl chloride (7.7 g) was added to a solution of 2-chloro-5-bromo picolinic acid (4 g) and pyridine (9.2 mL) in t-butanol (33 mL) at 0° C. The reaction was then stirred at room temperature for 12 hours. $NaHCO_3$ (aqueous, saturated) was then added and the mixture was extracted three times with ethyl acetate. The combined organic phases were washed with brine and dried over $Na_2SO_4$. Filtration and evaporation of the organic solvent provided the title compound which was used in the next step without further purification.

Example 1E tert-butyl 6-(8-(benzo[d]thiazol-2-ylcarbamoyl)-3,4-dihydroisoquinolin-2(1H)-yl)-3-bromopicolinate EXAMPLE 1D (0.736 g), EXAMPLE 1C (1.62 g), and $Cs_2CO_3$ (4.1 g) were stirred in 12 mL of anhydrous N,N-dimethylacetamide at 120° C. for 12 hours. The cooled reaction mixture was then diluted with ethyl acetate and 10% citric acid. The organic phase was washed three times with citric acid, once with water and brine, and dried over $Na_2SO_4$. Filtration and concentration afforded crude material, which was chromatographed on silica gel using 0-40% ethyl acetate in hexanes to provide the title compound.

Example 1F tert-butyl 3-{1-[tricyclo[3.3.1.1$^{3,7}$]dec-1-ylmethyl]-1H-pyrazol-4-yl}-6-[8-(1,3-benzothiazol-2-ylcarbamoyl)-3,4-dihydroisoquinolin-2(1H)-yl]pyridine-2-carboxylate A mixture of EXAMPLE 1E (0.100 g), EXAMPLE 1A (0.059 g), tetrakis(triphenylphosphine)palladium(0) (0.022 g) and CsF (0.090 g) in 1,2-dimethoxyethane (2 mL) and methanol (1 mL) was heated at 120° C. for 30 minutes under microwave heating conditions (Biotage Initiator). The reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash column chromatography on silica gel eluting with 25% ethyl acetate in hexanes to afford the title compound.

Example 1G

6-[8-(1,3-benzothiazol-2-ylcarbamoyl)-3,4-dihydroisoquinolin-2(1H)-yl]-3-{1-[tricyclo[3.3.1.1$^{3,7}$]dec-1-ylmethyl]-1H-pyrazol-4-yl}pyridine-2-carboxylic acid EXAMPLE 1F (90 mg) in dichloromethane (3 mL) was treated with trifluoroacetic acid (3 mL), and the reaction was stirred at room temperature for 24 hours. The volatiles were removed under reduced pressure. The residue was purified by Prep HPLC using Gilson system eluting with 20-80% acetonitrile in water containing 0.1% v/v trifluoroacetic acid. The desired fractions were combined and freeze-dried to provide the title compound. $^1$H NMR (500 MHz, dimethylsulfoxide-d$_6$) δ ppm 12.85 (s, 1H), 8.04 (d, 1H), 7.80 (d, 1H), 7.82 (d, 1H), 7.67 (s, 1H), 7.61 (d, 1H), 7.43 (s, 1H), 7.46-7.50 (m, 1H), 7.42-7.44 (m, 1H), 7.34-7.38 (m, 2H), 6.94 (d, 1H), 4.94 (s, 2H), 3.85-3.88 (m, 2H), 3.77 (s, 2H), 3.00 (t, 2H), 1.92 (m, 3H), 1.52-1.65 (m, 6H), 1.45-1.46 (m, 6H).

Example 2

6-[8-(1,3-benzothiazol-2-ylcarbamoyl)-3,4-dihydroisoquinolin-2(1H)-yl]-3-[3,5-dimethyl-1-(tricyclo[3.3.1.1$^{3,7}$]dec-1-ylmethyl)-1H-pyrazol-4-yl]pyridine-2-carboxylic acid

Example 2A 3,5-dimethyl-4-(4,4,5,5-tetramethyl-1,3,2-dioxaborolan-2-yl)-1-(tricyclo[3.3.1.1$^{3,7}$]dec-1-ylmethyl)-1H-pyrazole To a solution of 1-adamantanemethanol (0.090 g), 3,5-dimethyl-4-(4,4,5,5-tetramethyl-1,3,2-dioxaborolan-2-yl)-1H-pyrazole (0.160 g) and cyanomethylenetributylphosphorane (0.215 g) were added and stirred together in toluene (2 mL) at room temperature. After stirring overnight the reaction was loaded directly onto silica gel and eluted using a gradient of 2% to 20% ethyl acetate/hexanes to provide the title compound.

Example 2B tert-butyl 6-[8-(1,3-benzothiazol-2-ylcarbamoyl)-3,4-dihydroisoquinolin-2(1H)-yl]-3-[3,5-dimethyl-1-(tricyclo[3.3.1.1$^{3,7}$]dec-1-ylmethyl)-1H-pyrazol-4-yl]pyridine-2-carboxylate EXAMPLE 1E (0.150 g), EXAMPLE 2A (0.121 g), tetrakis(triphenylphosphine)palladium(0) (14 mg) and cesium carbonate (0.260 g) were stirred together in N,N-dimethylformamide (1 mL), dioxane (0.7 mL), and water (0.4 mL) and the reaction degassed with nitrogen and heated at 100° C. for 1 hour. The reaction was diluted with ethyl acetate (25 mL)

and washed with water (25 mL) and brine (25 mL), dried over magnesium sulfate, filtered, and concentrated. Silica gel chromatography eluting with a gradient of 2% to 50% ethyl acetate/hexanes provided the title compound.

Example 2C

6-[8-(1,3-benzothiazol-2-ylcarbamoyl)-3,4-dihydroisoquinolin-2(1H)-yl]-3-[3,5-dimethyl-1-(tricyclo[3.3.1.1$^{3,7}$]dec-1-ylmethyl)-1H-pyrazol-4-yl]pyridine-2-carboxylic acid To EXAMPLE 2B (0.070 g) in dichloromethane (1 mL) was added TFA (1 mL) and the reaction was stirred overnight. The reaction was concentrated, dissolved in dichloromethane and loaded onto silica gel and eluted using a gradient of 0.5% to 5% methanol/dichloromethane to provide the title compound. $^1$H NMR (300 MHz, dimethylsulfoxide-d$_6$) δ 13.04 (s, 1H), 12.84 (s, 1H), 8.04 (dd, 1H), 7.79 (d, 1H), 7.71 (d, 1H), 7.62 (t, 2H), 7.54-7.32 (m, 5H), 7.22-7.14 (m, 2H), 7.11-7.01 (m, 2H), 6.93 (d, 1H), 4.94 (s, 2H), 4.30 (t, 2H), 3.86 (t, 2H), 3.08 (t, 2H), 3.00 (t, 2H).

Example 3

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 3A 1-(tricyclo[3.3.1.1$^{3,7}$]dec-1-ylmethyl)-1H-pyrazole

The title compound was prepared by substituting pyrazole for 3,5-dimethyl-4-(4,4,5,5-tetramethyl-1,3,2-dioxaborolan-2-yl)-1H-pyrazole in EXAMPLE 2A.

Example 3B 1-(tricyclo[3.3.1.1$^{3,7}$]dec-1-ylmethyl)-5-methyl-1H-pyrazole

A solution of EXAMPLE 3A (869 mg) in tetrahydrofuran (10 mL) was chilled to −45° C. n-Butyllithium (2.3 M solution in hexanes, 2.10 mL) was added dropwise over 5 minutes. The reaction was stirred for 1.5 hours, during which time the temperature increased to −20° C. Iodomethane (0.305 mL) was added dropwise over 3 minutes. The reaction was stirred for 30 minutes between −20 and −15° C. Water (25 mL) was added and the mixture was extracted with ethyl acetate (3×25 mL). The extracts were dried (Na$_2$SO$_4$), filtered, and concentrated to provide the title compound.

Example 3C 1-(tricyclo[3.3.1.1$^{3,7}$]dec-1-ylmethyl)-4-bromo-5-methyl-1H-pyrazole EXAMPLE 3B (865 mg) was dissolved in N,N-dimethylformamide (7 mL) and N-bromosuccinimide (334 mg) was added. The reaction was stirred at room temperature for 1 hour. Water (25 mL) was added and the product was obtained by filtration.

Example 3D 1-(tricyclo[3.3.1.1$^{3,7}$]dec-1-ylmethyl)-5-methyl-4-(4,4,5,5-tetramethyl-1,3,2-dioxaborolan-2-yl)-1H-pyrazole EXAMPLE 3C (250 mg) was placed into a flask, and was degassed with N$_2$. Tetrahydrofuran (2.5 mL) and toluene (2.500 mL) were added and the solution was chilled to −78° C. Triisopropyl borate (0.243 mL) was added, followed by dropwise addition of n-butyllithium (2.3 M in hexanes, 0.6 mL) over 5 minutes. The mixture was stirred for 15 minutes at −78° C. and then a degassed solution of pinacol (143 mg) in tetrahydrofuran (1 mL) was added over 2 minutes. After stirring for 10 minutes at −78° C., the reaction was warmed to room temperature and stirred for 45 minutes. Water (0.073 mL) was then added and the mixture was stirred for 2 hours. The crude reaction mixture was concentrated to dryness to provide the title compound.

Example 3E tert-butyl 6-(8-(benzo[d]thiazol-2-ylcarbamoyl)-3,4-dihydroisoquinolin-2(1H)-yl)-3-[1-(tricyclo[3.3.1.1$^{3,7}$]dec-1-ylmethyl)-5-methyl-1H-pyrazol-4-yl]picolinate The title compound was prepared by substituting EXAMPLE 3D for EXAMPLE 2A in EXAMPLE 2B.

Example 3F

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 3E for EXAMPLE 2B in EXAMPLE 2C. $^1$H NMR (300 MHz, dimethylsulfoxide-d$_6$) δ ppm 12.84 (s, 1H), 12.74 (s, 1H), 8.03 (d, 1H), 7.79 (d, 1H), 7.61 (d, 1H), 7.40-7.53 (m, 3H), 7.31-7.39 (m, 2H), 7.26 (s, 1H), 6.94 (d, 1H), 4.95 (s, 2H), 3.89 (t, 2H), 3.70 (s, 2H), 3.01 (t, 2H), 2.10 (s, 3H), 1.89-1.95 (m, 3H), 1.48-1.69 (m, 12H).

Example 4

6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid

Example 4A 4-bromo-1-(spiro[3.5]nonan-7-ylmethyl)-1H-pyrazole

The title compound was prepared by substituting 4-bromo-1H-pyrazole for 3,5-dimethyl-4-(4,4,5,5-tetramethyl-1,3,2- dioxaborolan-2-yl)-1H-pyrazole and 7-hydroxymethyl-spiro[3.5]nonane for 1-adamantanemethanol in EXAMPLE 2A.

Example 4B tert-butyl 6-(8-(benzo[d]thiazol-2-ylcarbamoyl)-3,4-dihydroisoquinolin-2(1H)-yl)-3-(4,4,5,5-tetramethyl-1,3,2-dioxaborolan-2-yl)picolinate A mixture of EXAMPLE 1E (1.2 g), 1.0 M 4,4,5,5-tetramethyl-1,3,2-dioxaborolane in tetrahydrofuran (4.24 mL), triethylamine (0.92 mL), and [1,1'-bis(diphenylphosphino)ferrocene]dichloropalladium(II) dichloromethane (0.087 g) in $CH_3CN$ (15 mL) was heated at 100° C. under microwave conditions (Biotage) for 30 minutes. After cooling, the reaction mixture was partitioned between water and ethyl acetate. The organic layer was extracted with additional ethyl acetate twice. The combined organic layers were washed with brine, dried over $MgSO_4$, filtered, and concentrated. The residue was purified by flash column chromatography on silica gel to provide the title compound.

Example 4C tert-butyl 6-(8-(benzo[d]thiazol-2-ylcarbamoyl)-3,4-dihydroisoquinolin-2(1H)-yl)-3-(1-(spiro[3.5]nonan-7-ylmethyl)-1H-pyrazol-4-yl)picolinate A suspension of EXAMPLE 4B (50 mg), EXAMPLE 4A (23.12 mg), tris(dibenzylideneacetone)dipalladium(0) (7 mg), 1,3,5,7-tetramethyl-6-phenyl-2,4,8-trioxa-6-phosphaadamantane (12 mg) and potassium phosphate (52.0 mg) in tetrahydrofuran (1.5 mL) and water (0.5 mL) was heated under microwave conditions (Biotage) at 140° C. for 5 minutes. The reaction mixture was diluted with ethyl acetate, separated, and purified by chromatography on silica gel using 10-60% ethyl acetate/hexanes as eluent to provide the title compound.

Example 4D

6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid The title compound was prepared by substituting EXAMPLE 4C for EXAMPLE 2B in EXAMPLE 2C. $^1$H NMR (300 MHz, dimethylsulfoxide-$d_6$) δ ppm 12.85 (s, 1H), 8.04 (d, 1H), 7.79 (d, 1H), 7.74 (s, 1H), 7.69 (d, 1H), 7.61 (d, 1H), 7.52 (s, 1H), 7.45-7.51 (m, 1H), 7.40-7.44 (m, 1H), 7.36 (t, 2H), 6.94 (d, 1H), 4.94 (s, 2H), 3.83-3.93 (m, 3H), 3.00 (t, 2H), 1.73-1.85 (m, 2H), 1.55-1.75 (m, 8H), 1.35 (d, 2H), 1.09-1.23 (m, 2H), 0.88-1.04 (m, 2H).

Example 5

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-1H-pyrazol-4-yl)pyridine-2-carboxylic acid

Example 5A 4-bromo-1-{[3,5-dimethyltricyclo[3.3.1.1$^{3,7}$]dec-1-yl]methyl}-1H-pyrazole The title compound was prepared by substituting 4-bromo-1H-pyrazole for 3,5-dimethyl-4-(4,4,5,5-tetramethyl-1,3,2-dioxaborolan-2-yl)-1H-pyrazole and 3,5-dimethyl-1-adamantanemethanol for 1-adamantanemethanol in EXAMPLE 2A.

Example 5B tert-butyl 6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-1H-pyrazol-4-yl)pyridine-2-carboxylate The title compound was prepared by substituting EXAMPLE 5A for EXAMPLE 4A in EXAMPLE 4C.

Example 5C

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-1H-pyrazol-4-yl)pyridine-2-carboxylic acid The title compound was prepared by substituting EXAMPLE 5B for EXAMPLE 2B in EXAMPLE 2C. $^1$H NMR (300 MHz, dimethylsulfoxide-$d_6$) δ ppm 12.86 (s, 1H), 8.04 (d, 1H), 7.79 (d, 1H), 7.72 (d, 1H), 7.67 (s, 1H), 7.61 (d, 1H), 7.53 (s, 1H), 7.44-7.51 (m, 1H), 7.40-7.45 (m, 1H), 7.36 (t, 2H), 6.94 (d, 1H), 4.94 (s, 2H), 3.87 (t, 2H), 3.80 (s, 2H), 3.00 (t, 2H), 1.96-2.05 (m, 1H), 1.26 (d, 6H), 0.96-1.17 (m, 6H), 0.77 (s, 6H).

Example 6

6-[8-(1,3-benzothiazol-2-ylcarbamoyl)-3,4-dihydroisoquinolin-2(1H)-yl]-3-(1-{[3-hydroxytricyclo[3.3.1.1$^{3,7}$]dec-1-yl]methyl}-1H-pyrazol-4-yl)pyridine-2-carboxylic acid

Example 6A

3-[(4-bromo-1H-pyrazol-1-yl)methyl]tricyclo[3.3.1.1$^{3,7}$]decan-1-ol

The title compound was prepared by substituting 4-bromo-1H-pyrazole for 3,5-dimethyl-4-(4,4,5,5-tetramethyl-1,3,2-dioxaborolan-2-yl)-1H-pyrazole and 3-hydroxy-1-adamantanemethanol for 1-adamantylmethanol in EXAMPLE 2A.

Example 6B tert-butyl 6-[8-(1,3-benzothiazol-2-ylcarbamoyl)-3,4-dihydroisoquinolin-2(1H)-yl]-3-(1-{[3-hydroxytricyclo[3.3.1.1$^{3,7}$dec-1-yl]methyl}-1H-pyrazol-4-yl)pyridine-2-carboxylate The title compound was prepared by substituting EXAMPLE 6A for EXAMPLE 4A in EXAMPLE 4C.

Example 6C

6-[8-(1,3-benzothiazol-2-ylcarbamoyl)-3,4-dihydroisoquinolin-2(1H)-yl]-3-(1-{[3-hydroxytricyclo[3.3.1.1$^{3,7}$]dec-1-yl]methyl}-1H-pyrazol-4-yl)pyridine-2-carboxylic acid The title compound was prepared by substituting EXAMPLE 6B for EXAMPLE 2B in EXAMPLE 2C. $^1$H NMR (300 MHz, dimethylsulfoxide-$d_6$) δ ppm 13.06 (s, 1H), 12.86 (s, 1H), 8.04 (d, 1H), 7.79 (d, 1H), 7.71 (d, 1H), 7.68 (s, 1H), 7.61 (d, 1H), 7.53 (s, 1H), 7.44-7.51 (m, 1H), 7.40-7.44 (m, 1H), 7.35 (t, 2H), 6.93 (d, 1H), 4.94 (s, 2H), 4.35 (s, 1H), 3.87 (t, 2H), 3.82 (s, 2H), 3.00 (t, 2H), 2.08 (s, 2H), 1.36-1.56 (m, 6H), 1.33 (s, 6H).

Example 7

6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-1H-pyrazol-4-yl)pyridine-2-carboxylic acid

Example 7A

1-[(3-bromotricyclo[3.3.1.1$^{3,7}$]dec-1-yl)methyl]-4-iodo-1H-pyrazole

A mixture of 1-bromo-3-(bromomethyl)-adamantane (1.0 g) and 4-iodopyrazole (0.63 g) in N,N-dimethylformamide (10 mL) was cooled to 0° C. To this solution was added 60% sodium hydride (0.20 g). The solution was stirred at 65° C. overnight. The reaction mixture was partitioned between water and ethyl acetate. The aqueous layer was extracted with additional ethyl acetate twice. The combined organic layers were washed three times with water, washed with brine, dried over MgSO$_4$, filtered, and concentrated. The residue was purified by flash column chromatography on silica gel eluting with 10% ethyl acetate in hexanes to provide the title compound.

Example 7B 4-iodo-1-[(3-methoxytricyclo[3.3.1.1$^{3,7}$]dec-1-yl)methyl]-1H-pyrazole EXAMPLE 7A (5 g), silver sulfate (6 g) and methanol (15 mL) were heated at 110° C. under microwave conditions (Biotage, Initiator) for 60 minutes. After cooling to room temperature, the suspension was filtered. The solid residue was washed by ethyl acetate (3×5 mL) and filtered. The combined solution was dried under vacuum. The residue was taken up into dichloromethane and purified by flash chromatography (Varian, Superflash SF40-200 g column), eluting with 0-70% ethyl acetate/hexane, to provide the title compound.

Example 7C tert-butyl 6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-1H-pyrazol-4-yl)pyridine-2-carboxylate The title compound was prepared by substituting EXAMPLE 7B for EXAMPLE 4A in EXAMPLE 4C.

Example 7D

6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-1H-pyrazol-4-yl)pyridine-2-carboxylic acid The title compound was prepared by substituting EXAMPLE 7C for EXAMPLE 2B in EXAMPLE 2C. $^1$H NMR (300 MHz, dimethylsulfoxide-d$_6$) δ ppm 12.85 (s, 1H), 8.04 (d, 1H), 7.79 (d, 1H), 7.71 (m, 2H), 7.61 (d, 1H), 7.54 (s, 1H), 7.41 (m, 4H), 6.94 (d, 1H), 4.94 (s, 2H), 3.87 (m, 4H), 3.07 (s, 3H), 3.00 (t, 2H), 2.14 (m, 2H), 1.46 (m, 12H).

Example 8

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-1H-pyrazol-4-yl)pyridine-2-carboxylic acid

Example 8A 4-iodo-1-{[3-(2-methoxyethoxy)tricyclo[3.3.1.1$^{3,7}$]dec-1-yl]methyl}-1H-pyrazole The title compound was prepared by substituting 2-methoxyethanol for methanol in EXAMPLE 7B.

Example 8B tert-butyl 6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-1H-pyrazol-4-yl)pyridine-2-carboxylate The title compound was prepared by substituting EXAMPLE 8A for EXAMPLE 4A in EXAMPLE 4C.

Example 8C

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-1H-pyrazol-4-yl)pyridine-2-carboxylic acid The title compound was prepared by substituting EXAMPLE 8B for EXAMPLE 2B in EXAMPLE 2C. $^1$H NMR (300 MHz, dimethylsulfoxide-d$_6$) δ ppm 12.85 (s, 1H), 8.04 (s, 1H), 7.79 (s, 1H), 7.70 (m, 2H), 7.61 (d, 1H), 7.54 (s, 1H), 7.40 (m, 5H), 6.94 (d, 1H), 4.94 (s, 2H), 3.86 (m, 4H), 3.42 (m, 2H), 3.35 (m, 2H), 3.21 (s, 3H), 3.00 (t, 2H), 2.13 (m, 2H), 1.46 (m, 12H).

Example 9

6-[8-(1,3-benzothiazol-2-ylcarbamoyl)-3,4-dihydroisoquinolin-2(1H)-yl]-3-{1-[(3,5,7-trimethyltricyclo[3.3.1.1$^{3,7}$]dec-1-yl)methyl]-1H-pyrazol-4-yl}pyridine-2-carboxylic acid

Example 9A 3,5,8-trimethyl-1-adamantanemethanol

To a solution of 3,5,8-trimethyl-1-adamantane carboxylic acid (0.5 g) in tetrahydrofuran (3 mL) was dropwise added BH$_3$.tetrahydrofuran (4.50 mL) and the mixture was stirred at room temperature for 14 hours. The reaction mixture was quenched with methanol (3 mL), concentrated and purified by chromatography on silica gel using 0-30% ethyl acetate/hexanes as eluent to provide the title compound.

Example 9B 4-iodo-1-{[3,5,7-trimethyltricyclo[3.3.1.1$^{3,7}$]dec-1-yl]methyl}-1H-pyrazole The title compound was prepared by substituting EXAMPLE 9A for 1-adamantanemethanol and 4-iodopyrazole for 3,5-dimethyl-4-(4,4,5,5-tetramethyl-1,3,2-dioxaborolan-2-yl)-1H-pyrazole in EXAMPLE 2A.

Example 9C tert-butyl 6-[8-(1,3-benzothiazol-2-ylcarbamoyl)-3,4-dihydroisoquinolin-2(1H)-yl]-3-{1-[(3,5,7-trimethyltricyclo[3.3.1.1$^{3,7}$]dec-1-yl)methyl]-1H-pyrazol-4-yl}picolinate The title compound was prepared by substituting EXAMPLE 9B for EXAMPLE 4A in EXAMPLE 4C.

Example 9D

6-[8-(1,3-benzothiazol-2-ylcarbamoyl)-3,4-dihydroisoquinolin-2(1H)-yl]-3-{1-[(3,5,7-trimethyltricyclo[3.3.1.1$^{3,7}$]dec-1-yl)methyl]-1H-pyrazol-4-yl}pyridine-2-carboxylic acid The title compound was prepared by substituting EXAMPLE 9C for EXAMPLE 2B in EXAMPLE 2C. $^1$H NMR (300 MHz, dimethylsulfoxide-d$_6$) δ ppm 12.86 (s, 1H), 8.04 (d, 1H), 7.79 (d, 1H), 7.73 (d, 1H), 7.67 (s, 1H), 7.61 (d, 1H), 7.53 (s, 1H), 7.48 (t, 1H), 7.40-7.44 (m, 1H), 7.36 (t, 2H), 6.95 (d, 1H), 3.87 (t, 1H), 3.82 (s, 2H), 3.00 (t, 2H), 1.03 (s, 6H), 0.92-1.01 (m, 6H), 0.78 (s, 9H).

Example 10

6-[8-(1,3-benzothiazol-2-ylcarbamoyl)-3,4-dihydroisoquinolin-2(1H)-yl]-3-[1-(tricyclo[3.3.1.1$^{3,7}$]dec-2-ylmethyl)-1H-pyrazol-4-yl]pyridine-2-carboxylic acid Example 10A 2-adamantanemethanol The title compound was prepared by substituting 2-adamantane carboxylic acid for 3,5,8-trimethyl-1-adamantane carboxylic acid in EXAMPLE 9A.

Example 10B 1-(tricyclo[3.3.1.1$^{3,7}$]dec-2-ylmethyl)-4-iodo-1H-pyrazole

The title compound was prepared by substituting EXAMPLE 10A for 1-adamantanemethanol and 4-iodopyrazole for 3,5-dimethyl-4-(4,4,5,5-tetramethyl-1,3,2-dioxaborolan-2-yl)-1H-pyrazole in EXAMPLE 2A.

Example 10C tert-butyl 6-[8-(1,3-benzothiazol-2-ylcarbamoyl)-3,4-dihydroisoquinolin-2(1H)-yl]-3-[1-(tricyclo[3.3.1.1$^{3,7}$]dec-2-ylmethyl)-1H-pyrazol-4-yl]pyridine-2-carboxylate The title compound was prepared by substituting EXAMPLE 10B for EXAMPLE 4A in EXAMPLE 4C.

Example 10D

6-[8-(1,3-benzothiazol-2-ylcarbamoyl)-3,4-dihydroisoquinolin-2(1H)-yl]-3-[1-(tricyclo[3.3.1.1$^{3,7}$]dec-2-ylmethyl)-1H-pyrazol-4-yl]pyridine-2-carboxylic acid The title compound was prepared by substituting EXAMPLE 10C for EXAMPLE 2B in EXAMPLE 2C. $^1$H NMR (300 MHz, dimethylsulfoxide-d$_6$) δ ppm 12.84 (s, 1H), 8.04 (d, 1H), 7.74-7.84 (m, 2H), 7.69 (d, 1H), 7.61 (d, 1H), 7.52 (s, 1H), 7.40-7.51 (m, 2H), 7.36 (t, 2H), 6.94 (d, 1H), 4.94 (s, 2H), 4.21 (d, 2H), 3.86 (t, 2H), 3.17 (s, 2H), 3.00 (t, 2H), 2.13-2.24 (m, 1H), 1.98 (d, 2H), 1.44-1.89 (m, 12H), 1.07 (s, 1H).

Example 11

6-[8-(1,3-benzothiazol-2-ylcarbamoyl)-3,4-dihydroisoquinolin-2(1H)-yl]-3-(1-{[3-bromotricyclo[3.3.1.1$^{3,7}$]dec-1-yl]methyl}-1H-pyrazol-4-yl)pyridine-2-carboxylic acid Example 11A tert-butyl 6-[8-(1,3-benzothiazol-2-ylcarbamoyl)-3,4-dihydroisoquinolin-2(1H)-yl]-3-(1-{[3-bromotricyclo[3.3.1.1$^{3,7}$]dec-1-yl]methyl}-1H-pyrazol-4-yl)pyridine-2-carboxylate The title compound was prepared by substituting EXAMPLE 7A for EXAMPLE 4A in EXAMPLE 4C.

Example 11B

6-[8-(1,3-benzothiazol-2-ylcarbamoyl)-3,4-dihydroisoquinolin-2(1H)-yl]-3-(1-{[3-bromotricyclo[3.3.1.1$^{3,7}$]dec-1-yl]methyl}-1H-pyrazol-4-yl)pyridine-2-carboxylic acid The title compound was prepared by substituting EXAMPLE 11A for EXAMPLE 2B in EXAMPLE 2C. $^1$H NMR (300 MHz, dimethylsulfoxide-d$_6$) δ ppm 12.84 (s, 1H), 8.04 (d, 1H), 7.79 (d, 1H), 7.71 (d, 2H), 7.61 (d, 1H), 7.56 (s, 1H), 7.45 (m, 2H), 7.35 (m, 2H), 6.95 (d, 1H), 4.94 (s, 2H), 3.87 (m, 4H), 3.00 (t, 2H), 2.25 (m, 2H), 2.12 (m, 6H), 1.54 (m, 6H).

Example 12

6-[8-(1,3-benzothiazol-2-ylcarbamoyl)-3,4-dihydroisoquinolin-2(1H)-yl]-3-(1-{[3-(propan-2-yloxy)tricyclo[3.3.1.1$^{3,7}$]dec-1-yl]methyl}-1H-pyrazol-4-yl)pyridine-2-carboxylic acid Example 12A 4-iodo-1-{[3-(propan-2-yloxy)tricyclo[3.3.1.1$^{3,7}$]dec-1-yl]methyl}-1H-pyrazole The title compound was prepared by substituting propan-2-ol for methanol in EXAMPLE 7B.

Example 12B tert-butyl 6-[8-(1,3-benzothiazol-2-ylcarbamoyl)-3,4-dihydroisoquinolin-2(1H)-yl]-3-(1-{[3-(propan-2-yloxy)tricyclo[3.3.1.1$^{3,7}$]dec-1-yl]methyl}-1H-pyrazol-4-yl)pyridine-2-carboxylate The title compound was prepared by substituting EXAMPLE 12A for EXAMPLE 4A in EXAMPLE 4C.

Example 12C

6-[8-(1,3-benzothiazol-2-ylcarbamoyl)-3,4-dihydroisoquinolin-2(1H)-yl]-3-(1-{[3-(propan-2-yloxy)tricyclo[3.3.1.1$^{3,7}$]dec-1-yl]methyl}-1H-pyrazol-4-yl)pyridine-2-carboxylic acid The title compound was prepared by substituting EXAMPLE 12B for EXAMPLE 2B in EXAMPLE 2C. $^1$H NMR (300 MHz, dimethylsulfoxide-d$_6$) δ ppm 12.86 (s, 1H), 8.04 (d, 1H), 7.79 (d, 1H), 7.70 (m, 2H), 7.61 (d, 1H), 7.53 (s, 1H), 7.41 (m, 4H), 6.94 (d, 2H), 4.94 (s, 2H), 3.86 (m, 4H), 3.00 (t, 2H), 2.11 (m, 2H), 1.62 (m, 2H), 1.49 (m, 3H), 1.37 (m, 7H), 0.98 (d, 6H).

Example 13

6-[8-(1,3-benzothiazol-2-ylcarbamoyl)-3,4-dihydroisoquinolin-2(1H)-yl]-3-[1-(2-oxatricyclo[3.3.1.1$^{3,7}$]dec-1-ylmethyl)-1H-pyrazol-4-yl]pyridine-2-carboxylic acid

Example 13A 2-oxatricyclo[3.3.1.1$^{3,7}$]dec-1-ylmethanol

To a solution of (oxatricyclo[3.3.1.1$^{3,7}$]dec-1-yl)-2-carboxylic acid (0.32 g) in diethyl ether (5 mL) was added lithium aluminum hydride (1.0M in tetrahydrofuran, 2.1 mL) at 0° C. The reaction was allowed to warm to room temperature and was stirred for 2 hours. The reaction was cooled to 0° C. and quenched with water (0.24 mL). 15% Aqueous NaOH (0.24 mL) was added followed by more water (0.72 mL). The reaction was stirred for 1 hour, and magnesium sulfate was added. The mixture was filtered and concentrated to provide the title compound.

Example 13B 1-(2-oxatricyclo[3.3.1.1$^{3,7}$]dec-1-ylmethyl)-4-(4,4,5,5-tetramethyl-1,3,2-dioxaborolan-2-yl)-1H-pyrazole The title compound was prepared by substituting EXAMPLE 13A for 1-adamantanemethanol and 4-(4,4,5,5-tetramethyl-1,3,2-dioxaborolan-2-yl)-1H-pyrazole for 3,5-dimethyl-4-(4,4,5,5-tetramethyl-1,3,2-dioxaborolan-2-yl)-1H-pyrazole in EXAMPLE 2A.

Example 13C tert-butyl 6-[8-(1,3-benzothiazol-2-ylcarbamoyl)-3,4-dihydroisoquinolin-2(1H)-yl]-3-[1-(2-oxatricyclo[3.3.1.1$^{3,7}$]dec-1-ylmethyl)-1H-pyrazol-4-yl]pyridine-2-carboxylate The title compound was prepared by substituting EXAMPLE 13B for EXAMPLE 2A in EXAMPLE 2B.

Example 13D

6-[8-(1,3-benzothiazol-2-ylcarbamoyl)-3,4-dihydroisoquinolin-2(1H)-yl]-3-[1-(2-oxatricyclo[3.3.1.1$^{3,7}$]dec-1-ylmethyl)-1H-pyrazol-4-yl]pyridine-2-carboxylic acid The title compound was prepared by substituting EXAMPLE 13C for EXAMPLE 2B in EXAMPLE 2C. $^1$H NMR (300 MHz, dimethylsulfoxide-d$_6$) δ ppm 12.85 (s, 1H), 8.04 (d, 1H), 7.80 (d, 1H), 7.72 (t, 2H), 7.61 (d, 1H), 7.52 (s, 1H), 7.42 (m, 4H), 6.94 (d, 1H), 4.94 (s, 2H), 3.99 (s, 1H), 3.94 (s, 2H), 3.87 (t, 2H), 3.00 (t, 2H), 2.07 (s, 2H), 1.74 (m, 4H), 1.55 (m, 6H).

Example 14

6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 14A methyl 2-(5-bromo-6-(tert-butoxycarbonyl)pyridin-2-yl)-4,4-dimethyl-1,2,3,4-tetrahydroisoquinoline-8-carboxylate Methyl 4,4-dimethyl-1,2,3,4-tetrahydroisoquinoline-8-carboxylate (500 mg), EXAMPLE 1D (572 mg), and triethylamine (0.545 mL) in anhydrous dimethylsulfoxide (6.5 mL) was heated to 100° C. overnight, and the mixture was then cooled to room temperature. The reaction was quenched by the addition of saturated aqueous sodium bicarbonate solution (15 mL) and ethyl acetate (15 mL). The layers were separated, and the aqueous layer was extracted with additional ethyl acetate (2×15 mL). The combined organics were dried with anhydrous sodium sulfate, filtered and concentrated under reduced pressure. The residue was purified by chromatography on silica gel with 0-40% ethyl acetate/hexanes to provide the title product.

Example 14B 2-(5-bromo-6-(tert-butoxycarbonyl)pyridin-2-yl)-4,4-dimethyl-1,2,3,4-tetrahydroisoquinoline-8-carboxylic acid To an ambient solution of EXAMPLE 14A (245 mg) in tetrahydrofuran (2.1 mL) was added a solution of LiOH (30.9 mg) in water (0.52 mL). The reaction was stirred overnight, diluted with 2 mL water and 2 mL ethyl acetate, and acidified to pH~3 with 10% aqueous HCl solution. The layers were separated, and the aqueous layer was extracted with additional ethyl acetate (2×8 mL). The combined organic layers were dried with anhydrous sodium sulfate, filtered and concentrated under reduced pressure to provide the title compound.

Example 14C tert-butyl 6-(8-(benzo[d]thiazol-2-ylcarbamoyl)-4,4-dimethyl-3,4-dihydroisoquinolin-2(1H)-yl)-3-bromopicolinate An ambient solution of EXAMPLE 14B (182 mg), benzo[d]thiazol-2-amine (71.1 mg), 1-ethyl-3-[3-(dimethylamino)propyl]-carbodiimide hydrochloride (113 mg), 1-hydroxybenzotriazole hydrate (91 mg), and N-methylmorpholine (0.065 mL) was stirred overnight. An additional 1 equivalent each of 1-ethyl-3-[3-(dimethylamino)propyl]-carbodiimide hydrochloride, N-methylmorpholine, 1-hydroxybenzotriazole hydrate, and 2-aminobenzothiazole were added, and the reaction was heated to 40° C. for 4 hours. The reaction mixture was cooled to room temperature and quenched by the addition of saturated aqueous bicarbonate solution and ethyl acetate. The layers were separated, and the aqueous was extracted with additional 2× ethyl acetate. The combined organics were dried with anhydrous sodium sulfate, filtered and concentrated under reduced pressure. The residue was purified by chromatography on silica gel with 0-50% ethyl acetate/hexanes to provide the title product.

Example 14D tert-butyl 6-(8-(benzo[d]thiazol-2-ylcarbamoyl)-4,4-dimethyl-3,4-dihydroisoquinolin-2(1H)-yl)-3-[5-methyl-1-(tricyclo[3.3.1.1$^{3,7}$]dec-1-ylmethyl)-1H-pyrazol-4-yl]picolinate A mixture of EXAMPLE 14C (70 mg), EXAMPLE 3D (63 mg), $K_3PO_4$ (87 mg), $Pd_2(dba)_3$ (2.7 mg), and 1,3,5,7-tetramethyl-6-tetradecyl-2,4,8-trioxa-6-phosphaadamantane (4.9 mg) in a reaction vial equipped with a magnetic stir bar was degassed with nitrogen. In a separate vial a 1:1 mixture of 1,4-dioxane and water (0.2 M total concentration) was degassed by a stream of nitrogen for 20 min. The solvent was transferred by syringe to the reaction vial containing the solid reactants. The reaction was heated to 90° C. for 4 hours. The reaction was quenched by the addition of saturated aqueous bicarbonate solution (5 mL) and ethyl acetate (5 mL). The layers were separated, and the aqueous was extracted with additional ethyl acetate (2×5 mL). The combined organics were dried with anhydrous sodium sulfate, filtered and concentrated under reduced pressure. The residue was purified by chromatography on silica gel (12 g) with 0-50% ethyl acetate/hexanes to provide the title product.

Example 14E

6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 14D for EXAMPLE 2B in EXAMPLE 2C. $^1$H NMR (300 MHz, dimethylsulfoxide-$d_6$) δ ppm 12.82 (s, 1H), 8.04 (d, 1H), 7.79 (d, 1H), 7.69 (d, 1H), 7.58 (d, 1H), 7.42 (m, 5H), 7.27 (s, 1H), 7.00 (d, 1H), 4.93 (s, 2H), 3.71 (s, 2H), 2.11 (s, 2H), 1.93 (s, 3H), 1.60 (m, 15H), 1.34 (s, 6H).

Example 15

6-[8-(1,3-benzothiazol-2-ylcarbamoyl)-3,4-dihydroisoquinolin-2(1H)-yl]-3-(1-{[3-(morpholin-4-yl)tricyclo[3.3.1.1$^{3,7}$]dec-1-yl]methyl}-1H-pyrazol-4-yl)pyridine-2-carboxylic acid

Example 15A

4-{3-[(4-iodo-1H-pyrazol-1-yl)methyl]tricyclo[3.3.1.1$^{3,7}$]dec-1-yl}morpholine The title compound was prepared by substituting morpholine for methanol in EXAMPLE 7B.

Example 15B tert-butyl 6-[8-(1,3-benzothiazol-2-ylcarbamoyl)-3,4-dihydroisoquinolin-2(1H)-yl]-3-(1-{[3-(morpholin-4-yl)tricyclo[3.3.1.1$^{3,7}$]dec-1-yl]methyl}-1H-pyrazol-4-yl)pyridine-2-carboxylate The title compound was prepared by substituting EXAMPLE 15A for EXAMPLE 4A in EXAMPLE 4C.

Example 15C

6-[8-(1,3-benzothiazol-2-ylcarbamoyl)-3,4-dihydroisoquinolin-2(1H)-yl]-3-(1-{[3-(morpholin-4-yl)tricyclo[3.3.1.1$^{3,7}$]dec-1-yl]methyl}-1H-pyrazol-4-yl)pyridine-2-carboxylic acid The title compound was prepared by substituting EXAMPLE 15B for EXAMPLE 2B in EXAMPLE 2C. $^1$H NMR (300 MHz, dimethylsulfoxide-$d_6$) δ ppm 12.85 (s, 1H), 9.15 (s, 1H), 8.03 (d, 1H), 7.79 (d, 1H), 7.71 (m, 2H), 7.62 (d, 1H), 7.57 (s, 1H), 7.41 (m, 4H), 6.96 (d, 1H), 4.95 (s, 2H), 3.94 (m, 6H), 3.40 (m, 2H), 3.05 (m, 4H), 2.25 (m, 4H), 1.86 (m, 2H), 1.70 (m, 4H), 1.38 (m, 6H).

Example 16

6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-5-methyl-1H-pyrazol-4-yl)pyridine-2-carboxylic acid

Example 16A (3-bromotricyclo[3.3.1.1$^{3,7}$]dec-1-yl)methanol

In a 250 ml round-bottomed flask, 3-bromoadamantane-1-carboxylic acid (7.89 g) was dissolved in tetrahydrofuran (30 mL). Borane tetrahydrofuran complex (1M in hexane, 60 mL) was added slowly. The mixture was stirred at room temperature overnight. Methanol (20 mL) was added to the solution slowly. After removal of the solvents, methanol (5 mL) was added to the oily residue. Removal of the solvent provided the title compound.

Example 16B

1-[(3-bromotricyclo[3.3.1.1$^{3,7}$]dec-1-yl)methyl]-1H-pyrazole

The title compound was prepared by substituting EXAMPLE 16A for 1-adamantanemethanol and pyrazole for 3,5-dimethyl-4-(4,4,5,5-tetramethyl-1,3,2-dioxaborolan-2-yl)-1H-pyrazole in EXAMPLE 2A.

Example 16C

1-[(3-methoxytricyclo[3.3.1.1$^{3,7}$]dec-1-yl)methyl]-1H-pyrazole

The title compound was prepared by substituting EXAMPLE 16B for EXAMPLE 7A in EXAMPLE 7B.

Example 16D

1-[(3-methoxytricyclo[3.3.1.1$^{3,7}$]dec-1-yl)methyl]-5-methyl-1H-pyrazole

The title compound was prepared by substituting EXAMPLE 16C for EXAMPLE 3A in EXAMPLE 3B.

Example 16E 4-iodo-1-[(3-methoxytricyclo[3.3.1.1$^{3,7}$]dec-1-yl)methyl]-5-methyl-1H-pyrazole A mixture of EXAMPLE 16D (0.116 g) and N-iodosuccinimide (0.11 g) in 1 mL DMF was stirred overnight. The mixture was taken up in ethyl acetate, and the resulting solution was washed three times with water, and brine, then dried with anhydrous sodium sulfate, filtered and concentrated under reduced pressure. The residue was purified by chromatography on silica gel with 0-50% ethyl acetate/hexanes to provide the title compound.

Example 16F tert-butyl 6-[8-(1,3-benzothiazol-2-ylcarbamoyl)-3,4-dihydroisoquinolin-2(1H)-yl]-3-(1-{[3-methoxytricyclo[3.3.1.1$^{3,7}$]dec-1-yl]methyl}-5-methyl-1H-pyrazol-4-yl)pyridine-2-carboxylate The title compound was prepared by substituting EXAMPLE 16E for EXAMPLE 4A in EXAMPLE 4C.

Example 16G

6-[8-(1,3-benzothiazol-2-ylcarbamoyl)-3,4-dihydroisoquinolin-2(1H)-yl]-3-(1-{[3-methoxytricyclo[3.3.1.1$^{3.7}$]dec-1-yl]methyl}-5-methyl-1H-pyrazol-4-yl)pyridine-2-carboxylic acid The title compound was prepared by substituting EXAMPLE 16F for EXAMPLE 2B in EXAMPLE 2C. $^1$H NMR (300 MHz, dimethylsulfoxide-d$_6$) δ ppm 12.85 (s, 1H), 8.03 (d, 1H), 7.79 (d, 1H), 7.61 (d, 1H), 7.42 (m, 5H), 7.27 (s, 1H), 6.94 (d, 1H), 4.95 (s, 2H), 3.89 (t, 2H), 3.79 (s, 2H), 3.08 (s, 3H), 3.01 (t, 2H), 2.12 (m, 5H), 1.49 (m, 12H).

Example 17

N-(1,3-benzothiazol-2-yl)-2-{6-[(methylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide EXAMPLE 3F (220 mg), methanesulfonamide (40 mg), N-(3-dimethylaminopropyl)-N'-ethylcarbodiimide hydrochloride (100 mg), and 4-(dimethylamino)pyridine (80 mg) were dissolved in dichloromethane (2.5 mL) and stirred at room temperature over the weekend. The reaction mixture was concentrated and purified by Prep HPLC using Gilson system eluting with 20-80% acetonitrile in 0.1% water. $^1$H NMR (400 MHz, dimethylsulfoxide-d$_6$) δ ppm 12.84 (br s, 1H), 11.83 (s, 1H), 8.01 (d, 1H), 7.77 (d, 1H), 7.61 (d, 1H), 7.52 (d, 1H), 7.44 (m, 2H), 7.36 (m, 2H), 7.26 (s, 1H), 6.96 (d, 1H), 4.95 (s, 2H), 3.92 (t, 2H), 3.69 (s, 2H), 3.10 (s, 3H), 3.02 (t, 2H), 2.10 (s, 3H), 1.90 (br s, 3H), 1.61 (br m, 3H), 1.50 (br m, 9H).

Example 18

N-(1,3-benzothiazol-2-yl)-2-{6-[(cyclopropylsulfonyl)carbamoyl]-5-[5-methyl-1-(tricyclo[3.3.1.1$^{3,7}$]dec-1-ylmethyl)-1H-pyrazol-4-yl]pyridin-2-yl}-1,2,3,4-tetrahydroisoquinoline-8-carboxamide The title compound was prepared by substituting cyclopropanesulfonamide for methanesulfonamide in EXAMPLE 17. $^1$H NMR (400 MHz, dimethylsulfoxide-d$_6$) δ ppm 12.85 (br s, 1H), 11.74 (s, 1H), 8.02 (d, 1H), 7.79 (d, 1H), 7.62 (d, 1H), 7.53 (d, 1H), 7.46 (m, 2H), 7.36 (m, 2H), 7.28 (s, 1H), 7.00 (d, 1H), 4.98 (s, 2H), 3.92 (t, 2H), 3.70 (s, 2H), 3.02 (t, 2H), 2.77 (m, 1H), 2.11 (s, 3H), 1.91 (br s, 3H), 1.62 (br m, 3H), 1.51 (br m, 9H), 1.00 (m, 2H), 0.90 (m, 2H).

Example 19

N-(1,3-benzothiazol-2-yl)-2-{5-[5-methyl-1-(tricyclo[3.3.1.1$^{3,7}$]dec-1-ylmethyl)-1H-pyrazol-4-yl]-6-(2H-tetrazol-5-yl)pyridin-2-yl}-1,2,3,4-tetrahydroisoquinoline-8-carboxamide Example 19A N-(benzo[d]thiazol-2-yl)-2-(5-bromo-6-cyanopyridin-2-yl)-1,2,3,4-tetrahydroisoquinoline-8-carboxamide The title compound was prepared by substituting 3-bromo-6-chloropicolinonitrile for EXAMPLE 1D in EXAMPLE 1E.

Example 19B

N-(1,3-benzothiazol-2-yl)-2-{5-[5-methyl-1-(tricyclo[3.3.1.1$^{3,7}$]dec-1-ylmethyl)-1H-pyrazol-4-yl]-6-[(cyano)-pyridin-2-yl]-1,2,3,4-tetrahydroisoquinoline-8-carboxamide A mixture of EXAMPLE 19A (0.245 g), EXAMPLE 3D (0.220 g), 1,3,5,7-tetramethyl-6-phenyl-2,4,8-trioxa-6-phosphaadamantane (0.021 g), potassium phosphate (0.375 g) and tris(dibenzylideneacetone)dipalladium(0) (0.011 g) were added to dioxane (1.3 mL) and water (1.3 mL). The reaction was degassed with nitrogen, sealed and heated to 90° C. After 2 hours the reaction was cooled, diluted with chloroform (40 mL) and washed with brine (30 mL). The reaction was dried over sodium sulfate, filtered, and concentrated. Silica gel chromatography eluting with a gradient of 5% to 45% ethyl acetate/hexanes over 30 minutes provided the title compound.

Example 19C

N-(1,3-benzothiazol-2-yl)-2-{5-[5-methyl-1-(tricyclo[3.3.1.1$^{3,7}$]dec-1-ylmethyl)-1H-pyrazol-4-yl]-6-(2H-tetrazol-5-yl)pyridin-2-yl}-1,2,3,4-tetrahydroisoquinoline-8-carboxamide EXAMPLE 19B (100 mg) was dissolved in N,N-dimethylformamide (1.5 mL), and sodium azide (96 mg) and triethylamine hydrochloride (196 mg) were added. The reaction was heated at 110° C. overnight. The reaction mixture was cooled, filtered, and purified by Prep HPLC using Gilson system eluting with 20-80% acetonitrile in water containing 0.1% trifluoroacetic acid. $^1$H NMR (400 MHz, dimethylsulfoxide-d$_6$) δ ppm 12.84 (br s, 1H), 8.03 (d, 1H), 7.79 (d, 1H), 7.62 (m, 2H), 7.46 (m, 2H), 7.36 (m, 2H), 7.20 (s, 1H), 7.05 (d, 1H), 4.99 (s, 2H), 4.01 (t, 2H), 3.67 (s, 2H), 3.03 (t, 2H), 1.92 (br s, 3H), 1.83 (s, 3H), 1.60 (br m, 6H), 1.48 (br m, 6H).

Example 20

6-[8-(1,3-benzothiazol-2-ylcarbamoyl)-3,4-dihydroisoquinolin-2(1H)-yl]-3-{2-methyl-4-[tricyclo[3.3.1.1$^{3,7}$]dec-1-ylmethoxy]phenyl}pyridine-2-carboxylic acid

Example 20A

1-[(4-bromo-3-methylphenoxy)methyl]tricyclo[3.3.1.1$^{3,7}$]decane

The title compound was prepared by substituting 4-bromo-3-methylphenol for 3,5-dimethyl-4-(4,4,5,5-tetramethyl-1,3,2-dioxaborolan-2-yl)-1H-pyrazole in EXAMPLE 2A.

Example 20B

3-{2-methyl-4-[tricyclo[3.3.1.1$^{3,7}$]dec-1-ylmethoxy]phenyl}-6-[8-(1,3-benzothiazol-2-ylcarbamoyl)-3,4-dihydroisoquinolin-2(1H)-yl]pyridine-2-carboxylic acid tert-butyl ester EXAMPLE 4B (120 mg), EXAMPLE 20A (90 mg), trans-dichlorobis(triphenylphosphine)palladium (II) (30 mg), and cesium carbonate (280 mg) were added to a microwave vial. N,N-dimethylformamide (1.0 mL), 1,4-dioxane (0.7 mL), and water (0.4 mL) were added. The vial was placed in a microwave reactor and subjected to 120° C. for 15 minutes. The solution was then added to water and extracted with 30% ethyl acetate in hexanes. The extract was washed with brine and dried over anhydrous sodium sulfate. The solution was filtered, concentrated and purified on silica gel using 30% ethyl acetate in hexanes.

Example 20C

6-[8-(1,3-benzothiazol-2-ylcarbamoyl)-3,4-dihydroisoquinolin-2(1H)-yl]-3-{2-methyl-4-[tricyclo[3.3.1.1$^{3,7}$]dec-1-ylmethoxy]phenyl}pyridine-2-carboxylic acid The title compound was prepared by substituting EXAMPLE 20B for EXAMPLE 2B in EXAMPLE 2C. $^1$H NMR (400 MHz, dimethylsulfoxide-d$_6$) δ ppm 12.85 (bs, 1H), 8.03 (d, 1H), 7.79 (d, 1H), 7.62 (d, 1H), 7.51-7.31 (m, 5H), 6.95 (d, 1H), 6.91 (d, 1H), 6.79 (d, 1H), 6.70 (dd, 1H), 4.97 (s, 2H), 3.91 (t, 2H), 3.51 (s, 2H), 3.03 (t, 2H), 2.02 (s, 3H), 1.98 (bs, 3H), 1.78-1.58 (m, 12H).

Example 21

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylmethoxy]phenyl}pyridine-2-carboxylic acid

Example 21A

1-[(3-bromo-2-methylphenoxy)methyl]tricyclo[3.3.1.1$^{3,7}$]decane

The title compound was prepared by substituting 3-bromo-2-methylphenol for 3,5-dimethyl-4-(4,4,5,5-tetramethyl-1,3,2-dioxaborolan-2-yl)-1H-pyrazole in EXAMPLE 2A.

Example 21B

3-{2-methyl-3-[tricyclo[3.3.1.1$^{3,7}$]dec-1-ylmethoxy]phenyl}-6-[8-(1,3-benzothiazol-2-ylcarbamoyl)-3,4-dihydroisoquinolin-2(1H)-yl]pyridine-2-carboxylic acid tert-butyl ester The title compound was prepared by substituting EXAMPLE 21A for EXAMPLE 20A in EXAMPLE 20B.

Example 21C

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylmethoxy]phenyl}pyridine-2-carboxylic acid The title compound was prepared by substituting EXAMPLE 21B for EXAMPLE 2B in EXAMPLE 2C. $^1$H NMR (400 MHz, dimethylsulfoxide-d$_6$) δ ppm 12.85 (bs, 1H), 8.04 (d, 1H), 7.79 (d, 1H), 7.62 (d, 1H), 7.51-7.31 (m, 5H), 7.08 (t, 1H), 6.98 (d, 1H), 6.84 (d, 1H), 6.62 (d, 1H), 4.98 (s, 2H), 3.92 (t, 2H), 3.52 (s, 2H), 3.03 (t, 2H), 1.99 (s, 3H), 1.92 (bs, 3H), 1.78-1.59 (m, 12H).

Example 22

6-[8-(1,3-benzothiazol-2-ylcarbamoyl)-3,4-dihydroisoquinolin-2(1H)-yl]-3-{3-[tricyclo[3.3.1.1$^{3,7}$]dec-1-ylmethoxy]phenyl}pyridine-2-carboxylic acid

Example 22A

1-[(3-bromophenoxy)methyl]tricyclo[3.3.1.1$^{3,7}$]decane

The title compound was prepared by substituting 3-bromophenol for 3,5-dimethyl-4-(4,4,5,5-tetramethyl-1,3,2-dioxaborolan-2-yl)-1H-pyrazole in EXAMPLE 2A.

Example 22B

3-{3-[tricyclo[3.3.1.1$^{3,7}$]dec-1-ylmethoxy]phenyl}-6-[8-(1,3-benzothiazol-2-ylcarbamoyl)-3,4-dihydroisoquinolin-2(1H)-yl]pyridine-2-carboxylic acid tert-butyl ester The title compound was prepared by substituting EXAMPLE 22A for EXAMPLE 20A in EXAMPLE 20B.

Example 22C

6-[8-(1,3-benzothiazol-2-ylcarbamoyl)-3,4-dihydroisoquinolin-2(1H)-yl]-3-{3-[tricyclo[3.3.1.1$^{3,7}$]dec-1-ylmethoxy]phenyl}pyridine-2-carboxylic acid The title compound was prepared by substituting EXAMPLE 22B for EXAMPLE 2B in EXAMPLE 2C. $^1$H NMR (400 MHz, dimethylsulfoxide-d$_6$) δ ppm 12.86 (bs, 1H), 8.04 (d, 1H), 7.80 (d, 1H), 7.67 (d, 1H), 7.62 (d, 1H), 7.50-7.43 (m, 2H), 7.39-7.33 (m, 2H), 7.29-7.23 (m, 1H), 6.97 (d, 1H), 6.90-6.83 (m, 3H), 4.98 (s, 2H), 3.90 (t, 2H), 3.52 (s, 2H), 3.02 (t, 2H), 1.98 (bs, 3H), 1.78-1.59 (m, 12H).

Example 23

6-[8-(1,3-benzothiazol-2-ylcarbamoyl)-3,4-dihydroisoquinolin-2(1H)-yl]-3-[5-cyano-2-methyl-1-(tricyclo[3.3.1.1$^{3,7}$]dec-1-ylmethyl)-1H-pyrrol-3-yl]pyridine-2-carboxylic acid

Example 23A

Ethyl 4-iodo-5-methyl-1H-pyrrole-2-carboxylate

The title compound was prepared by following the procedure described for EXAMPLE 16E and replacing EXAMPLE 16D with ethyl 5-methyl-1H-pyrrole-2-carboxylate.

Example 23B 4-iodo-5-methyl-1H-pyrrole-2-carboxylic acid

EXAMPLE 23A (1 g) in tetrahydrofuran (30 mL) and methanol (10 mL) was treated with 2 N NaOH (20 mL) overnight. The reaction mixture was cooled to 0° C., acidified to pH 5, diluted with water (30 mL) and concentrated to remove the organic solvent. The precipitates were collected by filtration, washed with water and dried over sodium sulfate to provide the title compound.

Example 23C 4-iodo-5-methyl-1H-pyrrole-2-carboxamide

To a solution of EXAMPLE 23B (7.7 g) in tetrahydrofuran (20 mL) at 0° C. was added carbonyldiimidazole (14.9 g). The resulting mixture was stirred at room temperature for 2 hours. The reaction mixture was cooled to 0° C. and ammonium hydroxide (3 mL) was added. The mixture was stirred at room temperature for 2 hours and concentrated. The residue was dissolved in ethyl acetate, washed with brine and concentrated to provide the title compound.

Example 23D 4-iodo-5-methyl-1H-pyrrole-2-carbonitrile

To a solution of EXAMPLE 23C (7.89 g) in DMF (80 mL) and pyridine (5 mL) at 0° C. was added dropwise oxalyl chloride (5.52 mL). The mixture was stirred at 0° C. for 30 minutes and ice-water was added to quench the reaction. The resulting mixture was diluted with ethyl acetate and washed with aqueous NaHCO$_3$ and water extensively. The organic layer was dried over Na$_2$SO$_4$, filtered, and concentrated. The residue was purified by flash column, eluting with dichloromethane to provide the title compound.

Example 23E 5-cyano-2-methyl-3-iodo-1-(tricyclo[3.3.1.1$^{3,7}$]dec-1-ylmethyl)-1H-pyrrole EXAMPLE 23D (170 mg), 1-bromomethyladamantane (840 mg) and tetrabutylammonium bromide (171 mg) in N,N-dimethylformamide (20 mL) was treated with sodium hydride (147 mg) at 80° C. overnight. The reaction mixture was cooled, diluted with ethyl acetate and washed with brine. The organic layer was concentrated. The residue was purified by flash chromatography (40% dichloromethane in hexanes) to provide the title compound.

Example 23F

3-[5-cyano-2-methyl-1-(tricyclo[3.3.1.1$^{3,7}$]dec-1-ylmethyl)-1H-pyrrol-3-yl]-6-[8-(benzothiazol-2-ylcarbamoyl)-3,4-dihydro-1H-isoquinolin-2-yl]-pyridine-2-carboxylic acid tert-butyl ester The title compound was prepared by substituting EXAMPLE 23E for EXAMPLE 20A in EXAMPLE 20B.

Example 23G

6-[8-(1,3-benzothiazol-2-ylcarbamoyl)-3,4-dihydroisoquinolin-2(1H)-yl]-3-[5-cyano-2-methyl-1-(tricyclo[3.3.1.1$^{3,7}$]dec-1-ylmethyl)-1H-pyrrol-3-yl]pyridine-2-carboxylic acid The title compound was prepared by substituting EXAMPLE 23F for EXAMPLE 2B in EXAMPLE 2C. $^1$H NMR (400 MHz, dimethylsulfoxide-d$_6$) δ ppm 12.86 (s, 2H), 8.04 (d, 1H), 7.79 (d, 1H), 7.62 (d, 1H), 7.42-7.53 (m, 3H), 7.33-7.39 (m, 2H), 6.95 (d, 1H), 6.82 (s, 1H), 4.96 (s, 2H), 3.89 (t, 2H), 3.74 (s, 2H), 3.01 (t, 2H), 2.09 (s, 3H), 1.96 (s, 3H), 1.62-1.69 (m, 3H), 1.53-1.60 (m, 9H).

Example 24

3-[5-methyl-1-(tricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid

Example 24A

3-[5-methyl-1-(tricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid tert-butyl ester The title compound was prepared by substituting thiazolo[5,4-b]pyridin-2-amine for thiazolo[4,5-b]pyridine-2-amine in EXAMPLE 30D.

Example 24B

3-[5-methyl-1-(tricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid The title compound was prepared by substituting EXAMPLE 24A for EXAMPLE 2B in EXAMPLE 2C. $^1$H NMR (400 MHz, dimethylsulfoxide-d$_6$) δ ppm 12.98 (s, 2H), 8.57-8.47 (m, 1H), 8.16 (d, 1H), 7.63 (d, 1H), 7.56-7.47 (m, 2H), 7.45 (d, 1H), 7.38 (t, 1H), 7.27 (s, 1H), 6.96 (d, 1H), 4.96 (s, 2H), 3.88 (t, 2H), 3.70 (s, 2H), 3.02 (t, 2H), 2.10 (s, 3H), 1.92 (s, 3H), 1.71-142 (m, 12H).

Example 25

6-[8-(1,3-benzothiazol-2-ylcarbamoyl)-3,4-dihydroisoquinolin-2(1H)-yl]-2'-(tricyclo[3.3.1.1$^{3,7}$]dec-1-ylmethoxy)-3,4'-bipyridine-2-carboxylic acid

Example 25A 2-(tricyclo[3.3.1.1$^{3,7}$]dec-1-ylmethoxy)-4-iodo-pyridine

1-Adamantanemethanol (0.820 g) and 2-fluoro-4-iodopyridine (0.22 g) in tetrahydrofuran (5 mL) was treated with sodium hydride (60% in mineral oil) (0.057) at room temperature for 6 hours. The reaction was quenched with ice-water and extracted with ethyl acetate (3×10 mL). The organic layer was dried over MgSO$_4$, filtered, and concentrated. The residue was purified by preparative TLC, eluting with petroleum ether/ethyl acetate (20/1) to provide the title compound.

Example 25B

2'-(tricyclo[3.3.1.1$^{3,7}$]dec-1-ylmethoxy)-6-[8-(benzothiazol-2-ylcarbamoyl)-3,4-dihydro-1H-isoquinolin-2-yl]-[3,4']bipyridinyl-2-carboxylic acid tert-butyl ester The title compound was prepared by substituting EXAMPLE 25A for EXAMPLE 20A in EXAMPLE 20B.

Example 25C

6-[8-(1,3-benzothiazol-2-ylcarbamoyl)-3,4-dihydroisoquinolin-2(1H)-yl]-2'-(tricyclo[3.3.1.1$^{3,7}$]dec-1-ylmethoxy)-3,4'-bipyridine-2-carboxylic acid The title compound was synthesized by substituting EXAMPLE 25B for EXAMPLE 2B in EXAMPLE 2C. $^1$H NMR (400 MHz, dimethylsulfoxide-d$_6$) δ ppm 12.89 (s, 1H), 8.09 (d, 1H), 8.04 (d, 1H), 7.79 (d, 1H), 7.73 (d, 1H), 7.63 (d, 1H), 7.44-7.49 (m, 2H), 7.34-7.39 (m, 2H), 7.00 (d, 1H), 6.90 (dd, 1H), 6.72 (s, 1H), 5.01 (s, 2H), 3.92 (t, 2H), 3.86 (s, 2H), 3.02 (t, 2H), 1.97 (s, 3H), 1.61-1.72 (m, 12H).

Example 26

6-[8-(1,3-benzothiazol-2-ylcarbamoyl)-3,4-dihydroisoquinolin-2(1H)-yl]-3-[1-({3-[2-(morpholin-4-yl)ethoxy]tricyclo[3.3.1.1$^{3,7}$]dec-1-yl}methyl)-1H-pyrazol-4-yl]pyridine-2-carboxylic acid

Example 26A 3-bromotricyclo[3.3.1.1$^{3,7}$]dec-1-ylmethyl-1H-pyrazole

The title compound was prepared by substituting pyrazole for 3,5-dimethyl-4-(4,4,5,5-tetramethyl-1,3,2-dioxaborolan-2-yl)-1H-pyrazole and 3-bromo-1-adamantanemethanol for 1-adamantanemethanol in EXAMPLE 2A.

Example 26B

3-[2-(morpholin-4-yl)ethoxy]tricyclo[3.3.1.1$^{3,7}$]dec-1-ylmethyl-1H-pyrazole

The title compound was prepared by substituting EXAMPLE 26A for EXAMPLE 7A and 2-morpholinoethanol for methanol in EXAMPLE 7B.

Example 26C 4-iodo-3-{[2-(morpholin-4-yl)ethoxy]tricyclo[3.3.1.1$^{3,7}$]dec-1-ylmethyl}-1H-pyrazole The title compound was prepared by substituting EXAMPLE 26B for EXAMPLE 3B and N-iodosuccinimide for N-bromosuccinimide in EXAMPLE 3C.

Example 26D tert-butyl 6-(8-(benzo[d]thiazol-2-ylcarbamoyl)-3,4-dihydroisoquinolin-2(1H)-yl)-3-(1-((3-[2-(morpholin-4-yl)ethoxy]tricyclo[3.3.1.1$^{3,7}$]dec-1-yl)methyl)-1H-pyrazol-4-yl)picolinate The title compound was prepared by substituting EXAMPLE 26C for EXAMPLE 4A in EXAMPLE 4C.

Example 26E

6-[8-(1,3-benzothiazol-2-ylcarbamoyl)-3,4-dihydroisoquinolin-2(1H)-yl]-3-[1-({3-[2-(morpholin-4-yl)ethoxy]tricyclo[3.3.1.1$^{3,7}$]dec-1-yl}methyl)-1H-pyrazol-4-yl]pyridine-2-carboxylic acid The title compound was prepared by substituting EXAMPLE 26D for EXAMPLE 2B in EXAMPLE 2C. $^1$H NMR (300 MHz, dimethylsulfoxide-d$_6$) δ ppm 12.86 (br. s, 1H), 8.04 (d, 1H), 7.80 (d, 1H), 7.71 (m, 2H), 7.61 (d, 1H), 7.55 (s, 1H), 7.41 (m, 4H), 6.95 (d, 1H), 4.95 (s, 2H), 3.90 (m, 6H), 3.66 (m, 4H), 3.09 (m, 8H), 2.17 (m, 2H), 1.69 (m, 2H), 1.47 (m, 10H).

Example 27

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylmethoxy)-3,4'-bipyridine-2-carboxylic acid

Example 27A 2-(tricyclo[3.3.1.1$^{3,7}$]dec-1-ylmethoxy)-4-iodo-3-methyl-pyridine 1-Hydroxylmethyladamantane (249 mg) was dissolved in tetrahydrofuran (3.5 mL) and NaH (24 mg) was added. After the gas evolution ceased, 2-fluoro-4-iodo-3-methylpyridine (237 mg) in tetrahydrofuran (1.5 mL) was added. The reaction mixture was stirred at room temperature for 0.5 hours, quenched with H$_2$O and extracted with ethyl acetate. The combined organic layers were washed with brine and concentrated. The residue was purified by preparative TLC, eluting with petroleum ether to provide the title compound.

Example 27B

2'-(tricyclo[3.3.1.1$^{3,7}$]dec-1-ylmethoxy)-6-[8-(benzothiazol-2-ylcarbamoyl)-3,4-dihydro-1H-isoquinolin-2-yl]-3'-methyl-[3,4']bipyridinyl-2-carboxylic acid tert-butyl ester The title compound was synthesized by substituting EXAMPLE 27A for EXAMPLE 20A in EXAMPLE 20B.

Example 27C

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylmethoxy)-3,4'-bipyridine-2-carboxylic acid The title compound was synthesized by substituting EXAMPLE 27B for EXAMPLE 2B in EXAMPLE 2C. $^1$H NMR (400 MHz, dimethylsulfoxide-d$_6$) δ ppm 7.88 (d, 1H), 7.71-7.73 (m, 1H), 7.44-7.47 (m, 1H), 7.28-7.35 (m, 3H), 7.17-7.25 (m, 3H), 6.95 (d, 1H), 6.52 (d, 1H), 5.07-5.16 (m, 2H), 3.81-3.84 (m, 4H), 3.04-3.05 (m, 2H), 1.89-1.93 (m, 6H), 1.61-1.69 (m, 12H).

Example 28

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid

Example 28A 1-(3-bromo-2-methylphenoxy)tricyclo[3.3.1.1$^{3,7}$]decane

3-Bromo-2-methylphenol (1000 mg) and 1-bromoadamantane (2013 mg) were added to hexamethylphosphoramide (8 mL) and the mixture was heated in a microwave reactor (Biotage) at 250° C. for 35 minutes. The solution was taken up in diethyl ether, washed with water two times, washed with brine, dried on anhydrous sodium sulfate, filtered, and concentrated. The crude material was purified by flash column chromatography on silica gel using 2% ethyl acetate (hexanes) increasing to 5% ethyl acetate (hexanes) to yield the title compound.

Example 28B

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid tert-butyl ester The title compound was prepared by substituting EXAMPLE 28A for EXAMPLE 20A in EXAMPLE 20B.

Example 28C

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid The title compound was prepared by substituting EXAMPLE 28B for EXAMPLE 2B in EXAMPLE 2C. $^1$H NMR (400 MHz, dimethylsulfoxide-d$_6$) δ ppm 12.85 (bs, 1H), 12.55 (bs, 1H), 8.03 (d, 1H), 7.79 (d, 1H), 7.62 (m, 2H), 7.50-7.32 (m, 4H), 7.08-6.95 (m, 3H), 6.73 (d, 1H), 4.98 (bs, 2H), 3.91 (m, 2H), 3.03 (t, 2H), 2.13 (bs, 3H), 1.93 (s, 3H), 1.86 (m, 6H), 1.59 (m, 6H).

Example 29

6-[8-(1,3-benzothiazol-2-ylcarbamoyl)-3,4-dihydroisoquinolin-2(1H)-yl]-3-{5-cyano-1-[tricyclo[3.3.1.1$^{3,7}$]dec-1-ylmethyl]-1H-pyrazol-4-yl}pyridine-2-carboxylic acid

Example 29A 4-bromo-5-cyano-1-[tricyclo[3.3.1.1$^{3,7}$]dec-1-ylmethyl]-1H-pyrazole The title compound was prepared by substituting 4-bromo-3-cyano-1H-pyrazole for 3,5-dimethyl-4-(4,4,5,5-tetramethyl-1,3,2-dioxaborolan-2-yl)-1H-pyrazole in EXAMPLE 2A.

Example 29B

6-[8-(1,3-benzothiazol-2-ylcarbamoyl)-3,4-dihydroisoquinolin-2(1H)-yl]-3-{5-cyano-1-[tricyclo[3.3.1.1$^{3,7}$]dec-1-ylmethyl]-1H-pyrazol-4-yl}pyridine-2-carboxylic acid tert-butyl ester The title compound was prepared by substituting EXAMPLE 29A for EXAMPLE 20A in EXAMPLE 20B.

Example 29C

6-[8-(1,3-benzothiazol-2-ylcarbamoyl)-3,4-dihydroisoquinolin-2(1H)-yl]-3-{5-cyano-1-[tricyclo[3.3.1.1$^{3,7}$]dec-1-ylmethyl]-1H-pyrazol-4-yl}pyridine-2-carboxylic acid The title compound was prepared by substituting EXAMPLE 29B for EXAMPLE 2B in EXAMPLE 2C. $^1$H NMR (400 MHz, dimethylsulfoxide-d$_6$) δ ppm 12.86 (bs, 1H), 8.04 (d, 1H), 7.79 (d, 1H), 7.68 (t, 2H), 7.63 (d, 1H), 7.50-7.38 (m, 4H), 7.06 (d, 1H), 5.01 (bs, 2H), 3.97 (s, 2H), 3.93 (t, 2H), 3.02 (t, 2H), 1.95 (bs, 3H), 1.68-1.50 (m, 12H).

Example 30

3-[5-methyl-1-(tricyclo[3.3.1.1$^{3,7}$]dec-1-ylmethyl)-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylic acid

Example 30A methyl 2-(5-bromo-6-(tert-butoxycarbonyl)pyridin-2-yl)-1,2,3,4-tetrahydroisoquinoline-8-carboxylate The title compound was prepared by substituting methyl 1,2,3,4-tetrahydroisoquinoline-8-carboxylate for EXAMPLE 1C in EXAMPLE 1E.

Example 30B

2-[6-tert-butoxycarbonyl-5-(1-tricyclo[3.3.1.1$^{3,7}$]
decan-1-ylmethyl-1 pyrazol-4-yl)-pyridin-2-yl]-1,2,
3,4-tetrahydro-isoquinoline-8-carboxylic acid methyl
ester The title compound was prepared by substituting EXAMPLE 30A for EXAMPLE 14C in EXAMPLE 14D.

Example 30C

2-[6-carboxy-5-(1-tricyclo[3.3.1.1$^{3,7}$]decan-1-ylmethyl-1 pyrazol-4-yl)-pyridin-2-yl]-1,2,3,4-tetrahydro-isoquinoline-8-carboxylic acid methyl ester EXAMPLE 30B (2.3 g) was dissolved in tetrahydrofuran (4.0 mL) and methanol (8.0 mL), and 1N LiOH (5.3 mL) was added. The mixture was stirred at room temperature for six days. The reaction mixture was diluted with water (50 mL), 2N aqueous HCl (2.65 mL) was added, and the mixture was stirred for a few minutes. The mixture was filtered, and the solid was washed with water, and dried under high vacuum in the presence of $P_2O_5$ overnight to provide the title compound.

Example 30D 3-(5-methyl-1-tricyclo[3.3.1.1$^{3,7}$]decan-1-ylmethyl-1H-pyrazol-4-yl)-6-[8-(thiazolo[4,5-b]pyridin-2-ylcarbamoyl)-3,4-dihydro-1H-isoquinolin-2-yl]-pyridine-2-carboxylic acid tert-butyl ester To a solution of EXAMPLE 30C (80 mg) and thiazolo[4,5-b]pyridine-2-amine (21 mg) in dichloromethane (1.5 mL) was added 1-ethyl-3-[3-(dimethylamino)propyl]-carbodiimide hydrochloride (40 mg) and 4-(dimethylamino)pyridine (26 mg). The mixture was stirred at room temperature overnight. The reaction mixture was then concentrated and purified by chromatography on silica gel using 1/4 hexanes/ethyl acetate to provide the title compound.

Example 30E

3-[5-methyl-1-(tricyclo[3.3.1.1$^{3,7}$]decan-1-ylmethyl)-1H-pyrazol-4-yl]-6-[8-(thiazolo[4,5-b]pyridin-2-ylcarbamoyl)-3,4-dihydroisoquinolin-2(1H)-yl]
pyridine-2-carboxylic acid EXAMPLE 30D (37 mg) was dissolved in dichloromethane (1.5 mL) and trifluoroacetic acid (1.5 mL). After stirring at room temperature overnight, the reaction mixture was concentrated and triturated with diethyl ether (5 mL) to provide the title compound. $^1$H NMR (500 MHz, dimethylsulfoxide-d$_6$) δ ppm 13.20 (br s, 1H), 8.61 (dd, 1H), 8.56 (dd, 1H), 7.65 (d, 1H), 7.51 (d, 1H), 7.45 (d, 1H), 7.39 (m, 2H), 7.27 (s, 1H), 6.96 (d, 1H), 4.97 (s, 2H), 3.89 (t, 2H), 3.70 (s, 2H), 3.02 (t, 2H), 2.10 (s, 3H), 1.92 (br s, 3H), 1.64 (br d, 3H), 1.54 (br m, 9H).

Example 31

3-[5-methyl-1-(tricyclo[3.3.1.1$^{3,7}$]dec-1-ylmethyl)-1H-pyrazol-4-yl]-6-[8-([1,3]thiazolo[4,5-c]pyridin-2-ylcarbamoyl)-3,4-dihydroisoquinolin-2(1H)-yl]
pyridine-2-carboxylic acid

Example 31A 3-(5-methyl-1-tricyclo[3.3.1.1$^{3,7}$]decan-1-ylmethyl-1H-pyrazol-4-yl)-6-[8-(thiazolo[4,5-c]pyridin-2-ylcarbamoyl)-3,4-dihydro-1H-isoquinolin-2-yl]-pyridine-2-carboxylic acid tert-butyl ester The title compound was prepared by substituting thiazolo[4,5-c]pyridine-2-amine for thiazolo[4,5-b]pyridine-2-amine in EXAMPLE 30D.

Example 31B

3-[5-methyl-1-(tricyclo[3.3.1.1$^{3,7}$]decan-1-ylmethyl)-1H-pyrazol-4-yl]-6-[8-(thiazolo[4,5-c]pyridin-2-ylcarbamoyl)-3,4-dihydroisoquinolin-2(1H)-yl]
pyridine-2-carboxylic acid The title compound was prepared by substituting EXAMPLE 31A for EXAMPLE 30D in EXAMPLE 30E. $^1$H NMR (500 MHz, dimethylsulfoxide-d$_6$) δ ppm 13.34 (br s, 1H), 9.30 (s, 1H), 8.59 (d, 1H), 8.45 (d, 1H), 7.65 (d, 1H), 7.50 (d, 1H), 7.47 (d, 1H), 7.40 (t, 1H), 7.27 (s, 1H), 6.96 (d, 1H), 4.97 (s, 2H), 3.89 (t, 2H), 3.70 (s, 2H), 3.02 (t, 2H), 2.10 (s, 3H), 1.92 (br s, 3H), 1.64 (br d, 3H), 1.54 (br m, 9H).

Example 32

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-5-methyl-1H-pyrazol-4-yl)pyridine-2-carboxylic acid

Example 32A 1-((3,5-dimethyltricyclo[3.3.1.1$^{3,7}$]dec-1-yl)methyl)-1H-pyrazole The title compound was prepared by substituting (3,5-dimethyladamantan-1-yl)methanol for 1-adamantanemethanol and pyrazole for 3,5-dimethyl-4-(4,4,5,5-tetramethyl-1,3,2-dioxaborolan-2-yl)-1H-pyrazole in EXAMPLE 2A.

Example 32B 1-((3,5-dimethyltricyclo[3.3.1.1$^{3,7}$]dec-1-yl)methyl)-5-methyl-1H-pyrazole To a solution of EXAMPLE 32A (2.44 g) in tetrahydrofuran (25 mL)/toluene (25 mL) was added n-butyllithium (7.49 mL) at −40° C. The reaction mixture was stirred for 60 minutes when CH$_3$I (1.873 mL) was added and the stirring was continued for 2 hours at −40° C. The reaction mixture was quenched with saturated ammonium chloride solution, extracted with ethyl acetate, dried over magnesium sulfate, filtered, concentrated and purified by flash chromotography (silica gel, 0%-15% ethyl acetate/hexanes).

Example 32C 3-bromo-1-((3,5-dimethyltricyclo[3.3.1.1$^{3,7}$]dec-1-yl)methyl)-5-methyl-1H-pyrazole The title compound was prepared by substituting EXAMPLE 32B for EXAMPLE 3B in EXAMPLE 3C.

Example 32D tert-butyl 6-(8-(benzo[d]thiazol-2-ylcarbamoyl)-3,4-dihydroisoquinolin-2(1H)-yl)-3-(1-((3,5-dimethyltricyclo[3.3.1.1$^{3,7}$]dec-1-yl)methyl)-5-methyl-1H-pyrazol-4-yl)picolinate The title compound was prepared by substituting EXAMPLE 32C for EXAMPLE 4A in EXAMPLE 4C.

Example 32E

6-[8-(1,3-benzothiazol-2-ylcarbamoyl)-3,4-dihydroisoquinolin-2(1H)-yl]-3-(1-{[3,5-dimethyltricyclo[3.3.1.1$^{3,7}$]dec-1-yl]methyl}-5-methyl-1H-pyrazol-4-yl)pyridine-2-carboxylic acid The title compound was prepared by substituting EXAMPLE 32D for EXAMPLE 2B in EXAMPLE 2C. $^1$H NMR (400 MHz, dimethylsulfoxide-d$_6$) δ ppm 12.85 (s, 1H), 8.04 (d, 1H), 7.79 (d, 1H), 7.62 (d, 1H), 7.48 (m, 3H), 7.40-7.31 (m, 2H), 7.27 (s, 1H), 6.95 (d, 1H), 4.95 (s, 2H), 3.88 (d, 2H), 3.74 (s, 2H), 3.01 (t, 2H), 2.09 (s, 3H), 2.04-1.97 (m, 1H), 1.33 (s, 2H), 1.24 (s, 4H), 1.21-0.98 (m, 6H), 0.78 (s, 7H).

Example 33

6-[8-(1,3-benzothiazol-2-ylcarbamoyl)-3,4-dihydroisoquinolin-2(1H)-yl]-3-(1-{[3-(1,1-dioxidothiomorpholin-4-yl)tricyclo[3.3.1.1$^{3,7}$]dec-1-yl]methyl})-1H-pyrazol-4-yl)pyridine-2-carboxylic acid Example 33A 4-(3-((4-iodo-1H-pyrazol-1-yl)methyl)tricyclo[3.3.1.1$^{3,7}$]dec-1-yl)-1,1-dioxidothiomorpholine The title compound was prepared by substituting thiomorpholine-1,1-dioxide for methanol in EXAMPLE 7B.

Example 33B tert-butyl 6-[8-(1,3-benzothiazol-2-ylcarbamoyl)-3,4-dihydroisoquinolin-2(1H)-yl]-3-(1-{[3-(1,1-dioxidothiomorpholin-4-yl)tricyclo[3.3.1.1$^{3,7}$]dec-1-yl]methyl}-1H-pyrazol-4-yl)picolinate The title compound was prepared by substituting EXAMPLE 33A for EXAMPLE 4A in EXAMPLE 4C.

Example 33C

6-[8-(1,3-benzothiazol-2-ylcarbamoyl)-3,4-dihydroisoquinolin-2(1H)-yl]-3-(1-{3-(1,1-dioxidothiomorpholin-4-yl)tricyclo[3.3.1.1$^{3,7}$]dec-1-yl]methyl})-1H-pyrazol-4-yl)pyridine-2-carboxylic acid The title compound was prepared by substituting EXAMPLE 33B for EXAMPLE 2B in EXAMPLE 2C. $^1$H NMR (300 MHz, dimethylsulfoxide-d$_6$) δ ppm 12.85 (br. s, 1H), 8.04 (d, 1H), 7.80 (d, 1H), 7.71 (m, 2H), 7.59 (m, 2H), 7.41 (m, 4H), 6.95 (d, 1H), 4.95 (s, 2H), 3.88 (m, 4H), 3.01 (m, 2H), 2.72 (m, 2H), 2.43 (m, 2H), 2.21 (m, 4H), 1.61 (m, 12H)

Example 34

6-[8-(1,3-benzothiazol-2-ylcarbamoyl)-3,4-dihydroisoquinolin-2(1H)-yl]-3-{5-cyano-2-methyl-1-[2-(tricyclo[3.3.1.1$^{3,7}$]dec-1-yl)ethyl]-1H-pyrrol-3-yl}pyridine-2-carboxylic acid Example 34A 5-cyano-2-methyl-1-[2-(tricyclo[3.3.1.1$^{3,7}$]dec-1-yl)ethyl]-1H-pyrrole The title compound was synthesized by substituting EXAMPLE 23D for 3,5-dimethyl-4-(4,4,5,5-tetramethyl-1,3,2-dioxaborolan-2-yl)-1H-pyrazole and adamantane-1-ethanol for 1-adamantanemethanol in EXAMPLE 2A.

Example 34B

3-[5-cyano-2-methyl-1-[2-(tricyclo[3.3.1.1$^{3,7}$]dec-1-yl)ethyl]-1H-pyrrol-3-yl]-6-[8-(benzothiazol-2-ylcarbamoyl)-3,4-dihydro-1H-isoquinolin-2-yl]-pyridine-2-carboxylic acid tert-butyl ester The title compound was prepared by substituting EXAMPLE 34A for EXAMPLE 20A in EXAMPLE 20B.

Example 34C

6-[8-(1,3-benzothiazol-2-ylcarbamoyl)-3,4-dihydroisoquinolin-2(1H)-yl]-3-{5-cyano-2-methyl-1-[2-(tricyclo[3.3.1.1$^{3,7}$]dec-1-yl)ethyl]-1H-pyrrol-3-yl}pyridine-2-carboxylic acid The title compound was prepared by substituting EXAMPLE 34B for EXAMPLE 2B in EXAMPLE 2C. $^1$H NMR (400 MHz, dimethylsulfoxide-d$_6$) δ ppm 12.85 (s, 1H), 8.04 (d, 1H), 7.79 (d, 1H), 7.62 (d, 1H), 7.41-7.51 (m, 3H), 7.33-7.39 (m, 2H), 6.95 (d, 1H), 6.78 (s, 1H), 4.96 (s, 2H), 3.96-4.04 (m, 2H), 3.89 (t, 2H), 3.01 (t, 2H), 2.10 (s, 3H), 1.95 (s, 3H), 1.53-1.73 (m, 12H), 1.33-1.44 (m, 2H).

Example 35

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(methylsulfonyl)carbamoyl]pyridin-2-yl}-1,2,3,4-tetrahydroisoquinoline-8-carboxamide The title compound was prepared by substituting EXAMPLE 23G for EXAMPLE 3F in EXAMPLE 17. $^1$H NMR (400 MHz, dimethylsulfoxide-d$_6$) δ ppm 12.86 (s, 1H), 11.82 (s, 1H), 8.03 (d, 1H), 7.79 (d, 1H), 7.62 (d, 1H), 7.54 (d, 1H), 7.42-7.50 (m, 2H), 7.32-7.40 (m, 2H), 7.00 (d, 1H), 6.82 (s, 1H), 4.96 (s, 2H), 3.94 (t, 2H), 3.73 (s, 2H), 3.13 (s, 3H), 3.03 (t, 2H), 2.10 (s, 3H), 1.95 (s, 3H), 1.50-1.70 (m, 12H).

Example 36

N-(1,3-benzothiazol-2-yl)-2-{5-[5-cyano-2-methyl-1-(tricyclo[3.3.1.1$^{3,7}$]dec-1-ylmethyl)-1H-pyrrol-3-yl]-6-[(cyclopropylsulfonyl)carbamoyl]pyridin-2-yl}-1,2,3,4-tetrahydroisoquinoline-8-carboxamide The title compound was prepared by substituting EXAMPLE 23G for EXAMPLE 3F and cyclopropanesulfonamide for methanesulfonamide in EXAMPLE 17. $^1$H NMR (400 MHz, dimethylsulfoxide-d$_6$) δ ppm 12.86 (s, 1H), 11.74 (s, 1H), 8.02 (d, 1H), 7.79 (d, 1H), 7.62 (d, 1H), 7.54 (d, 1H), 7.42-7.50 (m, 2H), 7.32-7.40 (m, 2H), 7.01 (d, 1H), 6.82 (s, 1H), 4.99 (s, 2H), 3.93 (t, 2H), 3.73 (s, 2H), 3.03 (t, 2H), 2.74-2.84 (m, 1H), 2.11 (s, 3H), 1.94 (s, 3H), 1.52-1.68 (m, 12H), 0.99-1.05 (m, 2H), 0.87-0.95 (m, 2H).

Example 37

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(methylsulfonyl)carbamoyl]pyridin-2-yl}-1,2,3,4-tetrahydroisoquinoline-8-carboxamide The title compound was prepared by substituting EXAMPLE 16G for EXAMPLE 3F in EXAMPLE 17. $^1$H NMR (300 MHz, dimethylsulfoxide-d$_6$) δ ppm 12.86 (br. s, 1H), 11.81 (s, 1H), 8.03 (d, 1H), 7.79 (d, 1H), 7.63 (d, 1H), 7.54 (d, 1H), 7.46 (m, 2H), 7.36 (m, 2H), 7.28 (s, 1H), 7.00 (d, 1H), 4.96 (s, 2H), 3.93 (m, 2H), 3.80 (s, 3H), 3.12 (s, 3H), 3.08 (s, 3H), 3.02 (m, 2H), 2.13 (m, 4H), 1.49 (m, 12H).

Example 38

6-[8-(1,3-benzothiazol-2-ylcarbamoyl)-3,4-dihydroisoquinolin-2(1H)-yl]-3-(1-{[3-methoxy-5,7-dimethyltricyclo[3.3.1.1$^{3,7}$]dec-1-yl]methyl}-5-methyl-1H-pyrazol-4-yl)pyridine-2-carboxylic acid

Example 38A 5-bromo-3,7-dimethyltricyclo[3.3.1.1$^{3,7}$]decane-1-carboxylic acid In a 50 mL round-bottomed flask, bromine (3 mL) was cooled to 0° C. and iron (0.56 g) was added. The mixture was stirred at 0° C. for 30 minutes. 3,5-dimethyladamantane-1-carboxylic acid (0.5 g) was added. The mixture was stirred at room temperature overnight. After adding ice and 6N aqueous HCl (10 mL), ethyl acetate (20 mL), and saturated aqueous Na$_2$SO$_3$ were added. The aqueous layer was extracted twice with ethyl acetate. The combined organic layers were washed with saturated Na$_2$SO$_3$ (50 mL, 3×) and dried over Na$_2$SO$_4$. After filtration and removal of the solvent, the product was used directly in the next step.

Example 38B 5-bromo-3,7-dimethyltricyclo[3.3.1.1$^{3,7}$]dec-1-yl-methanol

The title compound was prepared by substituting EXAMPLE 38A for 3,5,8-trimethyl-1-adamantane carboxylic acid in EXAMPLE 9A.

Example 38C 1-(5-bromo-3,7-dimethyltricyclo[3.3.1.1$^{3,7}$]dec-1-yl)-1H-pyrazole The title compound was prepared by substituting pyrazole for 3,5-dimethyl-4-(4,4,5,5-tetramethyl-1,3,2-dioxaborolan-2-yl)-1H-pyrazole and EXAMPLE 38B for 1-adamantanemethanol in EXAMPLE 2A.

Example 38D 1-(5-methoxy-3,7-dimethyltricyclo[3.3.1.1$^{3,7}$]dec-1-yl)-1H-pyrazole The title compound was prepared by substituting EXAMPLE 38C for EXAMPLE 7A in EXAMPLE 7B.

Example 38E 1-(5-methoxy-3,7-dimethyltricyclo[3.3.1.1$^{3,7}$]dec-1-yl)-5-methyl-1H-pyrazole The title compound was prepared by substituting EXAMPLE 38C for EXAMPLE 3A in EXAMPLE 3B.

Example 38F 4-bromo-1-(5-methoxy-3,7-dimethyltricyclo[3.3.1.1$^{3,7}$]dec-1-yl)-5-methyl-1H-pyrazole The title compound was prepared by substituting EXAMPLE 38E for EXAMPLE 3B in EXAMPLE 3C.

Example 38G tert-butyl 6-[8-(1,3-benzothiazol-2-ylcarbamoyl)-3,4-dihydroisoquinolin-2(1H)-yl]-3-(1-(5-methoxy-3,7-dimethyltricyclo[3.3.1.1$^{3,7}$]dec-1-yl)-5-methyl-1H-pyrazol-4-yl)picolinate The title compound was prepared by substituting EXAMPLE 38F for EXAMPLE 4A in EXAMPLE 4C.

Example 38H

6-[8-(1,3-benzothiazol-2-ylcarbamoyl)-3,4-dihydroisoquinolin-2(1H)-yl]-3-(1-(5-methoxy-3,7-dimethyltricyclo[3.3.1.1$^{3,7}$]dec-1-yl)-5-methyl-1H-pyrazol-4-yl)pyridine-2-carboxylic acid The title compound was prepared by substituting EXAMPLE 38G for EXAMPLE 2B in EXAMPLE 2C. $^1$H NMR (300 MHz, dimethylsulfoxide-d$_6$) δ ppm 12.84 (br. s, 1H), 8.03 (d, 1H), 7.79 (d, 1H), 7.61 (d, 1H), 7.42 (m, 5H), 7.28 (s, 1H), 6.95 (d, 1H), 4.95 (s, 2H), 3.89 (t, 2H), 3.82 (s, 2H), 3.08 (s, 3H), 3.01 (t, 2H), 2.09 (s, 3H), 1.34 (s, 2H), 1.12 (m, 10H), 0.85 (s, 6H).

Example 39

N-(1,3-benzothiazol-2-yl)-2-{5-(1-{[3-methoxytricyclo[3.3.1.1$^{3,7}$]dec-1-yl]methyl}-5-methyl-1H-pyrazol-4-yl)-6-[(morpholin-4-ylsulfonyl)carbamoyl]pyridin-2-yl}-1,2,3,4-tetrahydroisoquinoline-8-carboxamide The title compound was prepared by substituting EXAMPLE 16G for EXAMPLE 3F and morpholine-4-sulfonamide for methanesulfonamide in EXAMPLE 17. ¹H NMR (300 MHz, dimethylsulfoxide-$d_6$) δ ppm 12.85 (br. s, 1H), 11.64 (s, 1H), 8.02 (d, 1H), 7.79 (d, 1H), 7.63 (d, 1H), 7.44 (m, 5H), 7.27 (s, 1H), 7.01 (d, 1H), 4.99 (s, 2H), 3.91 (t, 2H), 3.79 (s, 2H), 3.12 (m, 4H), 3.08 (s, 3H), 3.02 (t, 2H), 2.12 (m, 5H), 1.48 (m, 12H).

Example 40

N-(1,3-benzothiazol-2-yl)-2-[5-(1-{[3-methoxytricyclo[3.3.1.1$^{3,7}$]dec-1-yl]methyl}-5-methyl-1H-pyrazol-4-yl)-6-{[(trifluoromethyl)sulfonyl]carbamoyl}pyridin-2-yl]-1,2,3,4-tetrahydroisoquinoline-8-carboxamide The title compound was prepared by substituting EXAMPLE 16G for EXAMPLE 3F and trifluoromethanesulfonamide for methanesulfonamide in EXAMPLE 17. ¹H NMR (300 MHz, dimethylsulfoxide-$d_6$) δ ppm 12.84 (br. s, 1H), 8.03 (d, 1H), 7.79 (d, 1H), 7.64 (d, 1H), 7.57 (d, 1H), 7.47 (m, 2H), 7.35 (m, 3H), 6.98 (d, 1H), 4.95 (s, 2H), 3.92 (t, 2H), 3.05 (m, 5H), 2.13 (m, 5H), 1.48 (m, 12H).

Example 41

N-(1,3-benzothiazol-2-yl)-2-{6-[(cyclopropylsulfonyl)carbamoyl]-5-(1-{[3-methoxytricyclo[3.3.1.1$^{3,7}$]dec-1-yl]methyl}-5-methyl-1H-pyrazol-4-yl)pyridin-2-yl}-1,2,3,4-tetrahydroisoquinoline-8-carboxamide The title compound was prepared by substituting EXAMPLE 16G for EXAMPLE 3F and cyclopropanesulfonamide for methanesulfonamide in EXAMPLE 17. ¹H NMR (300 MHz, dimethylsulfoxide-$d_6$) δ ppm 12.86 (br. s, 1H), 11.74 (s, 1H), 8.03 (d, 1H), 7.79 (d, 1H), 7.62 (d, 1H), 7.53 (d, 1H), 7.46 (m, 2H), 7.36 (m, 2H), 7.29 (s, 1H), 7.01 (d, 1H), 4.98 (s, 2H), 3.93 (t, 2H), 3.79 (s, 3H), 3.08 (s, 3H), 3.03 (t, 2H), 2.11 (m, 5H), 1.50 (m, 12H), 0.96 (m, 4H).

Example 42

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid

Example 42A 5-chloro-1-[tricyclo[3.3.1.1$^{3,7}$]dec-1-ylmethyl]-1H-pyrazole The title compound was prepared by substituting hexachloroethane for iodomethane in EXAMPLE 3B.

Example 42B 4-bromo-5-chloro-1-[tricyclo[3.3.1.1$^{3,7}$]dec-1-ylmethyl]-1H-pyrazole The title compound was prepared by substituting EXAMPLE 42A for EXAMPLE 3B in EXAMPLE 3C.

Example 42C

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid tert-butyl ester The title compound was prepared by substituting EXAMPLE 42B for EXAMPLE 20A in EXAMPLE 20B.

Example 42D

6-[8-(1,3-benzothiazol-2-ylcarbamoyl)-3,4-dihydroisoquinolin-2(1H)-yl]-3-{5-chloro-1-[tricyclo[3.3.1.1$^{3,7}$]dec-1-ylmethyl]-1H-pyrazol-4-yl}pyridine-2-carboxylic acid The title compound was prepared by substituting EXAMPLE 42C for EXAMPLE 2B in EXAMPLE 2C. ¹H NMR (400 MHz, dimethylsulfoxide-$d_6$) δ ppm 12.85 (bs, 1H), 8.04 (d, 1H), 7.79 (d, 1H), 7.62 (d, 1H), 7.59 (d, 1H), 7.51-7.43 (m, 3H), 7.37 (m, 2H), 7.00 (d, 1H), 4.98 (bs, 2H), 3.93 (t, 2H), 3.81 (s, 2H), 3.02 (t, 2H), 1.93 (bs, 3H), 1.68-1.50 (m, 12H).

Example 43

6-[8-(1,3-benzothiazol-2-ylcarbamoyl)-1-methyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 43A 2-(tert-butoxycarbonyl)-1-methyl-1,2,3,4-tetrahydroisoquinoline-8-carboxylic acid To a solution of 2-(tert-butoxycarbonyl)-1,2,3,4-tetrahydroisoquinoline-8-carboxylic acid (2.25 g) and tetramethylethylenediamine (1.347 mL) in tetrahydrofuran (40 mL) was added dropwise t-butyllithium (1.6M, 15.21 mL) at −78° C. The mixture was stirred at −78° C. for 40 minutes. To the resulting mixture was added iodomethane (5.07 mL) dropwise and the mixture was stirred at −78° C. for 3 hours, followed by stirring at room temperature overnight. The reaction mixture was quenched with saturated ammonium chloride. The reaction mixture was extracted with ethyl acetate (150 mL), washed with brine (40 mL×3), dried over $Na_2SO_4$, filtered, and concentrated. The crude product was purified by flash chromatography (silica gel, 10% methanol/dichloromethane).

Example 43B tert-butyl 8-(benzo[d]thiazol-2-ylcarbamoyl)-1-methyl-3,4-dihydroisoquinoline-2(1H)-carboxylate A mixture of EXAMPLE 43A (400 mg), PyBOP (benzotriazol-1-yloxytripyrrolidinophosphonium hexafluorophosphate, 714 mg), triethylamine (0.383 mL) and benzo[d]thiazol-2-amine (247 mg) in dichloromethane (10 mL) was stirred overnight at room temperature. The mixture was diluted with ethyl acetate (100 mL), washed with brine (30 mL×3), dried over $Na_2SO_4$, filtered, concentrated and purified by flash chromatography (silica gel, petroleum ether/ethyl acetate=1/1).

Example 43C

N-(benzo[d]thiazol-2-yl)-1-methyl-1,2,3,4-tetrahydroisoquinoline-8-carboxamide

A solution of EXAMPLE 43B (150 mg) in dichloromethane (10 mL) was treated with TFA (1 mL). The reaction mixture was stirred for 2 hours at 30° C. The reaction mixture was diluted with ethyl acetate (100 mL), washed with saturated NaHCO$_3$, brine, dried over Na$_2$SO$_4$, filtered and concentrated. The crude product was purified by flash chromotography (silica gel, dichloromethane/methanol=10/1).

Example 43D methyl 6-(8-(benzo[d]thiazol-2-ylcarbamoyl)-1-methyl-1,2,3,4-tetrahydroisoquinolin-2(1H)-yl)-3-bromopicolinate A solution of EXAMPLE 43C (1 g), methyl 3-bromo-6-fluoropicolinate (0.715 g) and triethylamine (0.775 mL) in 12 mL DMSO was heated at 70° C. overnight followed by heating at 105° C. for 4 hours. The reaction mixture was diluted with ethyl acetate, washed 3 times with water, washed with brine, dried over Na$_2$SO$_4$, filtered, and concentrated. The crude material was purified by flash chromotography (silica gel, 5-25% ethyl acetate/hexanes).

Example 43E methyl 6-(8-(benzo[d]thiazol-2-ylcarbamoyl)-1-methyl-3,4-dihydroisoquinolin-2(1H)-yl)-3-(1-(tricyclo[3.3.1.1$^{3,7}$]dec-1-ylmethyl)-5-methyl-1H-pyrazol-4-yl)picolinate The title compound was prepared by substituting EXAMPLE 43D for EXAMPLE 4A and EXAMPLE 3D for EXAMPLE 4B in EXAMPLE 4C.

Example 43F

6-[8-(1,3-benzothiazol-2-ylcarbamoyl)-1-methyl-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 43E for EXAMPLE 14A in EXAMPLE 14B. $^1$H NMR (dimethylsulfoxide-d$_6$) δ ppm 12.67 (s, 1H), 8.01 (d, 1H), 7.78 (d, 1H), 7.55 (d, 1H), 7.51-7.39 (m, 3H), 7.34 (dt, 3H), 6.77 (d, 1H), 6.13 (d, 1H), 4.11-3.96 (m, 1H), 3.70 (s, 2H), 3.66-3.54 (m, 2H), 3.06 (t, 2H), 2.13 (s, 3H), 1.93 (s, 3H), 1.67 (s, 1H), 1.63 (s, 2H), 1.58 (s, 2H), 1.53 (s, 6H), 1.41 (d, 3H).

Example 44

6-[8-(1,3-benzothiazol-2-ylcarbamoyl)-1,1-dideutero-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 44A 2-(tert-butoxycarbonyl)-1,1-dideutero-1,2,3,4-tetrahydroisoquinoline-8-carboxylic acid To a tetrahydrofuran (40 mL) solution of 2-(tert-butoxycarbonyl)-1,2,3,4-tetrahydroisoquinoline-8-carboxylic acid (5 g) and tetramethylethylenediamine (2.99 mL) was added dropwise t-butyllithium (1.7 M, 39.4 mL) at −78° C. The mixture was stirred at −78° C. for 3 hours. To the resulting mixture, D$_2$O (0.979 mL) was added dropwise and the reaction mixture was stirred at −78° C. for 2 hours. The mixture was diluted with ethyl acetate (150 mL), washed with brine, dried over Na$_2$SO$_4$, filtered, and concentrated. The crude product was used in next step without further purification. This procedure was repeated on the same material 5 times.

Example 44B tert-butyl 8-(benzo[d]thiazol-2-ylcarbamoyl)-1,1-dideutero-1,2,3,4-tetrahydroisoquinoline-carboxylate A mixture of triethylamine (1.753 g), (1H-benzo[d][1,2,3]triazol-1-yloxy)tripyrrolidin-1-ylphosphonium hexafluorophosphate(V) (4.51 g), EXAMPLE 44A (2.42 g) and benzo[d]thiazol-2-amine (1.952 g) in dichloromethane (50 mL) was stirred overnight at 30° C. The reaction mixture was diluted with dichloromethane (200 mL), washed with brine, dried over Na$_2$SO$_4$, filtered, and concentrated. The crude product was purified by flash chromatography (silica gel, 30%—50% ethyl acetate/petroleum ether).

Example 44C

N-(benzo[d]thiazol-2-yl)-1,1-dideutero-1,2,3,4-tetrahydroisoquinoline-8-carboxamide The title compound was prepared by substituting EXAMPLE 44B for EXAMPLE 43B in EXAMPLE 43C.

Example 44D methyl 6-(8-(benzo[d]thiazol-2-ylcarbamoyl)-1,1-dideutero-1,2,3,4-tetrahydroisoquinolin-yl)-3-bromopicolinate The title compound was prepared by substituting EXAMPLE 44C for EXAMPLE 43C in EXAMPLE 43D.

Example 44E methyl 6-[8-(1,3-benzothiazol-2-ylcarbamoyl)(1,1-dideutero-1,2,3,4-tetrahydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylate The title compound was prepared by substituting EXAMPLE 44D for EXAMPLE 4A and EXAMPLE 3D for EXAMPLE 4B in EXAMPLE 4C.

Example 44F

6-[8-(1,3-benzothiazol-2-ylcarbamoyl)(1,1-$^2$H$_2$)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 44E for EXAMPLE 14A in EXAMPLE 14B. $^1$H NMR (400 MHz, dimethylsulfoxide-d$_6$) δ ppm 12.79 (s, 2H), 8.04 (d, 1H), 7.79 (d, 1H), 7.62 (d, 1H), 7.52-7.40 (m, 3H), 7.36 (m, 2H), 7.26 (s, 1H), 6.94 (d, 1H), 4.02 (s, 1H), 3.89 (dd, 2H), 3.70 (s, 2H), 3.01 (t, 2H), 2.10 (s, 3H), 1.92 (s, 3H), 1.67 (s, 1H), 1.63 (s, 2H), 1.57 (s, 2H), 1.52 (s, 6H).

Example 45

6-[8-(1,3-benzothiazol-2-ylcarbamoyl)-3,4-dihydroisoquinolin-2(1H)-yl]-3-(1-{[3-(2-methoxyethoxy)tricyclo[3.3.1.1$^{3,7}$]dec-1-yl]methyl}-5-methyl-1H-pyrazol-4-yl)pyridine-2-carboxylic acid

Example 45A 1-(5-(2-methoxyethoxy)-3,7-dimethyltricyclo[3.3.1.1$^{3,7}$]dec-1-yl)-1H-pyrazole The title compound was prepared by substituting EXAMPLE 26A for EXAMPLE 7A and 2-methoxyethanol for methanol in EXAMPLE 7B.

Example 45B 1-((5-2-methoxyethoxy)-3,7-dimethyltricyclo[3.3.1.1$^{3,7}$]dec-1-yl)-5-methyl-1H-pyrazole The title compound was prepared by substituting EXAMPLE 45A for EXAMPLE 3A in EXAMPLE 3B.

Example 45C 4-bromo-1-((5-2-methoxyethoxy)-3,7-dimethyltricyclo[3.3.1.1$^{3,7}$]dec-1-yl)-5-methyl-1H-pyrazole The title compound was prepared by substituting EXAMPLE 45B for EXAMPLE 3B in EXAMPLE 3C.

Example 45D tert-butyl 6-[8-(1,3-benzothiazol-2-ylcarbamoyl)-3,4-dihydroisoquinolin-2(1H)-yl]-3-(1-(5-(2-methoxyethoxy)-3,7-dimethyltricyclo[3.3.1.1$^{3,7}$]dec-1-yl)-5-methyl-1H-pyrazol-4-yl)picolinate The title compound was prepared by substituting EXAMPLE 45C for EXAMPLE 4A in EXAMPLE 4C.

Example 45E

6-[8-(1,3-benzothiazol-2-ylcarbamoyl)-3,4-dihydroisoquinolin-2(1H)-yl]-3-(1-(5-(2-methoxyethoxy)-3,7-dimethyltricyclo[3.3.1.1$^{3,7}$]dec-1-yl)-5-methyl-1H-pyrazol-4-yl)pyridine-2-carboxylic acid The title compound was prepared by substituting EXAMPLE 45D for EXAMPLE 2B in EXAMPLE 2C. $^1$H NMR (300 MHz, dimethylsulfoxide-d$_6$) δ ppm 12.86 (br. s, 1H), 8.04 (d, 1H), 7.79 (d, 1H), 7.62 (d, 1H), 7.42 (m, 5H), 7.28 (s, 1H), 6.94 (d, 1H), 4.95 (s, 2H), 3.89 (t, 2H), 3.78 (s, 2H), 3.21 (s, 3H), 3.01 (t, 2H), 2.11 (m, 5H), 1.50 (m, 12H).

Example 46

6-[8-(1,3-benzothiazol-2-ylcarbamoyl)-3,4-dihydroisoquinolin-2(1H)-yl]-3-(1-{[1-(2-methoxyethyl)cyclooctyl]methyl}-5-methyl-1H-pyrazol-4-yl)pyridine-2-carboxylic acid

Example 46A methyl cyclooctanecarboxylate

To a solution of cyclooctanecarbaldehyde (5.0 g) in methanol (300 mL) was added Oxone (22 g). The mixture was stirred at room temperature for 18 hours. The reaction mixture was concentrated under vacuum and the residue was diluted with ethyl acetate (300 mL) and washed with 1N aqueous HCl, water, and brine, dried over Na$_2$SO$_4$, filtered, and concentrated under reduced pressure to give the crude product.

Example 46B methyl 1-(2-methoxyethyl)cyclooctanecarboxylate

To a cooled (−78° C.) solution of lithium diisopropylamide (2.0M, 20 mL) in tetrahydrofuran (20 mL) was added EXAMPLE 46A (5.27 g) in tetrahydrofuran (20 mL). The mixture was stirred at −78° C. for 30 minutes and a solution of 1-bromo-3-methoxypropane (4.3 g) in tetrahydrofuran (10 mL) was added to the mixture. The mixture was stirred overnight and the temperature was allowed to warm up to room temperature. The mixture was quenched with aqueous NH$_4$Cl and extracted with ethyl acetate (300 mL) and washed with water (3×) and brine and dried over Na$_2$SO$_4$. Filtration and concentration of the solvent gave the crude product which was used in the next reaction without further purification.

Example 46C (1-(2-methoxyethyl)cyclooctyl)methanol

A solution of EXAMPLE 46B (6.5 g) in ether (50 mL) was added dropwise to a suspension of LiAlH$_4$ (1.2 g) in ether (60 mL). Once the addition was finished, the mixture was refluxed for 90 minutes, cooled to 0° C. and 2N aqueous NaOH (50 mL) was added slowly. The mixture was then extracted with ethyl acetate (300 mL) and the organic layer was washed with brine and dried over Na$_2$SO$_4$. Filtration and evaporation of the solvent provided the title compound.

Example 46D 1-((1-(2-methoxyethyl)cyclooctyl)methyl)-1H-pyrazole

The title compound was prepared by substituting EXAMPLE 46C for 1-adamantanemethanol and 1H-pyrazole for 3,5-dimethyl-4-(4,4,5,5-tetramethyl-1,3,2-dioxaborolan-2-yl)-1H-pyrazole in EXAMPLE 2A.

Example 46E 1-((1-(2-methoxyethyl)cyclooctyl)methyl)-5-methyl-1H-pyrazole

The title compound was prepared by substituting EXAMPLE 46D for EXAMPLE 3A in EXAMPLE 3B.

Example 46F 4-iodo-1-((1-(2-methoxyethyl)cyclooctyl)methyl)-5-methyl-1H-pyrazole The title compound was prepared by substituting EXAMPLE 46E for EXAMPLE 16D in EXAMPLE 16E.

Example 46G

6-[8-(1,3-benzothiazol-2-ylcarbamoyl)-3,4-dihydroisoquinolin-2(1H)-yl]-3-(1-{[1-(2-methoxyethyl)cyclooctyl]methyl}-5-methyl-1H-pyrazol-4-yl)pyridine-2-carboxylic acid The title compound was prepared by substituting EXAMPLE 46F for EXAMPLE 4A in EXAMPLE 4B, then substituting that product for EXAMPLE 2B in EXAMPLE 2C. $^1$H NMR (300 MHz, dimethylsulfoxide-$d_6$) δ: ppm 12.85 (s, 1H), 8.03 (d, 1H), 7.79 (d, 1H), 7.61 (d, 1H), 7.40 (m, 6H), 7.29 (s, 1H), 6.95 (d, 1H), 4.95 (s, 2H), 3.89 (t, 2H), 3.80 (s, 3H), 3.44 (t, 2H), 3.21 (s, 3H), 3.00 (t, 2H), 2.10 (s, 3H), 1.34 (m, 16H).

Example 47

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid

Example 47A 2-(tricyclo[3.3.1.1$^{3,7}$]dec-1-ylamino)-6-bromo-benzonitrile

2-Bromo-6-fluorobenzonitrile (300 mg) and 1-adamantane (295 mg) were added to dimethyl sulfoxide (5 mL). The solution was stirred until reactants had dissolved. The solution was then heated in a microwave reactor (Biotage) at 180° C. for 20 minutes. The solution was added to ethyl ether, and washed with 1 M aqueous HCl three times, and washed with brine. The combined organic layers were dried on anhydrous sodium sulfate, filtered, and concentrated. The crude material was purified by flash column chromatography on silica gel using 5% ethyl acetate (hexanes) to yield the product.

Example 47B

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid tert-butyl ester The title compound was prepared by substituting EXAMPLE 47A for EXAMPLE 20A in EXAMPLE 20B.

Example 47C

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid The title compound was prepared by substituting EXAMPLE 47B for EXAMPLE 2B in EXAMPLE 2C. $^1$H NMR (400 MHz, dimethylsulfoxide-$d_6$) δ ppm 8.03 (d, 1H), 7.79 (d, 1H), 7.64-7.58 (m, 2H), 7.49-7.29 (m, 6H), 7.06 (dd, 1H), 7.02 (d, 1H), 6.52 (d, 1H), 5.01 (bs, 2H), 3.91 (m, 2H), 3.03 (m, 2H), 2.10 (bs, 3H), 1.98 (bs, 6H), 1.68 (m, 6H).

Example 48

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid

Example 48A 2-(tricyclo[3.3.1.1$^{3,7}$]dec-1-ylsulfanyl)-6-bromo-benzonitrile 1-Adamantanethiol (278 mg) was dissolved in dimethyl sulfoxide (10 mL). Sodium hydride (60% in mineral oil, 42 mg) was added, and the solution was stirred at room temperature for 20 minutes. 2-Bromo-6-fluorobenzonitrile (300 mg) was added and the solution was heated to 130° C. for 1 hour. The solution was cooled, added to diethyl ether, washed with 1 M aqueous HCl three times, washed with brine, and dried over anhydrous sodium sulfate. After filtration, the solvent was removed under vacuum to yield the title compound.

Example 48B

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid tert-butyl ester The title compound was prepared by substituting EXAMPLE 48A for EXAMPLE 20A in EXAMPLE 20B.

Example 48C

6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid The title compound was prepared by substituting EXAMPLE 48B for EXAMPLE 2B in EXAMPLE 2C. $^1$H NMR (400 MHz, dimethylsulfoxide-$d_6$) δ ppm 12.86 (bs, 1H), 8.03 (d, 1H), 7.79 (d, 1H), 7.68-7.60 (m, 3H), 7.49-7.32 (m, 6H), 7.08 (d, 1H), 5.04 (bs, 2H), 3.98 (t, 2H), 3.05 (t, 2H), 2.00 (bs, 3H), 1.83 (bs, 4H), 1.79-1.72 (m, 2H), 1.60 (m, 6H).

Example 49

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 49A

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid tert-butyl ester The title compound was prepared by substituting imidazo[1,2-a]pyridine-2-amine for thiazolo[4,5-b]pyridine-2-amine in EXAMPLE 30D.

Example 49B

6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 49A for EXAMPLE 1F in EXAMPLE 1G. $^1$H NMR (400 MHz, dimethylsulfoxide-d$_6$) δ ppm 11.66 (br s, 1H), 8.76 (d, 1H), 8.36 (s, 1H), 7.72 (d, 1H), 7.60 (dd, 1H), 7.55 (dd, 1H), 7.51 (d, 1H), 7.42 (d, 1H), 7.37 (t, 1H), 7.27 (s, 1H), 7.24 (t, 1H), 6.93 (d, 1H), 4.96 (s, 2H), 3.88 (t, 2H), 3.71 (s, 2H), 3.01 (t, 2H), 2.10 (s, 3H), 1.93 (br s, 3H), 1.65 (br d, 3H), 1.54 (br m, 9H).

Example 50

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid

Example 50A

N-(3-bromo-2-methylphenyl)tricyclo[3.3.1.1$^{3,7}$]decane-1-carboxamide

3-Bromo-2-methylaniline (800 mg) and diisopropylethylamine (1667 mg) were added to dichloromethane (12 mL). 1-Adamantanecarbonyl chloride (940 mg) was added and the solution was stirred at room temperature for 16 hours. The solution was diluted with 50% ethyl acetate (hexanes), washed three times with 1 M aqueous HCl, washed with brine, dried over anhydrous sodium sulfate, and filtered. The solvent volume was partially reduced under vacuum, and the solid material precipitated out of solution, which was isolated by filtration to provide the title compound.

Example 50B

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid tert-butyl ester The title compound was prepared by substituting EXAMPLE 50A for EXAMPLE 20A in EXAMPLE 20B.

Example 50C

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid The title compound was prepared by substituting EXAMPLE 50B for EXAMPLE 2B in EXAMPLE 2C. $^1$H NMR (400 MHz, dimethylsulfoxide-d$_6$) δ ppm 12.86 (bs, 1H), 8.82 (s, 1H), 8.04 (d, 1H), 7.79 (d, 1H), 7.62 (d, 1H), 7.49-7.32 (m, 5H), 7.17-7.09 (m, 2H), 7.00 (d, 1H), 6.90 (dd, 1H), 4.99 (bs, 2H), 3.96 (t, 2H), 3.03 (t, 2H), 2.00 (bs, 3H), 1.90 (bs, 9H), 1.69 (bs, 6H).

Example 51

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl}pyridine-2-carboxylic acid

Example 51A 3-bromo-2-methyl-N-(tricyclo[3.3.1.1$^{3,7}$]dec-1-yl)benzenesulfonamide 3-Bromo-2-methylbenzene-1-sulfonyl chloride (300 mg) and 1-adamantanamine (185 mg) were dissolved in dichloromethane (4 mL). Diisopropylethylamine (432 mg) was added, and the solution was stirred at room temperature for 16 hours. The solution was diluted with 70% ethyl acetate (hexanes), washed three times with 1 M aqueous HCl, washed with brine, and dried over anhydrous sodium sulfate. After filtration, the solvent was removed to yield the product.

Example 51B

6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid tert-butyl ester The title compound was prepared by substituting EXAMPLE 51A for EXAMPLE 20A in EXAMPLE 20B.

Example 51C

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl}pyridine-2-carboxylic acid The title compound was prepared by substituting EXAMPLE 51B for EXAMPLE 2B in EXAMPLE 2C. $^1$H NMR (400 MHz, dimethylsulfoxide-d$_6$) δ ppm 12.86 (bs, 1H), 12.58 (bs, 1H), 8.03 (d, 1H), 7.89 (dd, 1H), 7.79 (d, 1H), 7.66-7.58 (m, 1H), 7.51-7.30 (m, 6H), 7.24 (dd, 1H), 7.03 (d, 1H), 5.01 (bs, 2H), 3.95 (t, 2H), 3.04 (t, 2H), 2.32 (bs, 3H), 1.91 (m, 3H), 1.70 (m, 6H), 1.58-1.44 (m, 6H).

Example 52

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid

Example 52A

N-(3-bromo-2-methylphenyl)-N-methyltricyclo[3.3.1.1$^{3,7}$]decane-1-carboxamide 3-Bromo-N,2-dimethylaniline (300 mg) and diisopropylethylamine (581 mg) were added to 1,2-dichloroethane (5 mL). 1-Adamantanecarbonyl chloride (328 mg) was added and the solution was heated at 50° C. for three days. The solution was diluted with 70% ethyl acetate (hexanes), washed three times with 1M aqueous HCl, washed with brine, dried over anhydrous sodium sulfate, filtered, and concentrated. The crude material was purified by flash column chromatography on silica gel using 10% ethyl acetate (hexanes) to yield the title compound.

Example 52B

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid tert-butyl ester The title compound was prepared by substituting EXAMPLE 52A for EXAMPLE 20A in EXAMPLE 20B.

Example 52C

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid The title compound was prepared by substituting EXAMPLE 52B for EXAMPLE 2B in EXAMPLE 2C. $^1$H NMR (400 MHz, dimethylsulfoxide-d$_6$) δ ppm 8.03 (d, 1H), 7.79 (d, 1H), 7.63 (d, 1H), 7.50-7.32 (m, 5H), 7.24-7.14 (m, 2H), 7.04 (dd, 1H), 7.01 (d, 1H), 5.00 (bs, 2H), 3.93 (t, 2H), 3.04 (t, 2H), 2.98 (s, 3H), 1.91 (s, 3H), 1.82-1.71 (m, 6H), 1.61-1.41 (m, 9H).

Example 53

6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1$^{3,7}$]dec-1-yl]methyl}-1H-pyrazol-4-yl)pyridine-2-carboxylic acid

Example 53A 1-(5-(tetrahydropyran-4-ylmethoxy)-3,7-dimethyltricyclo[3.3.1.1$^{3,7}$]dec-1-yl)-1H-pyrazole The title compound was prepared by substituting EXAMPLE 26A for EXAMPLE 7A and (tetrahydro-2H-pyran-4-yl)methanol for methanol in EXAMPLE 7B.

Example 53B 1-(5-(tetrahydropyran-4-ylmethoxy)-3,7-dimethyltricyclo[3.3.1.1$^{3,7}$]dec-1-yl)-5-methyl-1H-pyrazole The title compound was prepared by substituting EXAMPLE 53A for EXAMPLE 3A in EXAMPLE 3B.

Example 53C 4-bromo-1-(5-(tetrahydropyran-4-ylmethoxy)-3,7-dimethyltricyclo[3.3.1.1$^{3,7}$]dec-1-yl)-5-methyl-1H-pyrazole The title compound was prepared by substituting EXAMPLE 53B for EXAMPLE 3B in EXAMPLE 3C.

Example 53D tert-butyl 6-[8-(1,3-benzothiazol-2-ylcarbamoyl)-3,4-dihydroisoquinolin-2(1H)-yl]-3-(1-(5-(tetrahydropyran-4-ylmethoxy)-3,7-dimethyltricyclo[3.3.1.1$^{3,7}$]dec-1-yl)-5-methyl-1H-pyrazol-4-yl)picolinate The title compound was prepared by substituting EXAMPLE 53C for EXAMPLE 4A in EXAMPLE 4C.

Example 53E

6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1$^{3,7}$]dec-1-yl]methyl}-1H-pyrazol-4-yl)pyridine-2-carboxylic acid The title compound was prepared by substituting EXAMPLE 53D for EXAMPLE 2B in EXAMPLE 2C. $^1$H NMR (300 MHz, dimethylsulfoxide-d$_6$) δ ppm 12.84 (br. s, 1H), 8.03 (d, 1H), 7.79 (d, 1H), 7.61 (d, 1H), 7.47 (m, 3H), 7.35 (m, 2H), 7.27 (s, 1H), 6.95 (d, 1H), 4.95 (s, 2H), 3.89 (t, 2H), 3.80 (m, 4H), 3.22 (m, 6H), 3.01 (t, 2H), 2.11 (m, 5H), 1.51 (m, J=4.00 Hz, 15H).

Example 54

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid

Example 54A 3-bromo-2-methyl-benzoyl chloride

3-Bromo-2-methylbenzoic acid (2000 mg) was added to dichloromethane (50 mL) and N,N-dimethylformamide (1 mL). Oxalyl chloride (649 mg) was added and the solution was stirred for three minutes. The mixture was washed with 1 M aqueous HCl three times, washed with brine, and dried on anhydrous sodium sulfate. After filtration, the solvent was removed under vacuum to yield the product.

Example 54B 3-bromo-2-methyl-N-(tricyclo[3.3.1.1$^{3,7}$]dec-1-yl)benzamide

The title compound was prepared by substituting 1-adamananamine for 3-bromo-2-methylaniline and EXAMPLE 54A for 1-adamantanecarbonyl chloride in EXAMPLE 50A.

Example 54C tert-butyl 6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylate The title compound was prepared by substituting EXAMPLE 54B for EXAMPLE 20A in EXAMPLE 20B.

Example 54D

6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid The title compound was prepared by substituting EXAMPLE 54C for EXAMPLE 2B in EXAMPLE 2C. $^1$H NMR (400 MHz, dimethylsulfoxide-d$_6$) δ ppm 8.03 (d, 1H), 7.79 (d, 1H), 7.69 (s, 1H), 7.63 (d, 1H), 7.50-7.32 (m, 5H), 7.17-7.14 (m, 2H), 7.05 (t, 1H), 6.99 (d, 1H), 4.99 (bs, 2H), 3.93 (t, 2H), 3.03 (t, 2H), 2.04 (bs, 12H), 1.64 (bs, 6H).

Example 55

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid

Example 55A 3-bromo-N,2-dimethyl-N-(tricyclo[3.3.1.1$^{3,7}$]dec-1-ylmethyl)aniline EXAMPLE 52A (232 mg) was dissolved in tetrahydrofuran (3 mL) and borane (1 M in tetrahydrofuran, 2.6 mL) was added. The solution was stirred at room temperature for 16 hours and was quenched slowly with methanol. Aqueous HCl (4M, 6 mL) was added and the solution was stirred at room temperature for four hours. The pH was adjusted to 9 using sodium carbonate and the solution was extracted with diethyl ether. The extract was washed with brine and dried on anhydrous sodium sulfate. After filtration the solvent was removed under vacuum to yield the product.

Example 55B

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid tert-butyl ester The title compound was prepared by substituting EXAMPLE 55A for EXAMPLE 20A in EXAMPLE 20B.

Example 55C

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid The title compound was prepared by substituting EXAMPLE 55B for EXAMPLE 2B in EXAMPLE 2C. $^1$H NMR (400 MHz, dimethylsulfoxide-d$_6$) δ ppm 12.89 (bs, 1H), 8.03 (d, 1H), 7.79 (d, 1H), 7.63 (d, 1H), 7.50-7.32 (m, 5H), 7.20-7.05 (m, 2H), 6.98 (d, 1H), 6.70 (d, 1H), 4.98 (bs, 2H), 3.92 (t, 2H), 3.03 (t, 2H), 2.77 (bs, 2H), 2.61 (bs, 3H), 2.07 (bs, 3H), 1.87 (bs, 3H), 1.66-1.50 (m, 6H), 1.43 (bs, 6H).

Example 56

6-[8-(1,3-benzothiazol-2-ylcarbamoyl)-3,4-dihydroisoquinolin-2(1H)-yl]-3-(1-{[2-(2-methoxyethyl)tricyclo[3.3.1.1$^{3,7}$]dec-2-yl]methyl}-1H-pyrazol-4-yl)pyridine-2-carboxylic acid

Example 56A methyl tricyclo[3.3.1.1$^{3,7}$]decane-2-carboxylate

To a solution of adamantane-2-carboxylic acid 1 (0.486 g, 2.70 mmol) in ethyl acetate (10 mL)/methanol (5 mL) was dropwise added (trimethylsilyl)diazomethane (1.348 ml, 2.70 mmol) and the mixture was stirred at room temperature for 14 hours. The reaction mixture was concentrated and purified by flash chromotography (silica 40 g, 0%-30% ethyl acetate/hexanes).

Example 56B methyl 2-(2-methoxyethyl)tricyclo[3.3.1.1$^{3,7}$]decane-2-carboxylate To a solution of EXAMPLE 56A (0.314 g) in tetrahydrofuran (5 mL) was added dropwise lithium diisopropylamide (1.401 mL) at −78° C. The reaction mixture was stirred for 60 minutes and 2-bromoethyl methyl ether (0.562 g) was added. The reaction mixture was slowly warmed up to room temperature, stirred at room temperature overnight, quenched with saturated aqueous NH$_4$Cl solution (2 mL), and extracted with ether. The combined organic layer was dried over Na$_2$SO$_4$, filtered, concentrated and purified by flash chromotography (silica 40 g, 0%-30% ethyl acetate/hexanes).

Example 56C

[2-(2-methoxyethyl)tricyclo[3.3.1.1$^{3,7}$]dec-2-yl]methanol

To a solution of EXAMPLE 56B (135 mg) in tetrahydrofuran (5 mL) was added dropwise lithium aluminum hydride (0.535 mL) at room temperature. The reaction mixture was stirred for 14 hours and sodium hydroxide (0.324 mL) was carefully added. The reaction mixture was stirred at room temperature for 60 minutes, filtered and concentrated.

Example 56D

1-{[2-(2-methoxyethyl)tricyclo[3.3.1.1$^{3,7}$]dec-2-yl]methyl}-1H-pyrazole

The title compound was prepared by substituting EXAMPLE 56C for 1-adamantanemethanol and pyrazole for 3,5-dimethyl-4-(4,4,5,5-tetramethyl-1,3,2-dioxaborolan-2-yl)-1H-pyrazole in EXAMPLE 2A.

Example 56E 4-bromo-1-{[2-(2-methoxyethyl)tricyclo[3.3.1.1$^{3,7}$]dec-2-yl]methyl}-1H-pyrazole The title compound was prepared by substituting EXAMPLE 56D for EXAMPLE 3B in EXAMPLE 3C.

Example 56F tert-butyl 6-(8-(benzo[d]thiazol-2-ylcarbamoyl)-3,4-dihydroisoquinolin-2(1H)-yl)-3-(1-{[2-(2-methoxyethyl)tricyclo[3.3.1.1$^{3,7}$]dec-2-yl]methyl}-1H-pyrazol-4-yl)picolinate The title compound was prepared by substituting EXAMPLE 56E for EXAMPLE 4A in EXAMPLE 4C.

Example 56G

6-[8-(1,3-benzothiazol-2-ylcarbamoyl)-3,4-dihydroisoquinolin-2(1H)-yl]-3-(1-{[2-(2-methoxyethyl)tricyclo[3.3.1.1$^{3,7}$]dec-2-yl]methyl}-1H-pyrazol-4-yl)pyridine-2-carboxylic acid The title compound was prepared by substituting EXAMPLE 56F for EXAMPLE 2B in EXAMPLE 2C. $^1$H NMR (400 MHz, dimethylsulfoxide-d$_6$) δ ppm 8.04 (d, 1H), 7.80 (d, 1H), 7.69 (d, 2H), 7.61 (d, 1H), 7.54 (s, 1H), 7.51-7.45 (m, 1H), 7.43 (d, 1H), 7.35 (dd, 2H), 6.94 (d, 1H), 4.94 (s, 2H), 4.33 (s, 2H), 3.86 (t, 2H), 3.47 (d, 2H), 3.29-3.22 (m, 2H), 3.19 (s, 3H), 3.00 (t, 2H), 2.33-2.24 (m, 2H), 2.01 (d, 2H), 1.90 (s, 1H), 1.82 (s, 1H), 1.67 (s, 2H), 1.56 (dd, 8H).

Example 57

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-1,2,3-triazol-4-yl]pyridine-2-carboxylic acid

Example 57A 1-(azidomethyl)tricyclo[3.3.1.1$^{3,7}$]decane

1-Adamantanemethanol (500 mg) was dissolved in dichloromethane (15 mL). The solution was chilled in an ice bath and triethylamine (0.587 mL) was added, followed by methanesulfonyl chloride (0.258 mL). The reaction mixture was stirred for 4 hours at 0° C., then transferred to a separatory funnel and rinsed with 1N aqueous HCl (15 mL), saturated aqueous NaHCO$_3$ (15 mL) and brine (15 mL). The organic extracts were dried (Na$_2$SO$_4$), filtered, and concentrated. A portion of the resulting crude mesylate (293 mg) and sodium azide (390 mg) were combined in N,N-dimethylformamide (1.2 mL) and the reaction mixture was heated to 120° C. overnight, then cooled to room temperature and partitioned between ethyl acetate (3×15 mL) and water (20 mL). The organic extracts were dried (Na$_2$SO$_4$), filtered, and concentrated to provide the title compound, which was used in the next step without further purification.

Example 57B 1-(tricyclo[3.3.1.1$^{3,7}$]dec-1-ylmethyl)-5-methyl-4-(tributylstannyl)-1H-1,2,3-triazole EXAMPLE 57A (224 mg), tributyl-n-propynyltin (390 mg) and toluene (2 mL) were combined in a sealed reaction vessel and heated to 130° C. overnight. The reaction mixture was placed atop a column and purified by flash chromatography on silica gel eluting with 0-15% ethyl acetate in hexanes to provide the title compound.

Example 57C methyl 6-amino-3-bromopicolinate

To a solution of 6-amino-3-bromopicolinic acid (30 g) in ethyl acetate (300 mL) and methanol (300 mL) was added TMS-diazomethane (70 mL, 2M in hexanes) and the reaction mixture was stirred for 3 days. The mixture was concentrated, taken up in ether (500 mL) and washed with aqueous Na$_2$CO$_3$ solution (twice), then washed with brine, dried over sodium sulfate, filtered and concentrated to provide the title compound.

Example 57D methyl 3-bromo-6-fluoropicolinate

To a solution of nitrosonium terafluoroborate (17.8 g) in dichloromethane (100 mL) at 5° C. was added EXAMPLE 57C (26.1 g) in dichloromethane (250 mL) over 1 hour. The reaction mixture was stirred an additional 30 minutes at 5° C., and allowed to warm to room temperature overnight. The reaction mixture was quenched with pH 7 buffer (100 mL), and neutralized with solid potassium carbonate. The resulting mixture was extracted with ether (twice), and the combined organic extracts were washed with brine, dried over sodium sulfate, filtered and concentrated. The residue was chromatographed on silica gel using 1-10% ethyl acetate in hexanes to provide the title compound.

Example 57E methyl 3-(tricyclo[3.3.1.1$^{3,7}$]dec-1-ylmethyl)-5-methyl-1H-1,2,3-triazol-4-yl)-6-fluoropicolinate EXAMPLE 57B (333 mg), EXAMPLE 57D (178 mg) and PdCl$_2$(PPh$_3$)$_2$ (22 mg) were combined in a sealed tube with N,N-dimethylformamide (1.3 mL) and the mixture was sparged with nitrogen and then heated to 100° C. overnight. Saturated aqueous KF (2 mL) and ethyl acetate (2 mL) were added and the mixture was stirred for 1 hour, and filtered through diatomaceous earth, rinsing the filter cake with ethyl acetate (20 mL). The filtrate was placed into a separatory funnel and the layers were separated. The aqueous layer was extracted with ethyl acetate (2×25 mL). The combined organic extracts were dried (Na$_2$SO$_4$), filtered, concentrated, and purified by flash chromatography on silica gel using 0 to 50% ethyl acetate in hexanes to provide the title compound.

Example 57F methyl 6-(8-(benzo[d]thiazol-2-ylcarbamoyl)-3,4-dihydroisoquinolin-2(1H)-yl)-3-(1-(tricyclo[3.3.1.1$^{3,7}$]dec-1-ylmethyl)-5-methyl-1H-1,2,3-triazol-4-yl)picolinate EXAMPLE 1C (110 mg), EXAMPLE 57E (93 mg) and cesium carbonate (394 mg) were combined in DMSO (1.2 mL) and the mixture was heated to 65° C. overnight. The reaction mixture was then partitioned between ethyl acetate (3×10 mL) and water (10 mL). The organic extracts were dried (Na$_2$SO$_4$), filtered, and concentrated, then purified by flash chromatography using 0 to 70% ethyl acetate in hexanes to provide the title compound.

Example 57G

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-1-ylmethyl)-1H-1,2,3-triazol-4-yl]pyridine-2-carboxylic acid Example 57F (83 mg) was dissolved in dioxane (1 mL) and LiOH (1M in water, 0.616 mL) was added. The mixture was heated to 60° C. for 3 hours, then cooled to room temperature and diluted with 1N NaH$_2$PO$_4$ (25 mL) and extracted with ethyl acetate (three times). The organic extracts were dried (Na$_2$SO$_4$), filtered, and concentrated. The residue was purified by flash chromatography on silica gel eluting with 0 to 10% methanol in dichloromethane to provide the title compound. $^1$H NMR (300 MHz, dimethylsulfoxide-d$_6$) δ ppm 12.68-12.90 (br m, 2H), 8.04 (d, 1H), 7.79 (d, 1H), 7.67 (d, 1H), 7.62 (d, 1H), 7.42-7.51 (m, 2H), 7.31-7.41 (m, 2H), 7.00 (d, 1H), 5.00 (s, 2H), 3.89-3.97 (m, 4H), 3.02 (t, 2H), 2.16 (s, 3H), 1.94 (s, 3H), 1.53-1.69 (m, 6H), 1.52 (s, 6H).

Example 58

6-[8-(1,3-benzothiazol-2-ylcarbamoyl)-3,4-dihydroisoquinolin-2(1H)-yl]-3-(5-cyano-1-{[3-methoxytricyclo[3.3.1.1$^{3,7}$]dec-1-yl]methyl}-2-methyl-1H-pyrrol-3-yl)pyridine-2-carboxylic acid

Example 58A 3-iodo-5-cyano-1-{[3-methoxytricyclo[3.3.1.1$^{3,7}$]dec-1-yl]methyl}-2-methyl-1H-pyrrole The title compound was prepared by substituting 3-methoxyadamantane-1-methanol for adamantane-1-ethanol and EXAMPLE 23D for 3,5-dimethyl-4-(4,4,5,5-tetramethyl-1,3,2-dioxaborolan-2-yl)-1H-pyrazole in EXAMPLE 2A.

Example 58B

6-[8-(Benzothiazol-2-ylcarbamoyl)-3,4-dihydro-1H-isoquinolin-2-yl]-3-[5-cyano-1-(3-methoxy-adamantan-1-ylmethyl)-2-methyl-1H-pyrrol-3-yl]-pyridine-2-carboxylic acid tert-butyl ester The title compound was prepared by substituting EXAMPLE 58A for EXAMPLE 20A in EXAMPLE 20B.

Example 58C

6-[8-(1,3-benzothiazol-2-ylcarbamoyl)-3,4-dihydroisoquinolin-2(1H)-yl]-3-(5-cyano-1-{[3-methoxytricyclo[3.3.1.1$^{3,7}$]dec-1-yl]methyl}-2-methyl-1H-pyrrol-3-yl)pyridine-2-carboxylic acid The title compound was prepared by substituting EXAMPLE 58B for EXAMPLE 2B in EXAMPLE 2C. $^1$H NMR (400 MHz, dimethylsulfoxide-d$_6$) δ ppm 12.86 (s, 1H), 8.04 (d, 1H), 7.79 (d, 1H), 7.62 (d, 1H), 7.51 (d, 1H), 7.42-7.50 (m, 2H), 7.33-7.39 (m, 2H), 6.95 (d, 1H), 6.83 (s, 1H), 4.96 (s, 2H), 3.89 (t, 2H), 3.82 (s, 2H), 3.10 (s, 3H), 3.01 (t, 2H), 2.18 (s, 2H), 2.09 (s, 3H), 1.40-1.65 (m, 12H).

Example 59

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-pyrazol-4-yl]pyridine-2-carboxylic acid

Example 59A 1-(2-oxatricyclo[3.3.1.1$^{3,7}$]dec-1-ylmethyl)-4-chloro-1H-pyrazole The title compound was prepared by substituting EXAMPLE 13A for 1-adamantanemethanol and 4-chloro-1H-pyrazole for 3,5-dimethyl-4-(4,4,5,5-tetramethyl-1,3,2-dioxaborolan-2-yl)-1H-pyrazole in EXAMPLE 2A.

Example 59B 1-(2-oxatricyclo[3.3.1.1$^{3,7}$]dec-1-ylmethyl)-4-chloro-5-methyl-1H-pyrazole A solution of EXAMPLE 59A (0.25 g) in tetrahydrofuran (3 mL) was cooled to −78° C. butyllithium was (0.48 mL) added dropwise. Additional tetrahydrofuran (2 mL) was added and the reaction mixture was stirred for 1 hour at −78° C. To the reaction mixture was added iodomethane (0.08 mL) in one portion and the reaction was allowed to warm to 0° C. After 30 minutes, the reaction was diluted with ether (50 mL), washed with water (30 mL) and brine (30 mL), dried over magnesium sulfate, filtered, and concentrated. Silica gel chromatography eluting with a gradient of 3% to 20% ethyl acetate/hexanes provided the title compound.

Example 59C 1-(2-oxatricyclo[3.3.1.1$^{3,7}$]dec-1-ylmethyl)-4-(4,4,5,5-tetramethyl-1,3,2-dioxaborolan-5-methyl-2-yl)-1H-pyrazole A solution of EXAMPLE 59B (0.13 g), 4,4,5,5-tetramethyl-1,3,2-dioxaborolane (0.13 mL), triethylamine (0.20 mL), dicyclohexyl(2',6'-dimethoxybiphenyl-2-yl)phosphine (0.04 g) and bis(benzonitrile)palladium(II) chloride (6 mg) was heated in dioxane (2.5 mL) at 105° C. After 2 hours, the reaction mixture was diluted with ethyl acetate and washed with water and dried over magnesium sulfate. After filtration and concentration, silica gel chromatography eluting with a gradient of 1.5% to 15% ethyl acetate/hexanes provided the title compound.

Example 59D

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-pyrazol-4-yl]pyridine-2-carboxylic acid A solution of a 1:1 ratio of dioxane and water was degassed with nitrogen for 45 minutes. This solution (5 mL) was added to EXAMPLE 1E (0.31 g), EXAMPLE 59C (0.22 g), potassium phosphate (0.41 g), tris(dibenzylideneacetone)dipalladium(0) chloroform adduct (0.014 g) and 1,3,5,7-tetramethyl-6-tetradecane-2,4,8-trioxa-6-phosphaadamantane (0.023 g). The mixture was degassed and heated to 90° C. under nitrogen overnight. The reaction mixture was cooled, diluted with ethyl acetate (100 mL) and washed with water (three×50 mL) and brine (50 mL), dried over magnesium sulfate, filtered and concentrated. Silica gel chromatography eluting with a gradient of 5% to 100% ethyl acetate/hexanes gave the desired ester. The ester was dissolved in dichloromethane (0.5 mL), and TFA (0.5 mL) was added and the mixture was stirred overnight. The reaction mixture was concentrated, loaded onto silica gel and eluted with a gradient of 1% to 4% methanol/dichloromethane to provide the title compound. $^1$H NMR (300 MHz, dimethylsulfoxide-$d_6$) δ: ppm 12.84 (s, 1H), 8.07-7.99 (m, 1H), 7.79 (d, 1H), 7.61 (d, 1H), 7.53-7.40 (m, 3H), 7.40-7.31 (m, 2H), 7.26 (s, 1H), 6.95 (d, 1H), 4.95 (s, 2H), 3.96 (s, 1H), 3.93-3.82 (m, 4H), 3.01 (t, 2H), 2.14 (s, 3H), 2.08 (s, 2H), 1.86-1.65 (m, 4H), 1.56 (m, 6H).

Example 60

6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid Example 60A 2-bromo-6-(tricyclo[3.3.1.1$^{3,7}$]dec-1-ylthio)benzonitrile To a solution of adamantanethiol (1.01 g) in N,N-dimethylacetamide (20 mL) at room temperature was added NaH (0.24 g, 60% in mineral oil) and the reaction was stirred for 10 minutes. 2-Fluoro-6-bromobenzonitrile (1 g) was added and the mixture was heated to 80° C. for 1 hour. The reaction mixture was cooled and diluted with ether (400 mL), and the mixture was washed three times with 1M NaOH solution and once with brine, then dried over sodium sulfate, filtered and concentrated to yield the crude product which was taken on to the next step without purification.

Example 60B 2-bromo-6-(tricyclo[3.3.1.1$^{3,7}$]dec-1-ylsulfonyl)benzonitrile

A mixture of EXAMPLE 60A (1.73 g) and m-chloroperoxybenzoic acid (2.46 g) in 1,2-dichloroethane (50 mL) was stirred overnight. The reaction was diluted with ether (300 mL), washed twice with $Na_2CO_3$ solution, and brine, then dried over sodium sulfate, filtered and concentrated. The residue was chromatographed on silica gel using 2-50% ethyl acetate in hexanes to give the desired product.

Example 60C tert-butyl 6-(8-(benzo[d]thiazol-2-ylcarbamoyl)-3,4-dihydroisoquinolin-2(1H)-yl)-3-(2-cyano-3-(tricyclo[3.3.1.1$^{3,7}$]dec-1-ylsulfonyl)phenyl)picolinate The title compound was prepared by substituting EXAMPLE 60B for EXAMPLE 19A and EXAMPLE 4B for EXAMPLE 3D in EXAMPLE 19B.

Example 60D

6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid The title compound was prepared by substituting EXAMPLE 60C for EXAMPLE 2B in EXAMPLE 2C. $^1$H NMR (300 MHz, dimethylsulfoxide-$d_6$) δ ppm 12.65 (br s, 1H), 8.03 (d, 1H), 7.94 (d, 2H), 7.77 (m, 2H), 7.70 (d, 1H), 7.62 (m, 1H), 7.44 (m, 2H), 7.30 (m, 2H), 7.12 (d, 1H), 5.06 (s, 2H), 4.02 (t, 2H), 3.05 (m, 2H), 2.10 (m, 3H), 1.88 (s, 6H), 1.61 (m, 6H).

Example 61

6-[8-(1,3-benzothiazol-2-ylcarbamoyl)-3,4-dihydroisoquinolin-2(1H)-yl]-2'-[cyclooctyl(methyl)amino]-3'-methyl-3,4'-bipyridine-2-carboxylic acid Example 61A N-cyclooctyl-4-iodo-3-methylpyridin-2-amine 2-Fluoro-4-iodo-3-methylpyridine (700 mg) in cyclooctanamine (3.8 g) was heated at 130° C. overnight, cooled and diluted with dichloromethane. The resulting mixture was loaded onto a silica gel cartridge, eluting with 0-100% dichloromethane in hexanes to provide the title compound.

Example 61B

N-cyclooctyl-4-iodo-N,3-dimethylpyridin-2-amine

EXAMPLE 61A (150 mg), $Cs_2CO_3$ (142 mg) and $CH_3I$ (0.027 mL) in N,N-dimethylacetamide (2 mL) was stirred at 38° C. overnight. More $CH_3I$ (0.5 mL) and sodium hydride (52.3 mg, 60% in mineral oil) were added. The resulting mixture was stirred at 39° C. for 2 days, quenched with water and diluted with ethyl acetate. The organic layer was washed with brine and concentrated. The residue was purified by Prep HPLC using Gilson system eluting with 20-80% acetonitrile in 0.1% TFA/water to provide the title compound.

Example 61C tert-butyl 6-(8-(benzo[d]thiazol-2-ylcarbamoyl)-3,4-dihydroisoquinolin-2(1H)-yl)-2'-(cyclooctyl(methyl)amino)-3'-methyl-3,4'-bipyridine-2-carboxylate The title compound was prepared by substituting EXAMPLE 61B for EXAMPLE 20A in EXAMPLE 20B.

Example 61D 6-(8-(benzo[d]thiazol-2-ylcarbamoyl)-3,4-dihydroisoquinolin-2(1H)-yl)-2'-(cyclooctyl(methyl)amino)-3'-methyl-3,4'-bipyridine-2-carboxylic acid The title compound was prepared by substituting EXAMPLE 61C for EXAMPLE 2B in EXAMPLE 2C. $^1$H NMR (400 MHz, dimethylsulfoxide-$d_6$) δ ppm 12.88 (s, 2H), 8.01-8.07 (m, 2H), 7.79 (d, 1H), 7.63 (d, 1H), 7.59 (d, 1H), 7.43-7.50 (m, 2H), 7.32-7.41 (m, 2H), 7.07 (d, 1H), 6.88 (s, 1H), 5.03 (s, 2H), 3.96 (t, 2H), 3.04 (t, 2H), 2.82 (s, 3H), 2.02 (s, 3H), 1.36-1.87 (m, 15H).

Example 62

6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-2-ylmethyl)-1H-pyrazol-4-yl]pyridine-2-carboxylic acid Example 62A 1-(tricyclo[3.3.1.1$^{3,7}$]dec-2-ylmethyl)-1H-pyrazole The title compound was prepared by substituting EXAMPLE 10A for 1-adamantanemethanol and pyrazole for 3,5-dimethyl-4-(4,4,5,5-tetramethyl-1,3,2-dioxaborolan-2-yl)-1H-pyrazole in EXAMPLE 2A.

Example 62B 5-methyl-1-(tricyclo[3.3.1.1³,⁷]dec-2-ylmethyl)-1H-pyrazole

To a solution of EXAMPLE 62A (0.192 g, 0.888 mmol) in tetrahydrofuran (1 mL)/toluene (1 mL) was added n-butyllithium (1.6 M, 0.721 mL) at 0° C. The reaction mixture was stirred for 60 minutes. Then $CH_3I$ (0.166 mL) was added and stirring continued for 3 hours at 0° C. The reaction mixture was quenched with water, extracted with diethyl ether, dried over $Na_2SO_4$, filtered, and concentrated.

Example 62C 4-bromo-5-methyl-1-(tricyclo[3.3.1.1³,⁷]dec-2-ylmethyl)-1H-pyrazole

The title compound was prepared by substituting EXAMPLE 62B for EXAMPLE 3B in EXAMPLE 3C.

Example 62D tert-butyl 6-[8-(1,3-benzothiazol-2-ylcarbamoyl)-3,4-dihydroisoquinolin-2(1H)-yl]-3-[5-methyl-1-(tricyclo[3.3.1.1³,⁷]dec-2-ylmethyl)-1H-pyrazol-4-yl]pyridine-2-carboxylate The title compound was prepared by substituting EXAMPLE 62C for EXAMPLE 4A in EXAMPLE 4C.

Example 62E

6-[8-(1,3-benzothiazol-2-ylcarbamoyl)-3,4-dihydroisoquinolin-2(1H)-yl]-3-[5-methyl-1-(tricyclo[3.3.1.1³,⁷]dec-2-ylmethyl)-1H-pyrazol-4-yl]pyridine-2-carboxylic acid The title compound was prepared by substituting EXAMPLE 62D for EXAMPLE 2B in EXAMPLE 2C. $^1$H NMR (400 MHz, dimethylsulfoxide-$d_6$) δ ppm 12.85 (s, 1H), 8.04 (d, 1H), 7.79 (d, 1H), 7.61 (d, 1H), 7.53-7.40 (m, 3H), 7.40-7.31 (m, 2H), 7.26 (s, 1H), 6.94 (d, 1H), 4.95 (s, 2H), 4.13 (d, 2H), 3.91-3.85 (m, 2H), 3.02 (t, 2H), 2.18 (t, 1H), 2.13 (s, 3H), 2.00 (d, 2H), 1.90-1.73 (m, 4H), 1.74-1.59 (m, 6H), 1.53 (d, 2H).

Example 63

6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1³,⁷]dec-1-yl}methyl)-5-methyl-1H-pyrazol-4-yl]pyridine-2-carboxylic acid Example 63A 1-({3-[2-(2-methoxyethoxy)ethoxy]tricyclo[3.3.1.1³,⁷]dec-1-yl}methyl)-1H-pyrazole The title compound was prepared by substituting EXAMPLE 26A for EXAMPLE 7A and 2-(2-methoxyethoxy)ethanol for methanol in EXAMPLE 7B.

Example 63B 1-({3-[2-(2-methoxyethoxy)ethoxy]tricyclo[3.3.1.1³,⁷]dec-1-yl}methyl)-5-methyl-1H-pyrazole The title compound was prepared by substituting EXAMPLE 63A for EXAMPLE 3A in EXAMPLE 3B.

Example 63C 4-bromo-1-({3-[2-(2-methoxyethoxy)ethoxy]tricyclo[3.3.1.1³,⁷]dec-1-yl}methyl)-5-methyl-1H-pyrazole The title compound was prepared by substituting EXAMPLE 63B for EXAMPLE 3B in EXAMPLE 3C, with the modification that the title compound was purified by RP-HPLC on a Gilson system, eluting with a gradient of 20% to 100% acetonitrile in water containing 0.1% v/v trifluoroacetic acid.

Example 63D tert-butyl 6-(8-(benzo[d]thiazol-2-ylcarbamoyl)-3,4-dihydroisoquinolin-2(1H)-yl)-3-[1-({3-[2-(2-methoxyethoxy)ethoxy]tricyclo[3.3.1.1³,⁷]dec-1-yl}methyl)-5-methyl-1H-pyrazol-4-yl]picolinate The title compound was prepared by substituting EXAMPLE 63C for EXAMPLE 4A in EXAMPLE 4C.

Example 63E

6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1³,⁷]dec-1-yl}methyl)-5-methyl-1H-pyrazol-4-yl]pyridine-2-carboxylic acid The title compound was prepared by substituting EXAMPLE 63D for EXAMPLE 2B in EXAMPLE 2C. $^1$H NMR (300 MHz, dimethylsulfoxide-$d_6$) δ ppm 12.84 (bs, 1H), 8.03 (d, 1H), 7.79 (d, 1H), 7.61 (d, 1H), 7.48 (m, 3H), 7.36 (m, 2H), 7.27 (s, 1H), 6.94 (d, 1H), 4.95 (s, 2H), 3.89 (t, 2H), 3.78 (s, 2H), 3.48 (m, 2H), 3.44 (s, 3H), 3.22 (s, 3H), 3.02 (t, 2H), 2.10 (m, 5H), 1.54 (m, 12H).

Example 64

6-[8-(1,3-benzothiazol-2-ylcarbamoyl)-3,4-dihydroisoquinolin-2(1H)-yl]-3-(2-methyl-3-{methyl[(tricyclo[3.3.1.1³,⁷]dec-2-yl]carbamoyl}phenyl)pyridine-2-carboxylic acid Example 64A 3-bromo-N,2-dimethyl-N-(tricyclo[3.3.1.1³,⁷]dec-2-yl)benzamide The title compound was prepared by substituting N-adamantan-2-yl-N-methyl-amine for 1-adamantanamine and 3-bromo-2-methylbenzolyl chloride for 1-adamantanecarbonyl chloride in EXAMPLE 50A.

Example 64B

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]carbamoyl}phenyl)pyridine-2-carboxylic acid tert-butyl ester The title compound was prepared by substituting EXAMPLE 64A for EXAMPLE 20A in EXAMPLE 20B.

Example 64C

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]carbamoyl}phenyl)pyridine-2-carboxylic acid The title compound was prepared by substituting EXAMPLE 64B for EXAMPLE 2B in EXAMPLE 2C. $^1$H NMR (400 MHz, dimethylsulfoxide-d$_6$) δ ppm 8.03 (d, 1H), 7.79 (d, 1H), 7.62 (d, 1H), 7.50-7.32 (m, 6H), 7.20 (t, 1H), 7.08-6.95 (m, 2H), 4.99 (bs, 2H), 3.92 (t, 2H), 3.03 (t, 2H), 2.94 (bs, 3H), 2.22 (bs, 3H), 2.05-1.60 (m, 15H).

Example 65

6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid

Example 65A 1-((5-methyl-1H-pyrazol-1-yl)methyl)cyclooctanol

To a cold (−78° C.) solution of n-butyllithium (10 mL, 2.5M) in tetrahydrofuran (20 mL) was added 1,5-dimethyl-1H-pyrazole (2.0 g) in tetrahydrofuran (10 mL) dropwise via syringe. After 1 hour, cyclooctanone (2.63 g) in tetrahydrofuran (5 mL) was added dropwise and the reaction mixture was allowed to warm to room temperature. The mixture was quenched by the addition of saturated ammonium chloride solution and ethyl acetate. The layers were separated and the aqueous layer was extracted twice with additional ethyl acetate. The combined organics were dried over Na$_2$SO$_4$, filtered, and concentrated to provide the title compound.

Example 65B 5-methyl-1-((1-(2-(methylsulfonyl)ethoxy)cyclooctyl)methyl)-1H-pyrazole Sodium hydride (60% dispersion in mineral oil, 200 mg) was added to a stirred solution of EXAMPLE 65A (667 mg) in tetrahydrofuran (10 mL) and the mixture was stirred at room temperature for 30 minutes before the addition of methyl vinyl sulfone (1.27 g). The mixture was stirred at room temperature for 3 hours. Aqueous NH$_4$Cl was added to quench the reaction and the mixture was extracted with ethyl acetate (three times) and the combined organic layers were washed with water and brine, dried over Na$_2$SO$_4$, and filtered. The filtrate was concentrated to provide the crude product.

Example 65C 4-iodo-5-methyl-1-((1-(2-(methylsulfonyl)ethoxy)cyclooctyl)methyl)-1H-pyrazole The title compound was prepared by substituting EXAMPLE 65B for EXAMPLE 16D in EXAMPLE 16E.

Example 65D

6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid The title compound was prepared by substituting EXAMPLE 65C for EXAMPLE 4A in EXAMPLE 4B, then substituting that product for EXAMPLE 2B in EXAMPLE 2C. $^1$H NMR (300 MHz, dimethylsulfoxide-d$_6$) δ ppm 12.86 (s, 1H), 8.04 (d, 1H), 7.79 (d, 1H), 7.61 (d, 1H), 7.42 (m, 6H), 7.31 (s, 1H), 6.95 (d, 1H), 4.95 (s, 2H), 4.07 (s, 3H), 3.89 (t, 2H), 3.74 (t, 2H), 3.26 (t, 2H), 3.02 (t, 2H), 2.90 (s, 3H), 2.15 (m, 3H), 1.58 (m, 14H).

Example 66

6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-1,2,3-triazol-4-yl]pyridine-2-carboxylic acid

Example 66A 1-(azidomethyl)-2-oxatricyclo[3.3.1.1$^{3,7}$]decane

The title compound was prepared by substituting 1-(2-oxatricyclo[3.3.1.1$^{3,7}$]decyl)-methanol for 1-adamantanemethanol in EXAMPLE 57A.

Example 66B 1-(2-oxatricyclo[3.3.1.1$^{3,7}$]dec-1-ylmethyl)-5-methyl-4-(tributylstannyl)-1H-1,2,3-triazole The title compound was prepared by substituting EXAMPLE 66A for EXAMPLE 57A in EXAMPLE 57B.

Example 66C tert-butyl-3-bromo-6-fluoropicolinate

The title compound was prepared by substituting 3-bromo-6-fluoropicolinic acid for 3-bromo-6-chloropicolinic acid in EXAMPLE 1D.

Example 66D tert-butyl 3-(1-(2-oxatricyclo[3.3.1.1$^{3,7}$]dec-1-ylmethyl)-5-methyl-1H-1,2,3-triazol-4-yl)-6-fluoropicolinate The title compound was prepared by substituting EXAMPLE 66B for EXAMPLE 57B and EXAMPLE 66C for EXAMPLE 57D in EXAMPLE 57E.

Example 66E tert-butyl 6-(8-(benzo[d]thiazol-2-ylcarbamoyl)-3,4-dihydroisoquinolin-2(1H)-yl)-3-(1-(2-oxatricyclo[3.3.1.1$^{3,7}$]dec-1-ylmethyl)-5-methyl-1H-1,2,3-triazol-4-yl)picolinate The title compound was prepared by substituting EXAMPLE 66D for EXAMPLE 57E in EXAMPLE 57F.

Example 66F 6-(8-(benzo[d]thiazol-2-ylcarbamoyl)-3,4-dihydroisoquinolin-2(1H)-yl)-3-(1-(2-oxatricyclo[3.3.1.1$^{3,7}$]dec-1-ylmethyl)-5-methyl-1H-1,2,3-triazol-4-yl)picolinate The title compound was prepared by substituting EXAMPLE 66E for EXAMPLE 2B in EXAMPLE 2C. $^1$H NMR (300 MHz, dimethylsulfoxide-d$_6$) δ ppm 12.85 (s, 1H), 12.72 (s, 1H), 8.04 (d, 1H), 7.79 (d, 1H), 7.59-7.67 (m, 2H), 7.41-7.51 (m, 2H), 7.32-7.40 (m, 2H), 7.00 (d, 1H), 4.99 (s, 2H), 4.16 (s, 2H), 3.96 (s, 1H), 3.93 (t, 2H), 3.03 (t, 2H), 2.19 (s, 3H), 2.10 (s, 2H), 1.68-1.84 (m, 4H), 1.51-1.66 (m, 6H).

Example 67

3-[5-methyl-1-(2-oxatricyclo[3.3.1.1$^{3,7}$]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid

Example 67A 2-(5-bromo-6-(tert-butoxycarbonyl)pyridin-2-yl)-1,2,3,4-tetrahydroisoquinoline-8-carboxylic acid A solution of methyl 1,2,3,4-tetrahydroisoquinoline-8-carboxylate, hydrochloric acid (13.6 g), tert-butyl 3-bromo-6-chloropicolinate (17.4 g) and cesium carbonate (39 g) were stirred together in N,N-dimethylacetamide (110 mL) and heated at 120° C. under nitrogen overnight. The reaction mixture was cooled, diluted with water and extracted with ethyl acetate. The organic layer was washed with brine and the combined aqueous layers were back-extracted with ethyl acetate. The combined organic layers were dried over sodium sulfate, filtered and concentrated. Silica gel chromatography using 20-100% ethyl acetate in hexanes provided the title compound.

Example 67B tert-butyl 3-bromo-6-(8-(thiazolo[5,4-b]pyridin-2-ylcarbamoyl)-3,4-dihydroisoquinolin-2(1H)-yl)picolinate The title compound was prepared by substituting thiazolo[5,4-b]pyridin-2-amine for benzo[d]thiazol-2-amine and EXAMPLE 67A for 2-(tert-butoxycarbonyl)-1,2,3,4-tetrahydroisoquinoline-8-carboxylic acid in EXAMPLE 1B.

Example 67C

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid The title compound was prepared by substituting EXAMPLE 67B for EXAMPLE 1E in EXAMPLE 59D. $^1$H NMR (300 MHz, dimethylsulfoxide-d$_6$) δ ppm 12.98 (s, 1H), 12.76 (s, 1H), 8.52 (dd, 1H), 8.16 (d, 1H), 7.62 (d, 1H), 7.57-7.42 (m, 3H), 7.37 (t, 1H), 7.26 (s, 1H), 6.96 (d, 1H), 4.95 (s, 2H), 3.96 (s, 1H), 3.92-3.82 (m, 4H), 3.02 (t, 2H), 2.14 (s, 3H), 2.08 (s, 2H), 1.73 (m, 4H), 1.56 (m, 6H).

Example 68

6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid

Example 68A

N-(3-bromo-2-methylphenyl)-N-methyl-2-oxatricyclo[3.3.1.1$^{3,7}$]decyl-1-carboxamide A mixture of oxatricyclo[3.3.1.1$^{3,7}$]dec-1-yl)-2-carboxylic acid (137 mg) and oxalyl chloride (0.132 mL) in dichloromethane (3 mL) was stirred for 4 days. 3-Bromo-N,2-dimethylaniline (451 mg) and triethylamine (0.2 mL) were added, and the reaction mixture was stirred for 24 hours. The mixture was chromatographed on silica gel using 1-10% ethyl acetate in hexanes to give the desired product.

Example 68B tert-butyl 6-(8-(benzo[d]thiazol-2-ylcarbamoyl)-3,4-dihydroisoquinolin-2(1H)-yl)-3-(2-methyl-3-(N-methyl-2-oxatricyclo[33.3.1.1$^{3,7}$]decyl-1-carboxamido)phenyl)picolinate The title compound was prepared by substituting EXAMPLE 68A for EXAMPLE 20A in EXAMPLE 20B.

Example 68C

6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid The title compound was prepared by substituting EXAMPLE 68B for EXAMPLE 2B in EXAMPLE 2C. $^1$H NMR (300 MHz, dimethylsulfoxide-d$_6$) δ ppm 12.65 (br s, 1H), 8.02 (d, 1H), 7.77 (d, 1H), 7.63 (d, 1H), 7.40 (m, 5H), 7.09 (m, 2H), 6.96 (m, 3H), 4.99 (s, 2H), 3.91 (t, 2H), 3.48 (m, 2H), 3.00 (s, 3H), 2.18 (m, 2H), 1.75-2.01 (m, 9H), 1.69 (m, 2H), 1.51 (m, 1H), 1.33 (m, 2H).

Example 69

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid

Example 69A 3-bromo-N,2-dimethyl-N-(tricyclo[3.3.1.1$^{3,7}$]dec-2-yl)benzenesulfonamide The title compound was prepared by substituting N-methyladamant-2-ylamine for 1-adamantanamine in EXAMPLE 51A.

Example 69B

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid ter-butyl ester The title compound was prepared by substituting EXAMPLE 69A for EXAMPLE 20A in EXAMPLE 20B.

Example 69C

6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid The title compound was prepared by substituting EXAMPLE 69B for EXAMPLE 2B in EXAMPLE 2C. $^1$H NMR (400 MHz, dimethylsulfoxide-d$_6$) δ ppm 12.85 (bs, 1H), 12.63 (bs, 1H), 8.03 (d, 1H), 7.78 (m, 2H), 7.63 (d, 1H), 7.49-7.34 (m, 6H), 7.31 (td, 1H), 7.03 (d, 1H), 5.01 (bs, 2H), 3.94 (t, 2H), 3.04 (t, 2H), 2.92 (s, 3H), 2.26 (s, 3H), 2.17 (bs, 2H), 1.81-1.69 (m, 9H), 1.63 (bs, 2H), 1.45 (d, 2H).

Example 70

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfonyl)-3,4'-bipyridine-2-carboxylic acid To a cooled (0° C.) solution of EXAMPLE 74B (150 mg) in dichloromethane (10 mL) was added m-chloroperoxybenzoic acid (100 mg, 77%). The mixture was stirred at 0° C. for 30 minutes. The mixture was diluted with ethyl acetate (200 mL) and washed with aqueous Na$_2$S$_2$O$_3$, aqueous NaHCO$_3$, water, and brine and dried over Na$_2$SO$_4$. After filtration, the mixture was concentrated and the crude product was loaded on a column and eluted with 20% ethyl acetate in dichloromethane to give the expected product. The pure ester was then dissolved in dichloromethane/TFA (1:1, 10 mL) and stirred at room temperature overnight. After filtration, the mixture was concentrated and the residue was dissolved in dichloromethane and loaded on a column and eluted with 5% methanol in dichloromethane to provide the title compound. $^1$H NMR (300 MHz, dimethylsulfoxide-d$_6$) δ ppm 12.86 (s, 1H), 8.56 (d, 1H), 8.03 (d, 1H), 7.79 (d, 1H), 7.63 (d, 1H), 7.57 (d, 1H), 7.40 (m, 6H), 7.09 (d, 1H), 5.03 (s, 3H), 3.96 (t, 2H), 3.04 (t, 2H), 2.34 (s, 3H), 2.07 (m, 4H), 1.97 (m, 6H), 1.60 (m, 6H).

Example 71

6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1$^{3,7}$]dec-1-ylmethyl)-1H-pyrrol-3-yl]pyridine-2-carboxylic acid

Example 71A 5-methyl-1-(2-oxa-tricyclo[3.3.1.1$^{3,7}$]dec-1-ylmethyl)-1H-pyrrole-2-carbonitrile The title compound was prepared by substituting 1-hydroxymethyl-2-oxadamantane for 1-adamantanemethanol and 2-cyano-5-methylpyrrole for 3,5-dimethyl-4-(4,4,5,5-tetramethyl-1,3,2-dioxaborolan-2-yl)-1H-pyrazole in EXAMPLE 2A.

Example 71B 4-bromo-5-methyl-1-(2-oxa-tricyclo[3.3.1.1$^{3,7}$]dec-1-ylmethyl)-1H-pyrrole-2-carbonitrile The title compound was prepared by substituting EXAMPLE 71A for EXAMPLE 3B in EXAMPLE 3C.

Example 71C methyl 6-(8-(benzo[d]thiazol-2-ylcarbamoyl)-3,4-dihydroisoquinolin-2(1H)-yl)-3-bromopicolinate The title compound was prepared by substituting methyl 3-bromo-6-fluoropicolinate for EXAMPLE 1D in EXAMPLE 1E.

Example 71D methyl 6-(8-(benzo[d]thiazol-2-ylcarbamoyl)-3,4-dihydroisoquinolin-2(1H)-yl)-3-(4,4,5,5-tetramethyl-1,3,2-dioxaborolan-2-yl)picolinate To a solution of EXAMPLE 71C (500 mg), [1,1'-bis(diphenylphosphino)ferrocene]dichloropalladium(II) dichloromethane (46.8 mg) and triethylamine (0.399 mL) in acetonitrile (7 mL) and tetrahydrofuran (3.5 mL) was added 4,4,5,5-tetramethyl-1,3,2-dioxaborolane (0.416 mL). The mixture was heated at 100° C. in a Biotage Initiator microwave reactor for 30 minutes, cooled, diluted with ethyl acetate, and washed with brine. The organic layer was concentrated. The residue was purified by flash chromatography, eluting with 0-17% ethyl acetate in dichloromethane to provide the title compound.

Example 71E

6-[8-(Benzothiazol-2-ylcarbamoyl)-3,4-dihydro-1H-isoquinolin-2-yl]-3-[5-cyano-2-methyl-1-(2-oxa-tricyclo[3.3.1.1$^{3,7}$]dec-1-ylmethyl)-1H-pyrrol-3-yl]-pyridine-2-carboxylic acid methyl ester The title compound was prepared by substituting EXAMPLE 71D for EXAMPLE 4B and EXAMPLE 71B for EXAMPLE 20A in EXAMPLE 20B.

Example 71F

6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1$^{3,7}$]dec-1-ylmethyl)-1H-pyrrol-3-yl]pyridine-2-carboxylic acid The title compound was prepared by substituting EXAMPLE 71E for EXAMPLE 72C in EXAMPLE 72D. $^1$H NMR (500 MHz, dimethylsulfoxide-d$_6$) δ ppm 12.86 (s, 2H), 8.04 (d, 1H), 7.79 (d, 1H), 7.62 (d, 1H), 7.42-7.50 (m, 3H), 7.33-7.39 (m, 2H), 6.95 (d, 1H), 6.78 (s, 1H), 4.96 (s, 2H), 3.97 (s, 1H), 3.85-3.92 (m, 4H), 3.01 (t, 2H), 2.12 (s, 5H), 1.69-1.85 (m, 4H), 1.52-1.65 (m, 6H).

Example 72

6-[8-(1,3-benzothiazol-2-ylcarbamoyl)-3,4-dihydroisoquinolin-2(1H)-yl]-3-{5-cyano-2-methyl-1-[(3-methyl-2-oxatricyclo[3.3.1.1$^{3,7}$]dec-1-yl)methyl]-1H-pyrrol-3-yl}pyridine-2-carboxylic acid

Example 72A 5-methyl-1-(3-methyl-2-oxa-tricyclo[3.3.1.1$^{3,7}$]dec-1-ylmethyl)-1H-pyrrole-2-carbonitrile The title compound was prepared by substituting 1-hydroxymethyl-3-methyl-2-oxadamantane for 1-adamantanemethanol and 2-cyano-5-methylpyrrole for 3,5-dimethyl-4-(4,4,5,5-tetramethyl-1,3,2-dioxaborolan-2-yl)-1H-pyrazole in EXAMPLE 2A.

Example 72B 4-bromo-5-methyl-1-(3-methyl-2-oxa-tricyclo[3.3.1.1$^{3,7}$]dec-1-ylmethyl)-1H-pyrrole-2-carbonitrile The title compound was prepared by substituting EXAMPLE 72A for EXAMPLE 3B in EXAMPLE 3C.

Example 72C

6-[8-(benzothiazol-2-ylcarbamoyl)-3,4-dihydro-1H-isoquinolin-2-yl]-3-[5-cyano-2-methyl-1-(3-methyl-2-oxa-tricyclo[3.3.1.1$^{3,7}$]dec-1-ylmethyl)-1H-pyrrol-3-yl]-pyridine-2-carboxylic acid methyl ester The title compound was prepared by substituting EXAMPLE 71D for EXAMPLE 4B and EXAMPLE 72B for EXAMPLE 20A in EXAMPLE 20B.

Example 72D

6-[8-(benzothiazol-2-ylcarbamoyl)-3,4-dihydro-1H-isoquinolin-2-yl]-3-[5-cyano-2-methyl-1-(3-methyl-2-oxa-tricyclo[3.3.1.1$^{3,7}$]dec-1-ylmethyl)-1H-pyrrol-3-yl]pyridine-2-carboxylic acid EXAMPLE 72C (80 mg) in tetrahydrofuran (8 mL) and methanol (3 mL) was treated with 2N aqueous NaOH (3 mL) overnight. The reaction mixture was concentrated and the residue was purified by reverse phase chromatography using a Gilson system, eluting with 40%-100% acetonitrile in 0.1% TFA water solution to provide the title compound. $^1$H NMR (500 MHz, dimethylsulfoxide-d$_6$) δ ppm 12.86 (s, 1H), 8.04 (d, 1H), 7.79 (d, 1H), 7.62 (d, 1H), 7.42-7.49 (m, 3H), 7.36 (q, 2H), 6.95 (d, 1H), 6.77 (s, 1H), 4.96 (s, 2H), 3.87-3.91 (m, 4H), 3.01 (t, 2H), 2.11-2.17 (m, 5H), 1.63-1.74 (m, 2H), 1.56 (d, 2H), 1.38-1.51 (m, 6H), 1.00 (s, 3H).

Example 73

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 73A

Imidazo[1,2-a]pyrazin-2-amine 2,2,2-Trifluoro-N-(imidazo[1,2-a]pyrazin-2-yl)acetamide (prepared as described in WO2004/058266A1, 520 mg) was dissolved in 7N NH$_3$ in methanol (4.0 mL), and heated at 68° C. in a sealed tube for 6 hours. The reaction mixture was then cooled and concentrated to provide the title compound.

Example 73B

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid tert-butyl ester The title compound was prepared by substituting EXAMPLE 73A for thiazolo[4,5-b]pyridine-2-amine in EXAMPLE 30D, with the exception that 1/1 CH$_2$Cl$_2$/ethyl acetate, then 100% ethyl acetate were used for the eluents.

Example 73C

6-[8-(imidazo[1,2-a]pyrazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid EXAMPLE 73B (85 mg) was dissolved in dichloromethane (1.5 mL) and trifluoroacetic acid (1.5 mL). After stirring at room temperature overnight the reaction mixture was concentrated, then dissolved in CH$_2$Cl$_2$ (10 mL) and washed with water (5×15 mL). The organic layer was dried over Na$_2$SO$_4$. After filtration and concentration, the residue was triturated with CH$_3$CN (10 mL) to provide the title compound. $^1$H NMR (500 MHz, dimethylsulfoxide-d$_6$) δ ppm 11.49 (br s, 1H), 8.93 (s, 1H), 8.64 (dd, 1H), 8.55 (s, 1H), 7.92 (d, 1H), 7.51 (m, 2H), 7.37 (d, 1H), 7.33 (t, 1H), 7.27 (s, 1H), 6.90 (d, 1H), 4.92 (s, 2H), 3.88 (t, 2H), 3.70 (s, 2H), 3.02 (t, 2H), 2.10 (s, 3H), 1.92 (br s, 3H), 1.64 (br d, 3H), 1.54 (br m, 9H).

Example 74

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid

Example 74A tert-butyl 6-(8-(benzo[d]thiazol-2-ylcarbamoyl)-3,4-dihydroisoquinolin-2(1H)-yl)-2'-fluoro-3'-methyl-3,4'-bipyridine-2-carboxylate The title compound was prepared by substituting 2-fluoro-4-iodo-3-methylpyridine for EXAMPLE 20A in EXAMPLE 20B.

Example 74B tert-butyl 6-(8-(benzo[d]thiazol-2-ylcarbamoyl)-3,4-dihydroisoquinolin-2(1H)-yl)-2'-(tricyclo[3.3.1.1$^{3,7}$]dec-1-an-3-ylthio)-3'-methyl-3,4'-bipyridine-2-carboxylate To a solution of EXAMPLE 74A (130 mg) in N,N-dimethylacetamide (4 mL) was added 1-adamantanethiol (111 mg) and Cs$_2$CO$_3$ (215 mg). The mixture was stirred at 120° C. under microwave conditions (Biotage) for 2 hours. The mixture was diluted with ethyl acetate (200 mL) and washed with water and brine and dried over Na$_2$SO$_4$. After filtration and evaporation of the solvent, the crude material was loaded on a column and eluted with 20% ethyl acetate in dichloromethane to provide the title compound.

Example 74C

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid The title compound was prepared by substituting EXAMPLE 74B for EXAMPLE 2B in EXAMPLE 2C. $^1$H NMR (300 MHz, dimethylsulfoxide-d$_6$) δ ppm 12.85 (s, 1H), 8.25 (d, 1H), 8.03 (d, 1H), 7.79 (d, 1H), 7.62 (d, 1H), 7.43 (m, 5H), 7.03 (d, 1H), 6.83 (d, 1H), 5.00 (s, 2H), 3.93 (t, 2H), 3.03 (t, 2H), 2.26 (m, 5H), 2.01 (m, 3H), 1.95 (s, 3H), 1.71 (m, 6H).

Example 75

2-{6-[(methylsulfonyl)carbamoyl]-5-[5-methyl-1-(tricyclo[3.3.1.1$^{3,7}$]dec-1-ylmethyl]-1H-pyrazol-4-yl]pyridin-2-yl}-N-([1,3]thiazolo[5,4-b]pyridin-2-yl)-1,2,3,4-tetrahydroisoquinoline-8-carboxamide The title compound was prepared by substituting EXAMPLE 24B for EXAMPLE 3F in EXAMPLE 17, with the exception that chromatography on silica gel using 70/30/1 hexanes/ethyl acetate/acetic acid was used for the purification. $^1$H NMR (400 MHz, dimethylsulfoxide-d$_6$) δ ppm 11.82 (br s, 1H), 8.52 (dd, 1H), 8.15 (dd, 1H), 7.63 (d, 1H), 7.52 (m, 2H), 7.38 (t, 1H), 7.33 (t, 1H), 7.27 (s, 1H), 7.02 (d, 1H), 4.97 (s, 2H), 3.93 (t, 2H), 3.70 (s, 2H), 3.12 (s, 3H), 3.03 (t, 2H), 2.11 (s, 3H), 1.92 (br s, 3H), 1.64 (br d, 3H), 1.54 (br m, 9H).

Example 76

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid

Example 76A 4-iodo-3-methyl-N-(tricyclo[3.3.1.1$^{3,7}$]dec-1-yl)pyridin-2-amine The title compound was prepared by substituting adamantine-1-amine for cyclooctanamine in EXAMPLE 61A.

Example 76B

2'-(adamantan-1-ylamino)-6-[8-(benzothiazol-2-ylcarbamoyl)-3,4-dihydro-1H-isoquinolin-2-yl]-3'-methyl-[3,4']bipyridinyl-2-carboxylic acid tert-butyl ester The title compound was prepared by substituting EXAMPLE 76A for EXAMPLE 20A in EXAMPLE 20B.

Example 76C

6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid EXAMPLE 76B (100 mg) in tetrahydrofuran (8 mL) and methanol (5 mL) was treated with 2 N aqueous NaOH (5 mL) at 50° C. for 5 days, cooled, and acidified to pH 1. The mixture was concentrated and the residue was purified reverse phase chromatography using a Gilson system, eluting with 30%-70% acetonitrile in 0.1 TFA/water to provide the title compound. $^1$H NMR (500 MHz, dimethylsulfoxide-d$_6$) δ ppm 12.87 (s, 2H), 8.03 (d, 1H), 7.83 (d, 1H), 7.79 (d, 1H), 7.64 (d, 1H), 7.44-7.52 (m, 3H), 7.33-7.40 (m, 2H), 7.07 (d, 1H), 6.63 (s, 1H), 5.03 (s, 2H), 3.95 (s, 2H), 3.03 (t, 2H), 1.93 (s, 3H), 1.71-1.81 (m, 3H), 1.63-1.70 (m, 3H).

Example 77

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid

Example 77A

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid tert-butyl ester The title compound was prepared by substituting imidazo[1,2-b]pyridazin-2-amine for thiazolo[4,5-b]pyridine-2-amine in EXAMPLE 30D, with the exception that 45-60% ethyl acetate in CHCl$_3$ was used for the eluent.

Example 77B

6-[8-(imidazo[1,2-b]pyridazin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid The title compound was prepared by substituting EXAMPLE 77A for EXAMPLE 1F in EXAMPLE 1G. $^1$H NMR (400 MHz, dimethylsulfoxide-d$_6$) δ ppm 11.41 (br s, 1H), 8.50 (dd, 1H), 8.49 (s, 1H), 8.02 (d, 1H), 7.49 (m, 2H), 7.37 (d, 1H), 7.33 (t, 1H), 7.27 (s, 1H), 7.25 (dd, 1H), 6.92 (d, 1H), 4.92 (s, 2H), 3.88 (t, 2H), 3.71 (s, 2H), 3.00 (t, 2H), 2.10 (s, 3H), 1.93 (br s, 3H), 1.64 (br d, 3H), 1.54 (br m, 9H).

Example 78

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid

Example 78A

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid tert-butyl ester The title compound was prepared by substituting thiazolo[5,4-c]pyridin-2-amine for thiazolo[4,5-b]pyridine-2-amine in EXAMPLE 30D.

Example 78B

3-[5-methyl-1-(tricyclo[3.3.1.1$^{3,7}$]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid The title compound was prepared by substituting EXAMPLE 78A for EXAMPLE 2B in EXAMPLE 2C. $^1$H NMR (300 MHz, dimethylsulfoxide-d$_6$) δ ppm 13.77-13.39 (s, 1H), 12.75 (s, 1H), 9.46 (s, 1H), 8.70 (d, 1H), 8.03 (d, 1H), 7.71-7.64 (m, 1H), 7.55-7.45 (m, 2H), 7.40 (t, 1H), 7.26 (s, 1H), 6.97 (d, 1H), 4.98 (s, 2H), 3.89 (m, 2H), 3.70 (s, 2H), 3.02 (t, 2H), 2.10 (s, 3H), 1.92 (s, 3H), 1.60 (m, 12H).

Example 79

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid

Example 79A

Spiro[2.5]octan-5-one

3-Ethoxycyclohex-2-enone (25 g) was dissolved in diethyl ether (500 mL), and tetraisopropoxytitanium (55 mL) was added, followed by the addition of ethyl magnesium bromide (3.0 M in diethyl ether, 180 mL) over 30 minutes. The reaction was stirred at room temperature for another two hours, and quenched by the careful addition of water (250 mL). The mixture was filtered through diatomaceous earth, and rinsed with diethyl ether. The filtrate was transferred to a separatory funnel, the aqueous layer was drawn off, and p-toluenesulfonic acid monohydrate (2 g) was added to the organic layer, which was stirred at room temperature for two days. The reaction mixture was washed with saturated aqueous NaHCO$_3$ and brine, then dried over Na$_2$SO$_4$. The mixture was filtered, and concentrated and chromatography on silica gel using 93/7 hexanes/ethyl acetate provided the title compound.

Example 79B 5-((5-methyl-1H-pyrazol-1-yl)methyl)spiro[2.5]octan-5-ol

Tetrahydrofuran (50 mL) was cooled to −76° C., n-butyllithium (2.5M in tetrahydrofuran, 7.0 mL) was added, and the solution was cooled back to −76° C. 1,5-Dimethyl-1H-pyrazole (1.5 g) was added dropwise, and the reaction was stirred for 75 minutes. EXAMPLE 79A (2.15 g) was added dropwise, and the mixture was stirred for another 15-20 minutes. The reaction mixture was warmed to room temperature, and partitioned between saturated NH$_4$Cl and ethyl acetate. The organic layer was washed with brine, dried over Na$_2$SO$_4$, filtered, and concentrated. Chromatography on silica gel using 4/1 hexanes/ethyl acetate provided the title compound.

Example 79C 1-((5-methoxyspiro[2.5]octan-5-yl)methyl)-5-methyl-1H-pyrazole

EXAMPLE 79B (1 g) was dissolved in N,N-dimethylformamide (15 mL), then iodomethane (0.85 mL) and 95% sodium hydride (340 mg) were added. The reaction was stirred at room temperature for 2.5 hours, then diluted with water and extracted with ethyl acetate. The organic layer was washed with brine and dried over sodium sulfate. Filtration and concentration provided the title compound.

Example 79D 4-bromo-1-((5-methoxyspiro[2.5]octan-5-yl)methyl)-5-methyl-1H-pyrazole EXAMPLE 79C (1.1 g) was dissolved in N,N-dimethylformamide (12 mL), and N-bromosuccinimide (840 mg) was added. The reaction mixture was stirred at room temperature for 2.5 hours, and diluted with water and extracted with ethyl acetate. The organic layer was washed with 20% aqueous Na$_2$SO$_3$ and brine. The organic layer was dried over Na$_2$SO$_4$, filtered and concentrated to provide the title compound.

Example 79E 1-((5-methoxyspiro[2.5]octan-5-yl)methyl)-5-methyl-4-(4,4,5,5-tetramethyl-1,3,2-dioxaborolan-2-yl)-1H-pyrazole The title compound was prepared by substituting EXAMPLE 79D for EXAMPLE 3C in EXAMPLE 3D.

Example 79F

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid tert-butyl ester The title compound was prepared by substituting EXAMPLE 79E for EXAMPLE 3D and EXAMPLE 1E for EXAMPLE 14C in EXAMPLE 14D.

Example 79G

6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid EXAMPLE 79F (40 mg) was dissolved in tetrahydrofuran (0.2 mL) and methanol (0.3 mL). To the mixture was added 1N LiOH (0.35 mL), and the reaction mixture was stirred at 60° C. overnight. After cooling to room temperature, the mixture was diluted with water (5 mL), 2N aqueous HCl (0.18 mL) was added, and the solution was extracted with ethyl acetate and concentrated. The residue was purified by Prep HPLC using a Gilson system eluting with 20-80% acetonitrile in 0.1% water. The desired fractions were combined and freeze-dried to provide the title compound. $^1$H NMR (500 MHz, dimethylsulfoxide-d$_6$) δ ppm 12.85 (v br s, 1H), 8.04 (d, 1H), 7.79 (d, 1H), 7.62 (d, 1H), 7.48 (m, 2H), 7.43 (d, 1H), 7.36 (m, 2H), 7.28 (s, 1H), 6.95 (d, 1H), 4.96 (s, 2H), 4.19 (d, 1H), 4.09 (d, 1H), 3.89 (t, 2H), 3.09 (s, 3H), 3.01 (t, 2H), 2.12 (s, 3H), 1.58 (br m, 3H), 1.43 (br m, 3H), 1.20 (br m, 2H), 0.31 (br m, 2H), 0.23 (br m, 2H).

Example 80

6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid

Example 80A

1-[(3-{2-[2-(2-methoxyethoxy)ethoxy]ethoxy}tricyclo[3.3.1.1$^{3,7}$]dec-1-yl)methyl]-1H-pyrazole The title compound was prepared by substituting EXAMPLE 26A for EXAMPLE 7A and 2-(2-(2-methoxyethoxy)ethoxy)ethanol for methanol in EXAMPLE 7B.

Example 80B

1-1-{[3-{2-[2-(2-methoxyethoxy)ethoxy]ethoxy}tricyclo[3.3.1.1$^{3,7}$]dec-1-yl]methyl}-5-methyl-1H-pyrazole The title compound was prepared by substituting EXAMPLE 80A for EXAMPLE 3A in EXAMPLE 3B.

Example 80C

1-{[3-{2-[2-(2-methoxyethoxy)ethoxy]ethoxy}tricyclo[3.3.1.1$^{3,7}$]dec-1-yl]methyl})-4-bromo-5-methyl-1H-pyrazole The title compound was prepared by substituting EXAMPLE 80B for EXAMPLE 3B in EXAMPLE 3C, with the modification that the title compound was purified by RP-HPLC on a Gilson system, eluting with a gradient of 20% to 100% acetonitrile in water containing 0.1% v/v trifluoroacetic acid.

Example 80D tert-butyl 6-(8-(benzo[d]thiazol-2-ylcarbamoyl)-3,4-dihydroisoquinolin-2(1H)-yl)-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)picolinate The title compound was prepared by substituting EXAMPLE 80C for EXAMPLE 4A in EXAMPLE 4C.

Example 80E

6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid The title compound was prepared by substituting EXAMPLE 80D for EXAMPLE 2B in EXAMPLE 2C. $^1$H NMR (300 MHz, dimethylsulfoxide-d$_6$) δ ppm 12.84 (bs, 1H), 8.03 (d, 1H), 7.79 (d, 1H), 7.61 (d, 1H), 7.41 (m, 5H), 7.27 (s, 1H), 6.94 (d, 1H), 4.95 (s, 2H), 3.89 (t, 2H), 3.78 (s, 1H), 3.49 (m, 6H), 3.43 (m, 6H), 3.22 (s, 3H), 3.02 (t, 2H), 2.11 (m, 5H), 1.53 (m, 12H).

Example 81

6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid

Example 81A

3-(1H-pyrazol-1-ylmethyl)tricyclo[3.3.1.1$^{3,7}$]decane-1-thiol

A solution of EXAMPLE 26A (2.0 g) and thiourea (2.0 g) in a solvent mixture of acetic acid (20 mL) and 48% aqueous HBr solution (10 mL) was heated to 100° C. for 24 hours. The reaction was concentrated to dryness, and the residue was dissolved in 20% v/v ethanol in water (100 mL). Solid sodium hydroxide (10 g) was added, and the mixture was stirred overnight. The solution was acidified to pH 1 with concentrated HCl solution, and diluted with ethyl acetate (100 mL). The layers were separated, and the aqueous layer was extracted with additional ethyl acetate (2×100 mL). The combined organic layers were washed with water, dried over Na$_2$SO$_4$, filtered, and concentrated. The residue was purified by silica gel chromatography, eluting with a gradient of 10-50% ethyl acetate in hexane, to give the title product.

Example 81B

1-{[3-(methylsulfanyl)tricyclo[3.3.1.1$^{3,7}$]dec-1-yl]methyl}-1H-pyrazole To a solution of EXAMPLE 81A (300 mg) in methanol (2 mL) was added sodium methoxide (4 mL, 0.5 M in methanol). Iodomethane (0.5 mL) was added, and the reaction heated to reflux for 3 hours. The reaction was cooled to room temperature and concentrated to dryness. The residue war purified by reverse phase HPLC, eluting with a gradient of 30% to 100% acetonitrile in water containing 0.1% v/v trifluoroacetic acid, to give the title product.

Example 81C

5-methyl-1-{[3-(methylsulfanyl)tricyclo[3.3.1.1$^{3,7}$]dec-1-yl]methyl}-1H-pyrazole The title compound was prepared by substituting EXAMPLE 81B for EXAMPLE 3A in EXAMPLE 3B.

Example 81D

4-bromo-5-methyl-1-{[3-(methylsulfonyl)tricyclo[3.3.1.1$^{3,7}$]dec-1-yl]methyl}-1H-pyrazole To a solution of EXAMPLE 81C (98 mg) in water (2 mL) was added N-bromosuccinimide (150 mg), and the reaction mixture was heated to reflux for 3 hours. Additional N-bromosuccinimide (50 mg) was added, and the reaction was heated to reflux for 24 hours. The reaction mixture was cooled to room temperature and diluted with methylene chloride. The layers were separated, and the aqueous layer was extracted with additional methylene chloride (twice). The combined organic layers were washed with water, dried over Na$_2$SO$_4$, filtered, and concentrated. The residue was purified by flash chromatography, eluting with a gradient of 0-50% ethyl acetate in hexane, to provide the title compound.

Example 81E tert-butyl 6-(8-(benzo[d]thiazol-2-ylcarbamoyl)-3,4-dihydroisoquinolin-2(1H)-yl)-3-(5-methyl-1-{[3-(methylsulfonyl)tricyclo[3.3.1.1$^{3,7}$]dec-1-yl]methyl}-1H-pyrazol-4-yl)picolinate The title compound was prepared by substituting EXAMPLE 81D for EXAMPLE 4A in EXAMPLE 4C.

Example 81F

6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid The title compound was prepared by substituting EXAMPLE 81E for EXAMPLE 2B in EXAMPLE 2C. $^1$H NMR (300 MHz, dimethylsulfoxide-d$_6$) δ ppm 12.85 (bs, 1H), 8.04 (d, 5, 1H), 7.79 (d, 1H), 7.61 (d, 1H), 7.48 (m, 3H), 7.36 (d, 2H), 7.30 (s, 1H), 6.95 (d, 1H), 4.95 (s, 2H), 3.89 (t, 2H), 3.80 (s, 2H), 3.02 (d, 2H), 2.19 (m, 11H), 1.57 (m, 6H).

Example 82

6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid

Example 82A

2-{[3,5-dimethyl-7-(1H-pyrazol-1-ylmethyl)tricyclo[3.3.1.1$^{3,7}$]dec-1-yl]oxy}ethanol To a solution of EXAMPLE 38C (4.5 g) in ethane-1,2-diol (12 mL) was added triethylamine (3 mL) under nitrogen. The mixture was heated to 150° C. under microwave conditions (Biotage) for 45 minutes. The mixture was poured over water (100 mL) and extracted with ethyl acetate (3×200 mL). The combined organic layers were washed with water and brine, dried with Na$_2$SO$_4$, filtered and concentrated. The residue was purified by silica gel chromatography, eluting with 20% ethyl acetate in hexane (1 L) followed by 5% methanol in methylene chloride (1 L), to give the title product.

Example 82B 2-({3,5-dimethyl-7-[(5-methyl-1H-pyrazol-1-yl)methyl]tricyclo[3.3.1.1$^{3,7}$]dec-1-yl}oxy)ethanol To a cold (−78° C.) solution of the EXAMPLE 82A (3.69 g) in tetrahydrofuran (50 mL) was added n-BuLi (20 mL, 2.5 M in hexane) under nitrogen. The mixture was stirred at −78° C. for 1.5 hours. Iodomethane (10 mL) was added by syringe, and the mixture was stirred for an additional 3 hours. The reaction mixture was then quenched by the addition of aqueous ammonium chloride solution and extracted with ethyl acetate (2×200 mL). The combined organic layers were washed with water (60 mL) and brine (60 mL), dried with Na$_2$SO$_4$, filtered and concentrated. The residue was purified by silica gel column chromatography, eluting with 5% methanol in methylene chloride, to give the title compound.

Example 82C 1-({3,5-dimethyl-7-[2-(hydroxy)ethoxy]tricyclo[3.3.1.1$^{3,7}$]dec-1-yl}methyl)-4-iodo-5-methyl-1H-pyrazole The title compound was prepared by substituting EXAMPLE 82B for EXAMPLE 16D in EXAMPLE 16E.

Example 82D 2-({3-[(4-iodo-5-methyl-1H-pyrazol-1-yl)methyl]-5,7-dimethyltricyclo[3.3.1.1$^{3,7}$]dec-1-yl}oxy)ethyl methanesulfonate To a cold (0° C.) solution of EXAMPLE 82C (2.1 g) in methylene chloride (30 mL) was added triethylamine (1.42 g) followed by methanesulfonyl chloride (0.542 g). The mixture was stirred at room temperature for 1.5 hours and then was diluted with ethyl acetate (300 mL). The layers were separated, and the organic layer was washed with water (60 mL) and brine (60 mL), dried with Na$_2$SO$_4$, filtered and concentrated to give the title compound, which was used in the next step without further purification.

Example 82E 1-({3,5-dimethyl-7-[2-(methylamino)ethoxy]tricyclo[3.3.1.1$^{3,7}$]dec-1-yl}methyl)-4-iodo-5-methyl-1H-pyrazole A solution of the EXAMPLE 82D (2.5 g) in 2 M methylamine in methanol (15 mL) was heated to 100° C. for 20 minutes under microwave conditions (Biotage). The reaction mixture was concentrated, and the residue was diluted with ethyl acetate (400 mL). The organic layer was washed with saturated aqueous NaHCO$_3$ solution (60 mL), water (60 mL) and brine (60 mL). The organic layer was dried with Na$_2$SO$_4$, filtered and concentrated to give the title compound, which was used in the next reaction without further purification.

Example 82F tert-butyl [2-({3-[(4-iodo-5-methyl-1H-pyrazol-1-yl)methyl]-5,7-dimethyltricyclo[3.3.1.1$^{3,7}$]dec-1-yl}oxy)ethyl]methylcarbamate To a solution of EXAMPLE 82E (2.2 g) in tetrahydrofuran (30 mL) was added Boc$_2$O (1.26 g) and a catalytic amount of 4-dimethylaminopyridine. The mixture was stirred at room temperature for 1.5 hours and diluted with ethyl acetate (300 mL). The solution was washed with saturated aqueous NaHCO$_3$, water (60 mL) and brine (60 mL). The organic layer was dried with Na$_2$SO$_4$, filtered and concentrated. The residue was purified by silica gel chromatography, eluting with 20% ethyl acetate in methylene chloride, to give the title compound.

Example 82G tert-butyl {2-[(3,5-dimethyl-7-{[5-methyl-4-(4,4,5,5-tetramethyl-1,3,2-dioxaborolan-2-yl)-1H-pyrazol-1-yl]methyl}tricyclo[3.3.1.1$^{3,7}$]dec-1-yl)oxy]ethyl}methylcarbamate The title compound was prepared by substituting EXAMPLE 82F for EXAMPLE 59B in EXAMPLE 59C.

Example 82H tert-butyl 6-[8-(1,3-benzothiazol-2-ylcarbamoyl)-3, 4-dihydroisoquinolin-2(1H)-yl]-3-{1-[(3-{2-[(tert-butoxycarbonyl)(methyl)amino]ethoxy}-5,7-dimethyltricyclo[3.3.1.1$^{3,7}$]dec-1-yl)methyl]-5-methyl-1H-pyrazol-4-yl})pyridine-2-carboxylate A solution of a 3:1 ratio of dioxane and water (40 mL) was degassed with nitrogen for 45 minutes. This solution was added to EXAMPLE 1E (01.5 g), EXAMPLE 82G (1.48 g), potassium phosphate (02.82 g), tris(dibenzylideneacetone)dipalladium(0) chloroform adduct (0.121 g) and 1,3,5,7-tetramethyl-6-tetradecane-2,4,8-trioxa-6-phosphaadamantane (0.194 g). The mixture was degassed and heated to 90° C. under nitrogen overnight. The reaction mixture was cooled, diluted with ethyl acetate (100 mL), washed with water (three×50 mL) and brine (50 mL), dried over magnesium sulfate, filtered and concentrated. The residue was purified by silica gel chromatography, eluting with a gradient of 20% to 40% ethyl acetate in methylene chloride, to give the title compound.

Example 82I

6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid The title compound was prepared by substituting EXAMPLE 82H for EXAMPLE 2B in EXAMPLE 2C. $^1$H NMR (300 MHz, dimethylsulfoxide-d$_6$) δ ppm 12.85 (s, 1H), 8.21 (s, 1H), 8.03 (d, 1H), 7.79 (d, 1H), 7.62 (d, 1H), 7.43 (m, 4H), 6.96 (d, 1H), 4.96 (s, 2H), 3.89 (m, 6H), 3.54 (m, 2H), 3.01 (t, 4H), 2.55 (t, 3H), 2.10 (s, 3H), 1.42 (s, 2H), 1.31 (m, 4H), 1.08 (m, 6H), 0.87 (s, 6H).

Example 83

6-[8-(1,3-benzothiazol-2-ylcarbamoyl)-3,4-dihydroisoquinolin-2(1H)-yl]-3-(5-methyl-1-{[3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid

Example 83A

2-[2-(2-{[3-(1H-pyrazol-1-ylmethyl)tricyclo[3.3.1.1$^{3,7}$]dec-1-yl]oxy}ethoxy)ethoxy]ethanol The title compound was prepared by substituting EXAMPLE 26A for EXAMPLE 7A and 2,2'-(ethane-1,2-diylbis(oxy))diethanol for methanol in EXAMPLE 7B., with the modification that the title compound was purified by RP-HPLC on a Gilson system, eluting with a gradient of 20% to 100% acetonitrile in water containing 0.1% v/v trifluoroacetic acid.

Example 83B

2-{2-[2-({3-[(5-methyl-1H-pyrazol-1-yl)methyl]tricyclo[3.3.1.1$^{3,7}$]dec-1-yl}oxy)ethoxy]ethoxy}ethanol To a cold (−78° C.) solution of EXAMPLE 83A (1.0 g) in tetrahydrofuran (10 mL) was added n-BuLi (5 mL, 2.5 M in hexane). The reaction mixture was stirred for 90 minutes, and iodomethane (1 mL) was added. The reaction mixture was stirred at −78° C. for 90 minutes and quenched by the addition of 1 drop of trifluoroacetic acid. The reaction mixture was warmed to room temperature and concentrated to dryness. The residue was used in the subsequent step without further purification.

Example 83C

2-{2-[2-({3-[(4-iodo-5-methyl-1H-pyrazol-1-yl)methyl]tricyclo[3.3.1.1$^{3,7}$]dec-1-yl}oxy)ethoxy]ethoxy}ethanol To an ambient solution of EXAMPLE 83B (0.54 g) in N,N-dimethylformamide (5 mL) was added N-iodosuccinimide (0.35 g). The reaction mixture was stirred for 2 hours, and the crude reaction solution was purified by RP-HPLC on a Gilson system, eluting with a gradient of 20% to 100% acetonitrile in water containing 0.1% v/v trifluoroacetic acid, to give the title compound.

Example 83D

2-{2-[2-({3-[(4-iodo-5-methyl-1H-pyrazol-1-yl)methyl]tricyclo[3.3.1.1$^{3,7}$]dec-1-yl}oxy)ethoxy]ethoxy}-N-methylethanamine To a cold (0° C.) solution of EXAMPLE 83C (0.445 g) and triethylamine (0.5 mL) in tetrahydrofuran (10 mL) was added methanesulfonyl chloride (0.07 mL). The mixture was stirred for 3 hours and transferred to a 20-mL microwave reaction vessel. Methanamine (4 mL, 2 M in methanol) was added, and the mixture was heated to 100° C. for 20 minutes under microwave (Biotage) conditions. The reaction mixture was concentrated to dryness, and the residue was purified by reverse-phase chromatography (Analogix system, C18 SF40-300 g column), eluting with a gradient of 40-100% acetonitrile in water containing 0.1% v/v trifluoroacetic acid, to give the title product.

Example 83E tert-butyl (2-{2-[2-({3-[(4-iodo-5-methyl-1H-pyrazol-1-yl)methyl]tricyclo[3.3.1.1$^{3,7}$]dec-1-yl})oxy)ethoxy]ethoxy})ethyl)methylcarbamate The title compound was prepared by substituting EXAMPLE 83D for EXAMPLE 82E in EXAMPLE 82F.

Example 83F tert-butyl methyl[2-(2-{2-[(3-{[5-methyl-4-(4,4,5,5-tetramethyl-1,3,2-dioxaborolan-2-yl)-1H-pyrazol-1-yl]methyl}tricyclo[3.3.1.1$^{3,7}$]dec-1-yl)oxy]ethoxy}ethoxy)ethyl]carbamate The title compound was prepared by substituting EXAMPLE 83E for EXAMPLE 59B in EXAMPLE 59C.

Example 83G tert-butyl 6-[8-(1,3-benzothiazol-2-ylcarbamoyl)-3,4-dihydroisoquinolin-2(1H)-yl]-3-[5-methyl-1-({3-[(2,2,5-trimethyl-4-oxo-3,8,11-trioxa-5-azatridecan-13-yl)oxy]tricyclo[3.3.1.1$^{3,7}$]dec-1-yl}methyl)-1H-pyrazol-4-yl]pyridine-2-carboxylate The title compound was prepared by substituting EXAMPLE 83F for EXAMPLE 4A in EXAMPLE 4C.

Example 83H

6-[8-(1,3-benzothiazol-2-ylcarbamoyl)-3,4-dihydroisoquinolin-2(1H)-yl]-3-(5-methyl-1-{[(3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid The title compound was prepared by substituting EXAMPLE 83G for EXAMPLE 2B in EXAMPLE 2C. $^1$H NMR (300 MHz, dimethylsulfoxide-d$_6$) δ ppm 12.86 (bs, 1H), 8.37 (s, 1H), 8.04 (d, 1H), 7.79 (d, 1H), 7.62 (d, 1H), 7.47 (m, 2H), 7.36 (m, 2H), 7.28 (s, 1H), 6.95 (d, 1H), 4.96 (s, 1H), 3.88 (dd, 2H), 3.56 (m, 4H), 3.46 (m, 3H), 3.06 (m, 4H), 2.55 (m, 3H), 2.09 (m, 5H), 1.48 (m, 12H).

Example 84

6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid

Example 84A

Benzyl 8-azaspiro[bicyclo[3.2.1]octane-3,2'-oxirane]-8-carboxylate

To a 500-mL, three-necked, round-bottomed flask equipped with a magnetic stirring bar, a thermometer, and a condenser was charged tetrahydrofuran (163 mL), potassium tert-butoxide (6.6 g, 95% pure) and trimethylsulfoxonium iodide (13.0 g). The mixture was heated to reflux and stirred for 3 hours. A solution of benzyl 3-oxo-8-azabicyclo[3.2.1] octane-8-carboxylate (10.0 g) in tetrahydrofuran (37 mL) was added in one portion. The reaction mixture was refluxed for another 2 hours. The mixture was cooled to room temperature and diluted with toluene (100 mL) and water. The water layer was separated and extracted with toluene (2×50 mL). The combined organic layers were washed with water (3×40 mL) and concentrated under vacuum to provide the title compound.

Example 84B

Benzyl 3-formyl-8-azabicyclo[3.2.1]octane-8-carboxylate

To a cold (0° C.) solution of EXAMPLE 84A (3.5 g) in tetrahydrofuran (40 mL) was added boron trifluoride diethyl ether complex (0.82 mL). The mixture was stirred at 3-5° C. for 3 hours. Aqueous saturated NaHCO$_3$ was added, followed by ethyl acetate (200 mL). The organic layer was separated, washed with water (twice) and concentrated to dryness. Toluene was added and the mixture was concentrated under vacuum to provide the title compound.

Example 84C

Benzyl 3-(hydroxymethyl)-8-azabicyclo[3.2.1]octane-8-carboxylate

To a solution of EXAMPLE 84B (3.4 g) in tetrahydrofuran (40 mL) was added NaBH$_4$ (0.5 g). The mixture was stirred overnight. The solvent was evaporated and the residue was added to ethyl acetate (300 mL) and water (50 mL). The organic layer was washed with water and brine, dried over Na$_2$SO$_4$, and filtered. Evaporation of the solvent gave the crude title compound.

Example 84D

Benzyl 3-((4-(4,4,5,5-tetramethyl-1,3,2-dioxaborolan-2-yl)-1H-pyrazol-1-yl)methyl)-8-azabicyclo[3.2.1]octane-8-carboxylate The title compound was prepared by substituting EXAMPLE 84C for 1-adamantanemethanol and 4-(4,4,5,5-tetramethyl-1,3,2-dioxaborolan-2-yl)-1H-pyrazole for 3,5-dimethyl-4-(4,4,5,5-tetramethyl-1,3,2-dioxaborolan-2-yl)-1H-pyrazole in EXAMPLE 2A.

Example 84E

6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid The title compound was prepared by substituting EXAMPLE 84D for EXAMPLE 1A in EXAMPLE 1F, and then substituting that product for EXAMPLE 2B in EXAMPLE 2C. $^1$H NMR (300 MHz, dimethylsulfoxide-d$_6$) δ ppm 12.85 (s, 1H), 8.04 (d, 1H), 7.49 (m, 16H), 6.94 (d, 1H), 5.06 (m, 2H), 4.94 (s, 2H), 3.89 (m, 3H), 3.00 (m, 2H), 1.84 (m, 3H), 1.59 (m, 2H), 1.29 (m, 6H).

Example 85

6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid

Example 85A 1-(tricyclo[3.3.1.1$^{3,7}$]dec-1-ylmethyl)-5-bromopyridin-2(1H)-one To an ambient suspension of NaH (185 mg, 4.63 mmol, 60% dispersion in mineral oil) in N,N-dimethylformamide (30 mL) was added 5-bromopyridin-2(1H)-one (700 mg, 4.02 mmol). The reaction mixture was stirred for 15 minutes, and 1-(bromomethyl)adamantane (968 mg 4.22 mmol) was added. The mixture was heated to 120° C. overnight, cooled to room temperature, and quenched by the addition of water and ether. The layers were separated, and the aqueous extracted with additional ether (twice). The combined organics were washed with brine, dried over Na$_2$SO$_4$, and filtered. Chromatography on silica gel, eluting with a gradient of 5 to 30% ethyl acetate in hexanes, provided the title compound.

Example 85B tert-butyl 1'-(tricyclo[3.3.1.1$^{3,7}$]dec-1-ylmethyl)-6-(8-(benzo[d]thiazol-2-ylcarbamoyl)-3,4-dihydroisoquinolin-2(1H)-yl)-6'-oxo-1',6'-dihydro-[3,3'-bipyridine]-2-carboxylate The title compound was prepared by substituting EXAMPLE 85A for EXAMPLE 4A in EXAMPLE 4C.

Example 85C

6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid The title compound was prepared by substituting EXAMPLE 85B for EXAMPLE 2B in EXAMPLE 2C. $^1$H NMR (400 MHz, dimethylsulfoxide-d$_6$) δ ppm 12.85 (bs, 1H), 8.04 (d, 1H), 7.80 (d, 1H), 7.66-7.54 (m, 3H), 7.50-7.31 (m, 5H), 7.01 (d, 1H), 6.39 (d, 1H), 4.98 (s, 2H), 3.90 (t, 2H), 3.66 (s, 2H), 3.01 (t, 2H), 1.92 (bs, 3H), 1.68-1.46 (m, 12H).

Example 86

6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl}-5-methyl-1H-pyrazol-4-yl)pyridine-2-carboxylic acid

Example 86A

1-{[3,5-dimethyl-7-(2-{2-[2-(hydroxy)ethoxy]ethoxy}ethoxy)tricyclo[3.3.1.1$^{3,7}$]dec-1-yl]methyl}-1H-pyrazole The title compound was prepared by substituting EXAMPLE 38C for EXAMPLE 7A and 2,2'-(ethane-1,2-diylbis(oxy))diethanol for methanol in EXAMPLE 7B, with the modification that the title compound was purified by RP-HPLC on a Gilson system, eluting with a gradient of 20% to 100% acetonitrile in water containing 0.1% v/v trifluoroacetic acid.

Example 86B

1-{[3,5-dimethyl-7-(2-{2-[2-(hydroxy)ethoxy]ethoxy}ethoxy)tricyclo[3.3.1.1$^{3,7}$]dec-1-yl]methyl}-5-methyl-1H-pyrazole The title compound was prepared by substituting EXAMPLE 86A for EXAMPLE 83A in EXAMPLE 83B.

Example 86C

1-{[3,5-dimethyl-7-(2-{2-[2-(hydroxy)ethoxy]ethoxy}ethoxy)tricyclo[3.3.1.1$^{3,7}$]dec-1-yl]methyl}-4-iodo-5-methyl-1H-pyrazole The title compound was prepared by substituting EXAMPLE 86B for EXAMPLE 83B in EXAMPLE 83C.

Example 86D

1-{[3,5-dimethyl-7-(2-{2-[2-(methylamino)ethoxy]ethoxy}ethoxy)tricyclo[3.3.1.1$^{3,7}$]dec-1-yl]methyl}-4-iodo-5-methyl-1H-pyrazole The title compound was prepared by substituting EXAMPLE 86C for EXAMPLE 83C in EXAMPLE 83D.

Example 86E tert-butyl (2-{2-[2-({3-[(4-iodo-5-methyl-1H-pyrazol-1-yl)methyl]-5,7-dimethyltricyclo[3.3.1.1$^{3,7}$]dec-1-yl}oxy)ethoxy]ethoxy})ethyl)methylcarbamate The title compound was prepared by substituting EXAMPLE 86D for EXAMPLE 82E in EXAMPLE 82F.

Example 86F tert-butyl [2-(2-{2-[(3,5-dimethyl-7-{[5-methyl-4-(4,4,5,5-tetramethyl-1,3,2-dioxaborolan-2-yl)-1H-pyrazol-1-yl]methyl}tricyclo[3.3.1.1$^{3,7}$]dec-1-yl)oxy]ethoxy}ethoxy)ethyl]methylcarbamate The title compound was prepared by substituting EXAMPLE 86E for EXAMPLE 59B in EXAMPLE 59C.

Example 86G tert-butyl 6-[8-(1,3-benzothiazol-2-ylcarbamoyl)-3,4-dihydroisoquinolin-2(1H)-yl]-3-[1-({3,5-dimethyl-7-[(2,2,5-trimethyl-4-oxo-3,8,11-trioxa-5-azatridecan-13-yl)oxy]tricyclo[3.3.1.1$^{3,7}$]dec-1-yl}methyl)-5-methyl-1H-pyrazol-4-yl]pyridine-2-carboxylate The title compound was prepared by substituting EXAMPLE 86F for EXAMPLE 4A in EXAMPLE 4C.

Example 86H

6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl})-5-methyl-1H-pyrazol-4-yl)pyridine-2-carboxylic acid The title compound was prepared by substituting EXAMPLE 86G for EXAMPLE 2B in EXAMPLE 2C. $^1$H NMR (300 MHz, dimethylsulfoxide-d$_6$) δ ppm 12.85 (bs, 1H), 8.33 (bs, 2H), 8.03 (d, 1H), 7.79 (d, 1H), 7.62 (d, 1H), 7.48 (m, 3H), 7.36 m, 2H), 7.28 (s, 1H), 6.95 (d, 1H), 4.95 (s, 2H), 3.86 (m, 4H), 3.63 (m, 2H), 3.55 (s, 4H), 3.05 (d, 4H), 2.56 (t, 2H), 2.10 (s, 3H), 1.27 (m, 6H), 1.06 (m, 6H), 0.85 (s, 6H).

---

What is claimed is:

1. A compound or therapeutically acceptable salt thereof, wherein the compound is selected from the group consisting of

- 6-[8-(1,3-benzothiazol-2-ylcarbamoyl)-3,4-dihydroisoquinolin-2(1H)-yl]-3-{2-methyl-4-[tricyclo[3.3.1.1$^{3,7}$]dec-1-ylmethoxy]phenyl}pyridine-2-carboxylic acid;
- 6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylmethoxy]phenyl}pyridine-2-carboxylic acid;
- 6-[8-(1,3-benzothiazol-2-ylcarbamoyl)-3,4-dihydroisoquinolin-2(1H)-yl]-3-{3-[tricyclo[3.3.1.1$^{3,7}$]dec-1-ylmethoxy]phenyl}pyridine-2-carboxylic acid;
- 6-[8-(1,3-benzothiazol-2-ylcarbamoyl)-3,4-dihydroisoquinolin-2(1H)-yl]-2'-(tricyclo[3.3.1.1$^{3,7}$]dec-1-ylmethoxy)-3,4'-bipyridine-2-carboxylic acid;
- 6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylmethoxy)-3,4'-bipyridine-2-carboxylic acid;
- 6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-yloxy]phenyl}pyridine-2-carboxylic acid;
- 6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid;
- 6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid;
- 6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid;
- 6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylsulfamoyl]phenyl}pyridine-2-carboxylic acid;
- 6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylcarbonyl]amino}phenyl)pyridine-2-carboxylic acid;
- 6-[8-(1,3-benzothiazol-2-ylcarbamoyl)-3,4-dihydroisoquinolin-2(1H)-yl]-3-{2-methyl-3-[tricyclo[3.3.1.1$^{3,7}$]dec-1-ylcarbamoyl]phenyl}pyridine-2-carboxylic acid;
- 6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-1-ylmethyl]amino}phenyl)pyridine-2-carboxylic acid;
- 6-[8-(1,3-benzothiazol-2-ylcarbamoyl)-3,4-dihydroisoquinolin-2(1H)-yl]-3-[2-cyano-3-(tricyclo[3.3.1.1$^{3,7}$]dec-1-ylsulfonyl)phenyl]pyridine-2-carboxylic acid;
- 6-[8-(1,3-benzothiazol-2-ylcarbanoyl)-3,4-dihydroisoquinolin-2(1H)-yl]-2'-[cyclooctyl(methyl)amino]-3'-methyl-3,4'-bipyridine-2-carboxylic acid;
- 6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]carbamoyl}phenyl)pyridine-2-carboxylic acid;
- 6-[8-(1,3-benzothiazol-2-ylcarbamoyl)-3,4-dihydroisoquinolin-2(1H)-yl]-3-{2-methyl-3-[methyl(2-oxatricyclo[3.3.1.1$^{3,7}$]dec-1-ylcarbonyl)amino]phenyl}pyridine-2-carboxylic acid;
- 6-[8-(1,3-benzothiazol-2-ylcarbamoyl)-3,4-dihydroisoquinolin-2(1H)-yl]-3-(2-methyl-3-{methyl[tricyclo[3.3.1.1$^{3,7}$]dec-2-yl]sulfamoyl}phenyl)pyridine-2-carboxylic acid;
- 6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfonyl)-3,4'-bipyridine-2-carboxylic acid;
- 6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylsulfanyl)-3,4'-bipyridine-2-carboxylic acid;
- 6-[8-(1,3-benzothiazol-2-ylcarbamoyl)-3,4-dihydroisoquinolin-2(1H)-yl]-3'-methyl-2'-(tricyclo[3.3.1.1$^{3,7}$]dec-1-ylamino)-3,4'-bipyridine-2-carboxylic acid; and
- 6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid.

2. A composition comprising an excipient and a therapeutically effective amount of the compound or therapeutically acceptable salt of claim 1.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: F-Bak Probe Peptide
<220> FEATURE:
<221> NAME/KEY: MOD_RES
```

```
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
 1               5                  10                  15
```